(12) United States Patent
Sprecker et al.

(10) Patent No.: US 6,271,193 B1
(45) Date of Patent: Aug. 7, 2001

(54) CARBON CONTAINING FUNCTIONAL GROUP SUBSTITUTED 4,5,6,7-TETRAHYDRO-POLYALKYLATED-4-INDANES, ISOMERS THEREOF, PROCESSES FOR PREPARING SAME AND USES THEREOF

(75) Inventors: Mark A. Sprecker, Sea Bright; Richard A. Weiss, Livingston; Anthony T. Levorse, Jr., South Amboy; Howard H. Heinsohn, Jr., Freehold; Charles E. J. Beck, Summit; Marie R. Hanna, Hazlet, all of NJ (US)

(73) Assignee: International Flavors & Fragrances Inc., New York, NY (US)

( * ) Notice: Subject to any disclaimer, the term of this patent is extended or adjusted under 35 U.S.C. 154(b) by 0 days.

(21) Appl. No.: 09/686,163

(22) Filed: Oct. 11, 2000

(51) Int. Cl.[7] ............................ C07C 45/50; C07C 47/28; C07C 47/38; A61K 7/46; C11D 3/50; C11D 9/44
(52) U.S. Cl. ................................ 512/8; 512/17; 512/19; 568/444; 568/445; 568/446; 510/101
(58) Field of Search ........................ 568/444, 445, 568/446; 512/8, 17, 19; 510/568, 101

(56) References Cited

U.S. PATENT DOCUMENTS

| | | |
|---|---|---|
| 3,636,165 | 1/1972 | Hall . |
| 3,636,176 | 1/1972 | Hall . |
| 3,773,836 | * 11/1973 | Hall . |
| 3,806,472 | * 4/1974 | Hall . |
| 4,902,840 | 2/1990 | Sprecker et al. . |
| 5,281,576 | 1/1994 | Narula et al. . |
| 5,494,892 | * 2/1996 | Sprecker et al. . |
| 5,837,877 | 11/1998 | Mitsuhashi et al. . |
| 5,922,918 | 7/1999 | Zhang et al. . |

FOREIGN PATENT DOCUMENTS

| | | |
|---|---|---|
| 198 14 913 | 10/1999 | (DE) . |
| 198 17 042 | 10/1999 | (DE) . |
| 198 17 043 | 10/1999 | (DE) . |
| 198 17 044 | 10/1999 | (DE) . |
| 0 877 029 A2 | 11/1998 | (EP) . |
| WO 97/20789 | 6/1997 | (WO) . |
| WO 99/54429 | 10/1999 | (WO) . |
| WO 99/54430 | 10/1999 | (WO) . |
| WO99/54428 | 10/1999 | (WO) . |

OTHER PUBLICATIONS

*Organic Syntheses*, Kitamura, et al., Larry E. Overman, Editor, vol. 71 (1992) C & EN (Science/Technology section), Nov. 22, 1999, title: "Chiral Triumphs" by Stephen C. Stinson.

*Tetrahedron*, vol. 50, No. 2, pp. 335–346, 1994, Pergamon Press (Great Britain), title: "Catalytic Asymmetric Synthesis of β—Hydroxy Ketones by Palladium–Catalyzed Assymmetric 1,4—Disilyation of α, β—Unsaturated Ketones."

* cited by examiner

*Primary Examiner*—Johann Richter
*Assistant Examiner*—Sikarl A. Witherspoon
(74) *Attorney, Agent, or Firm*—Joseph F. Leightner

(57) ABSTRACT

Described are carbon-containing functional groups substituted 4,5,6,7-tetrahydro-polyalkylated-4-indanes, isomers thereof, process for processes for preparing same, and uses thereof. The 4,5,6,7-tetrahydro-polyalkylated-4-indanes have the generic structure:

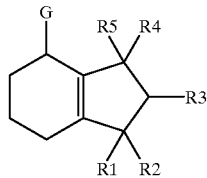

Wherein G and $R_{1-5}$ are as defined in the specification. The aforementioned materials have fragrance properties or are intermediates for materials which have fragrance properties. Also described are processes for producing the aforementioned substances.

19 Claims, 33 Drawing Sheets

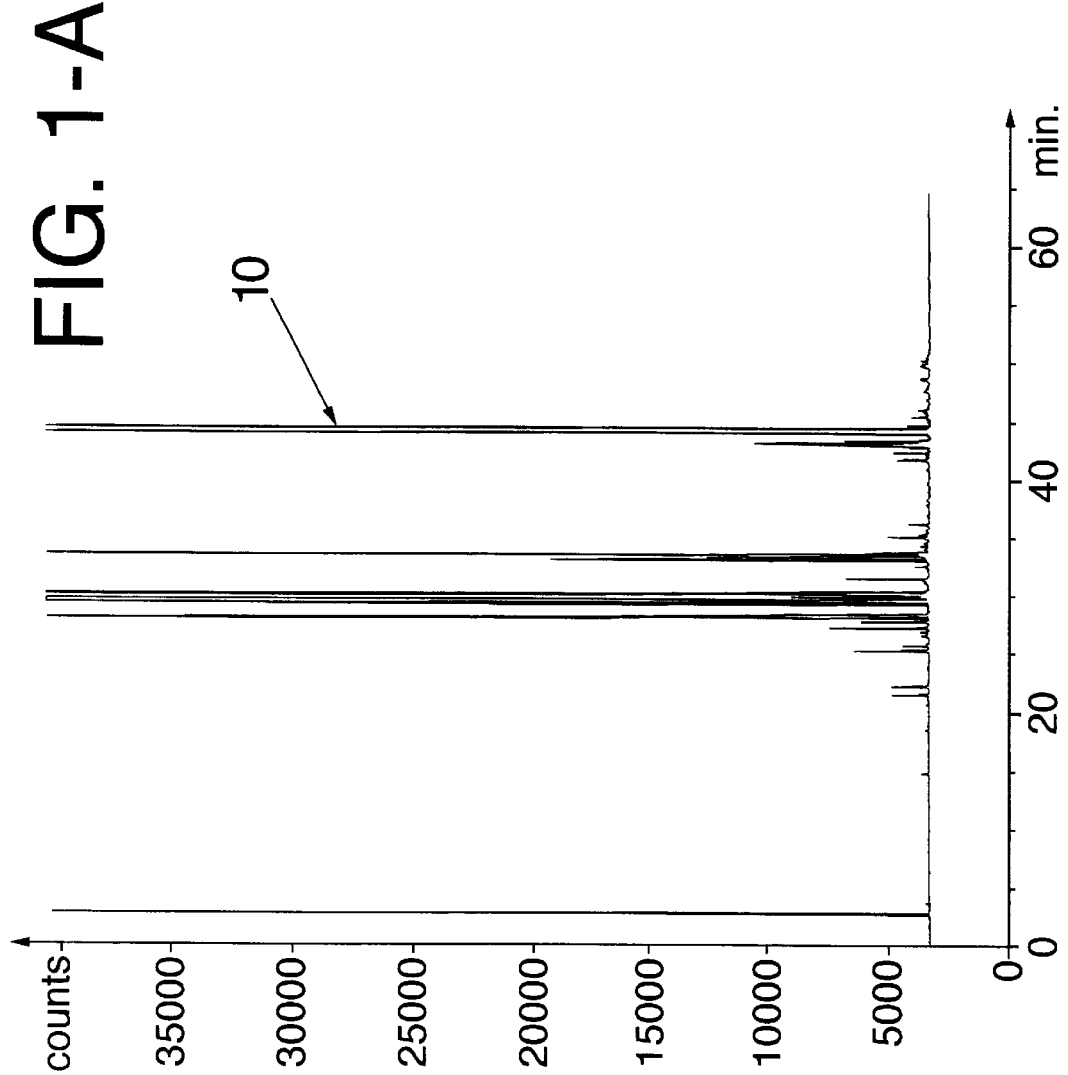

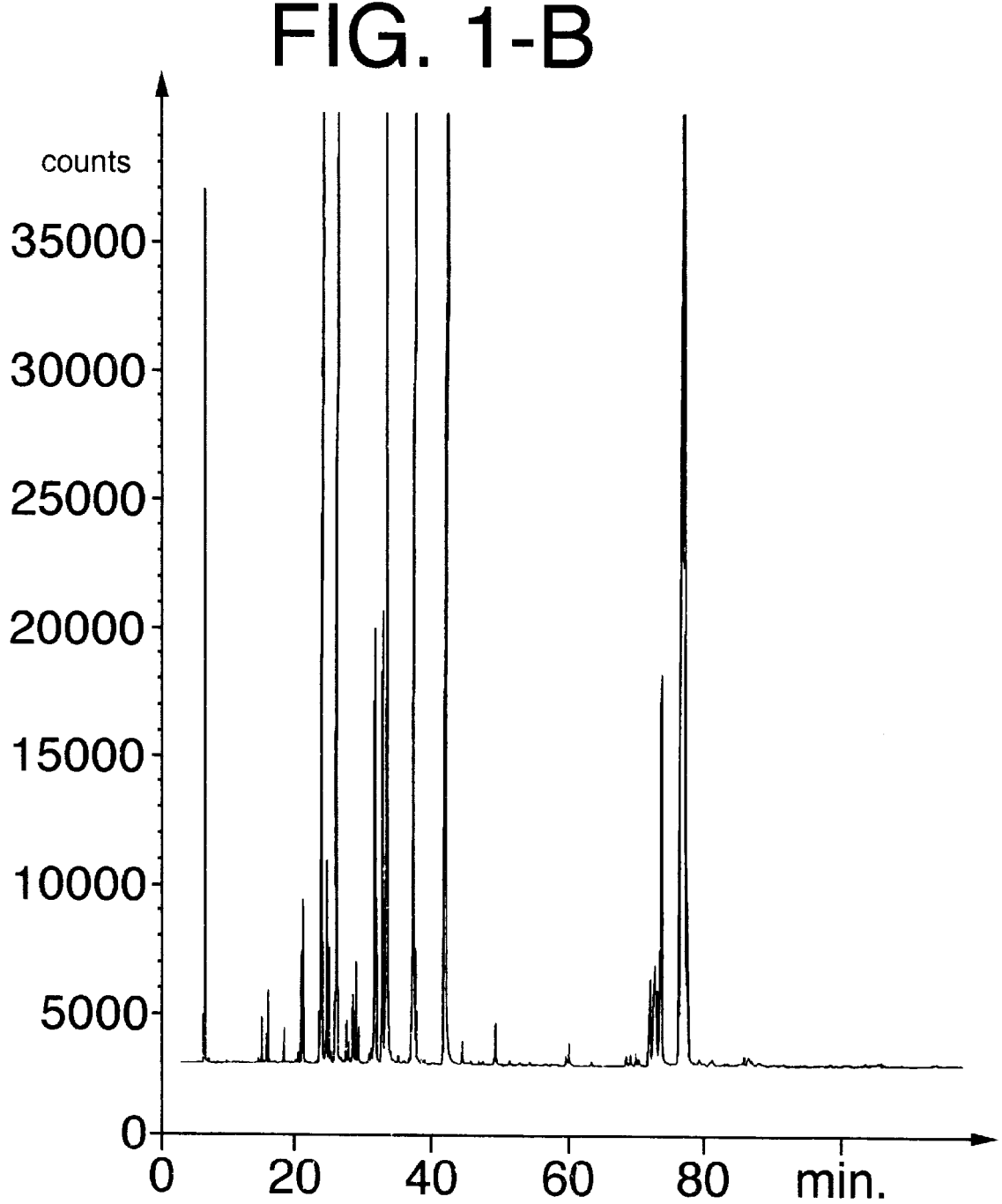

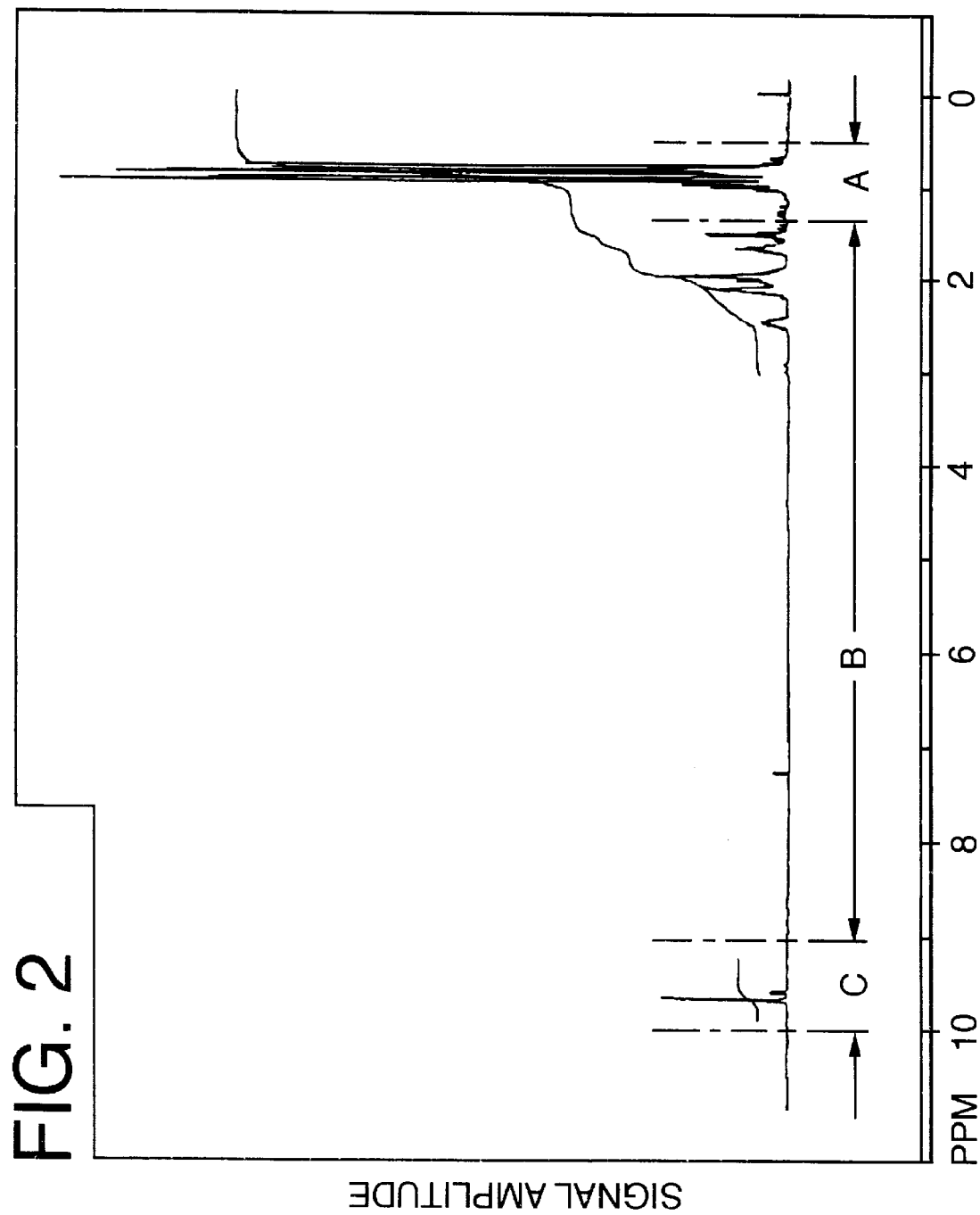

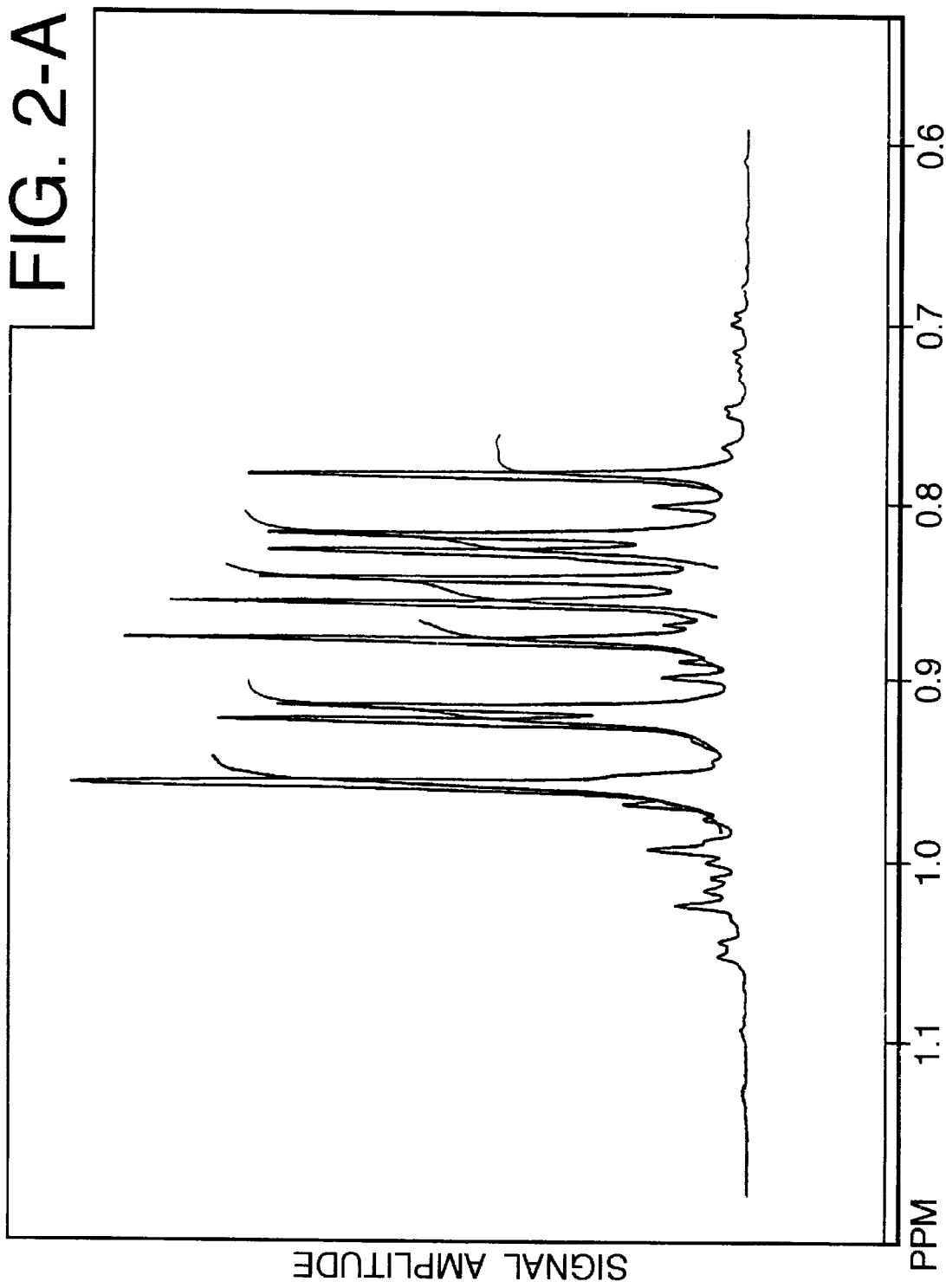

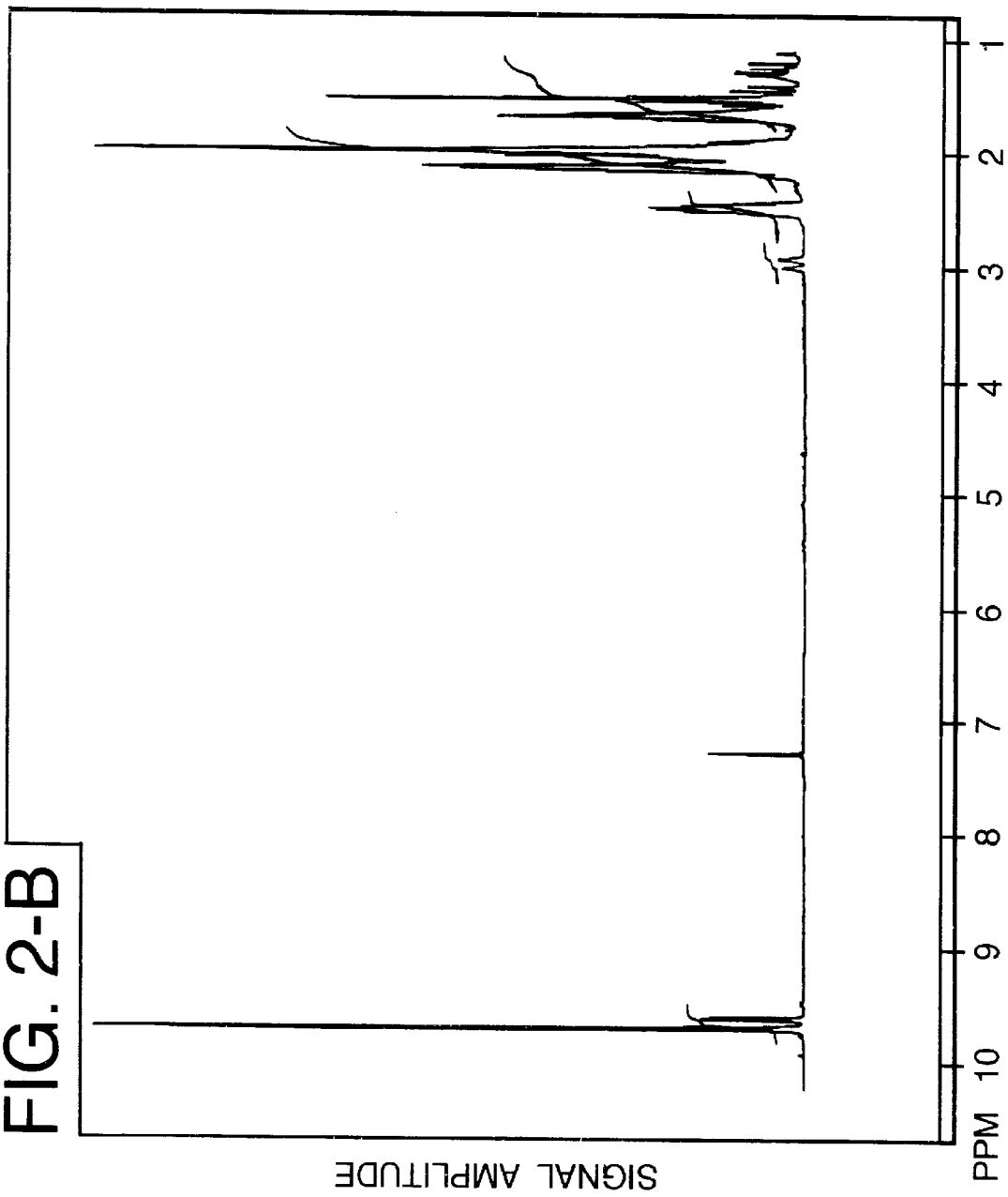
FIG. 2-B

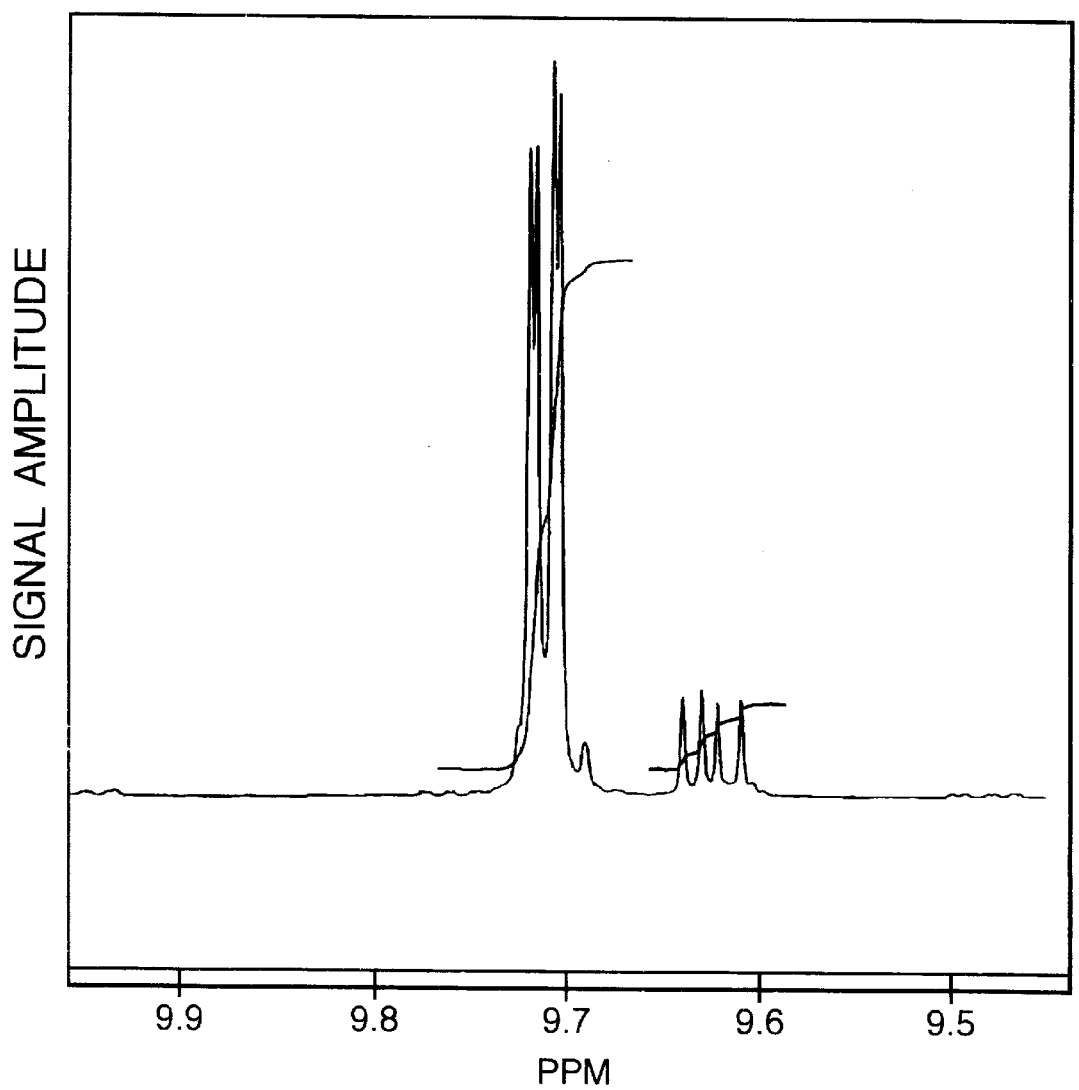
FIG. 2-C

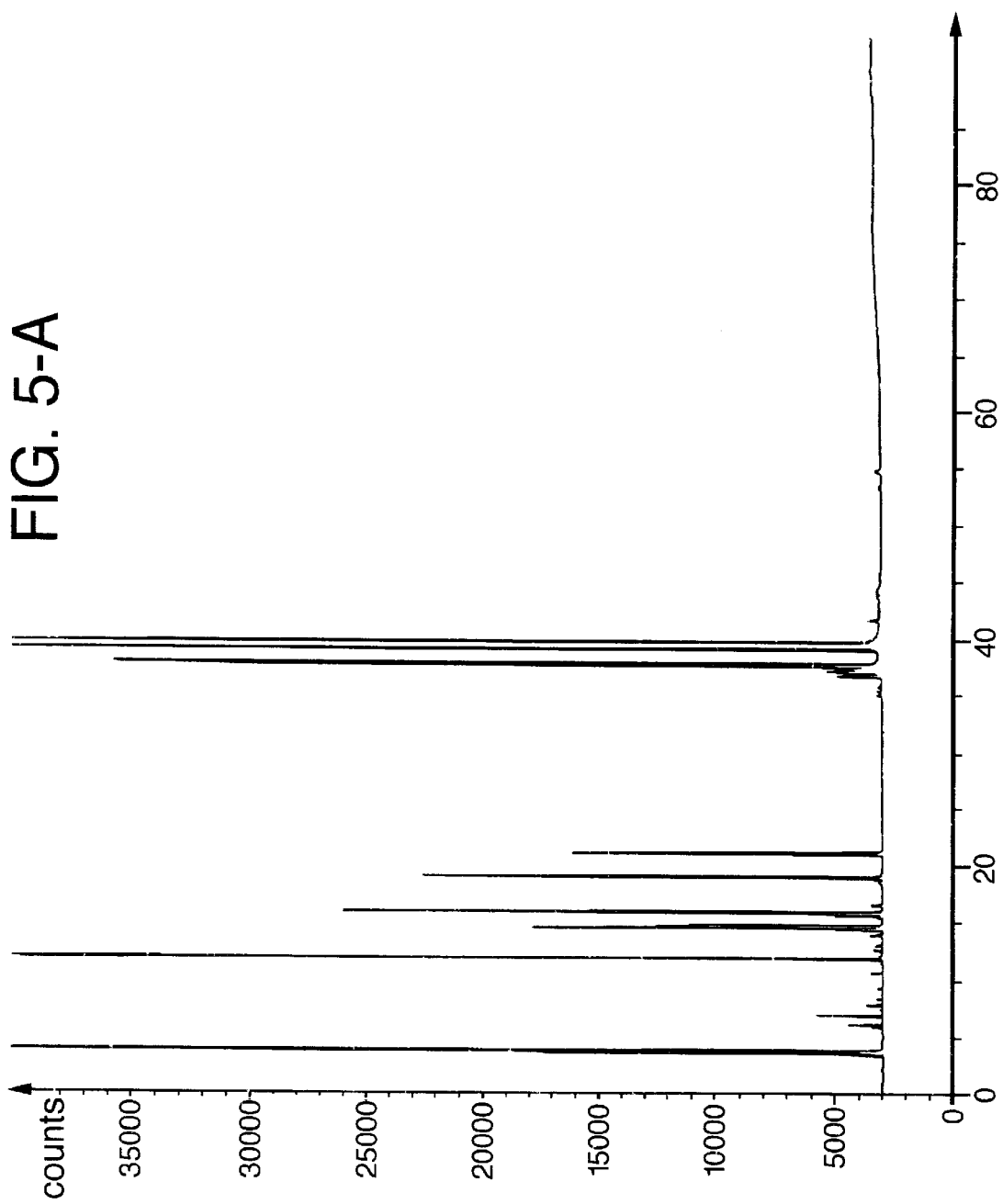

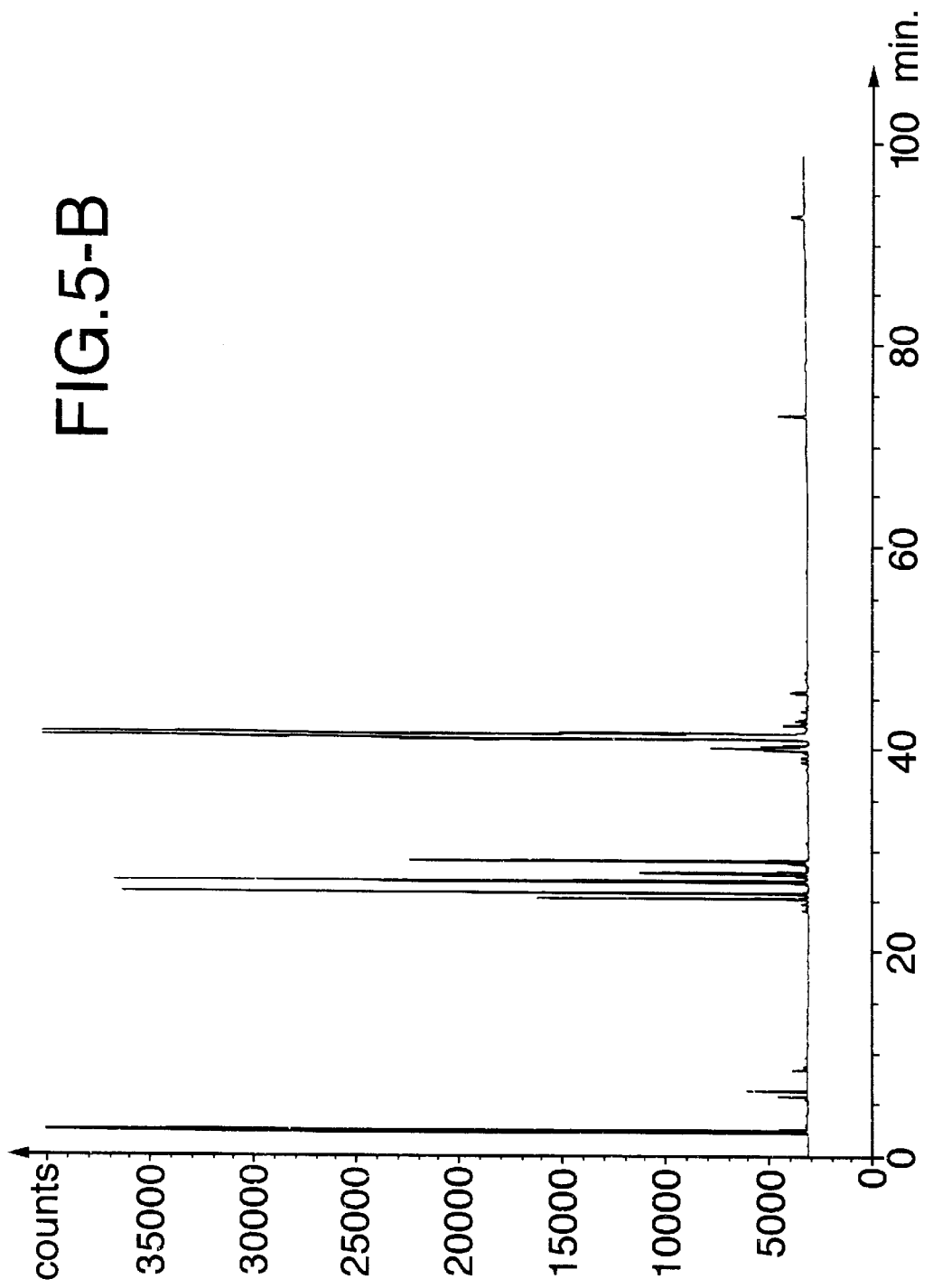

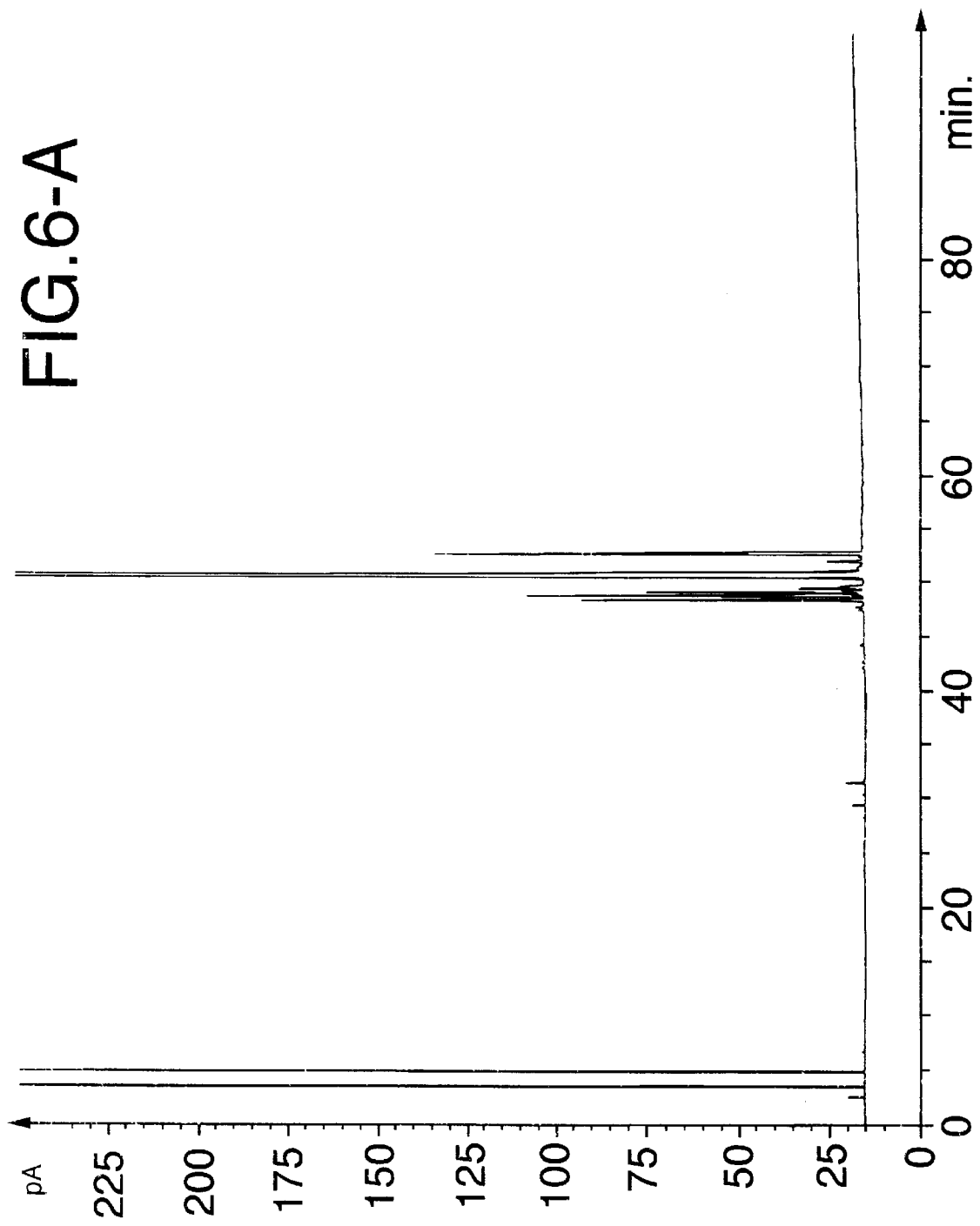

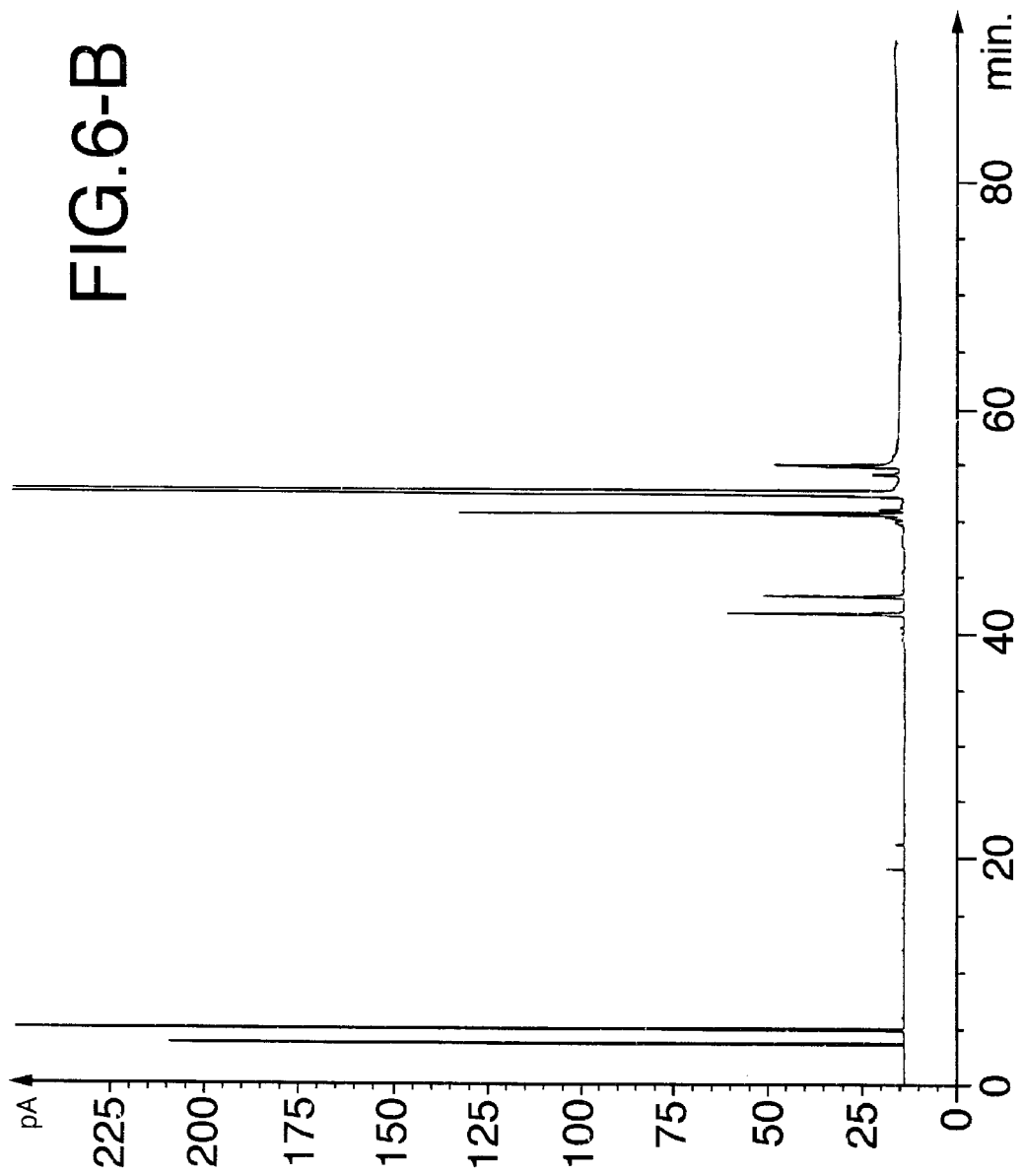

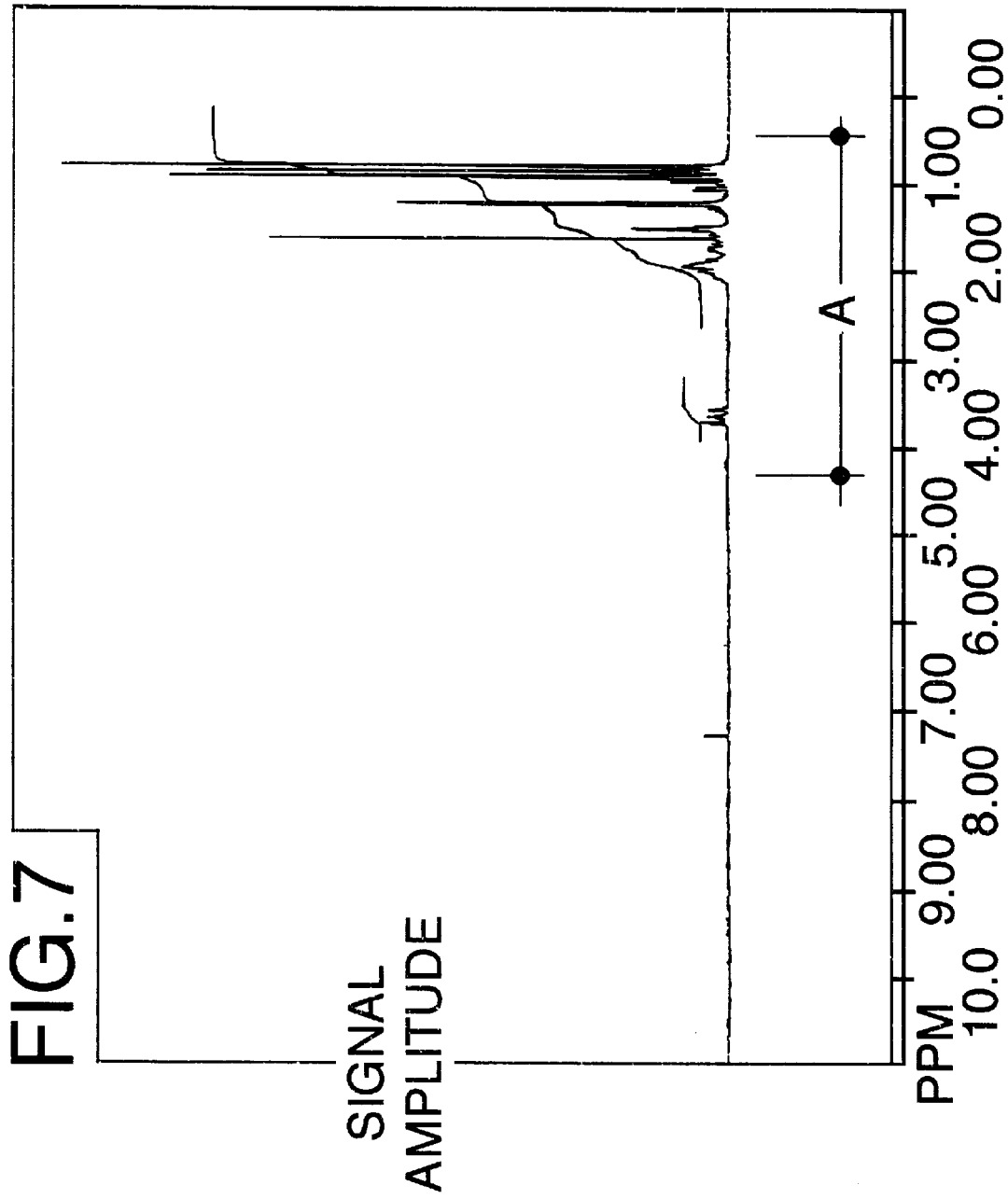

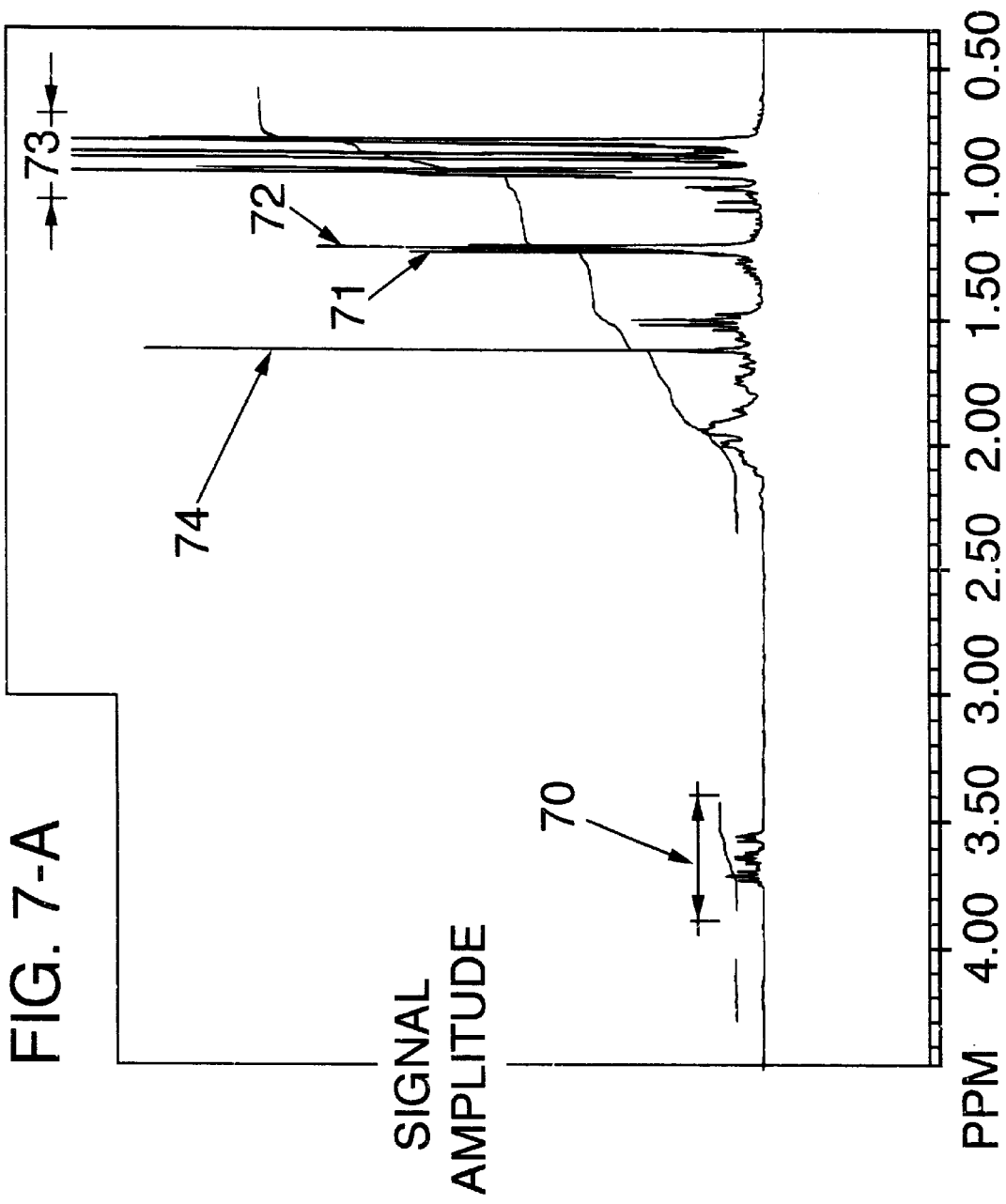
FIG. 7-A

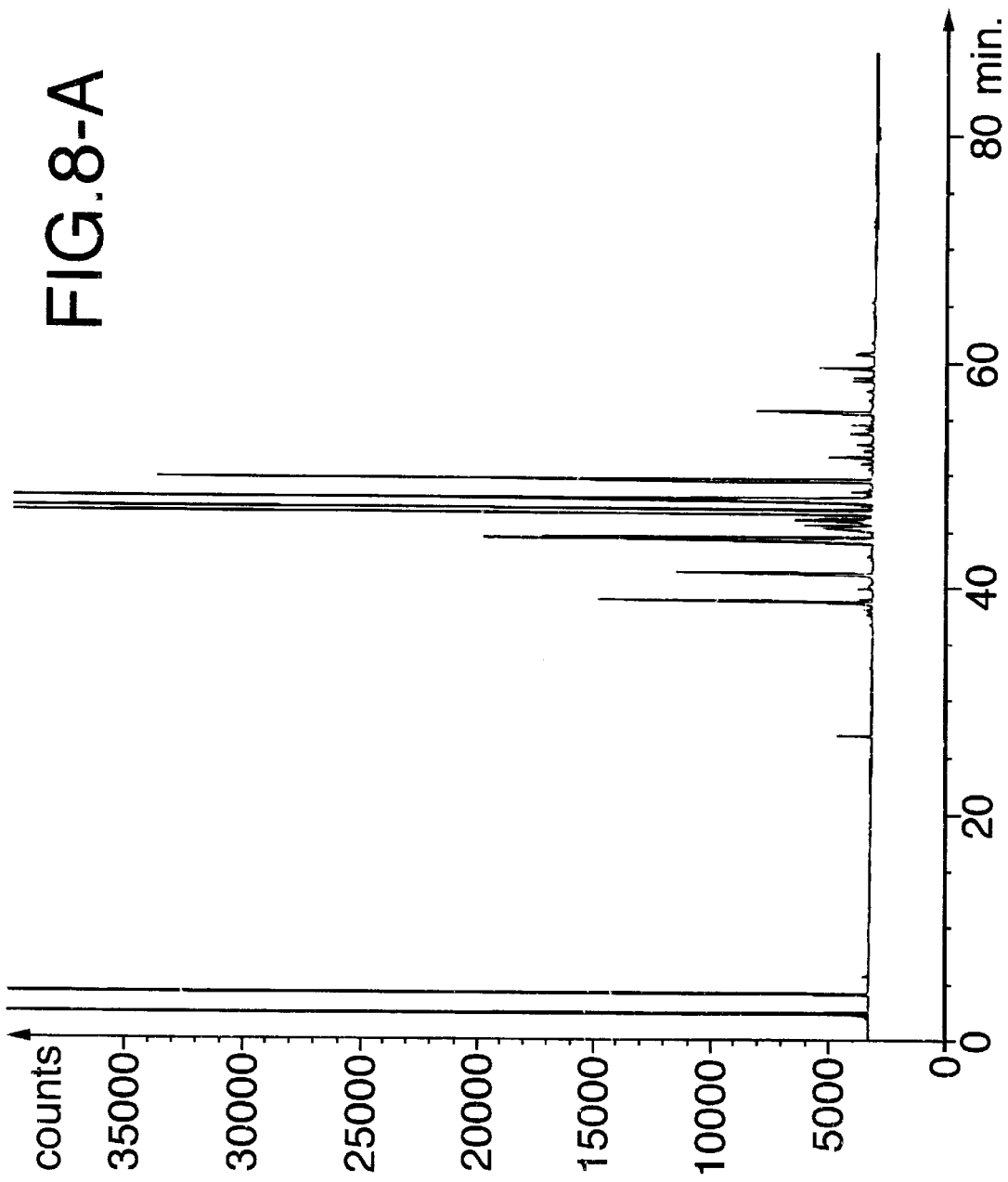

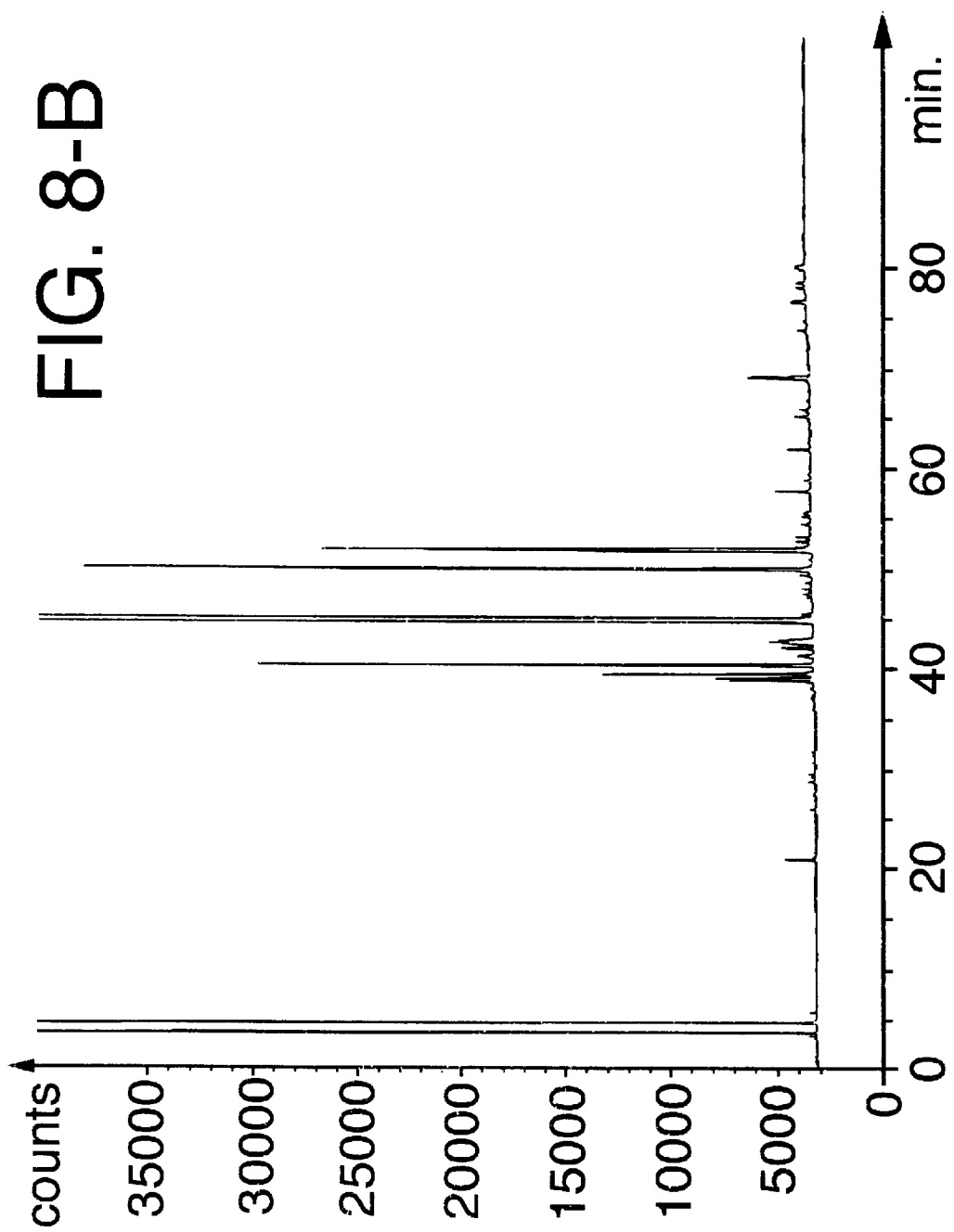

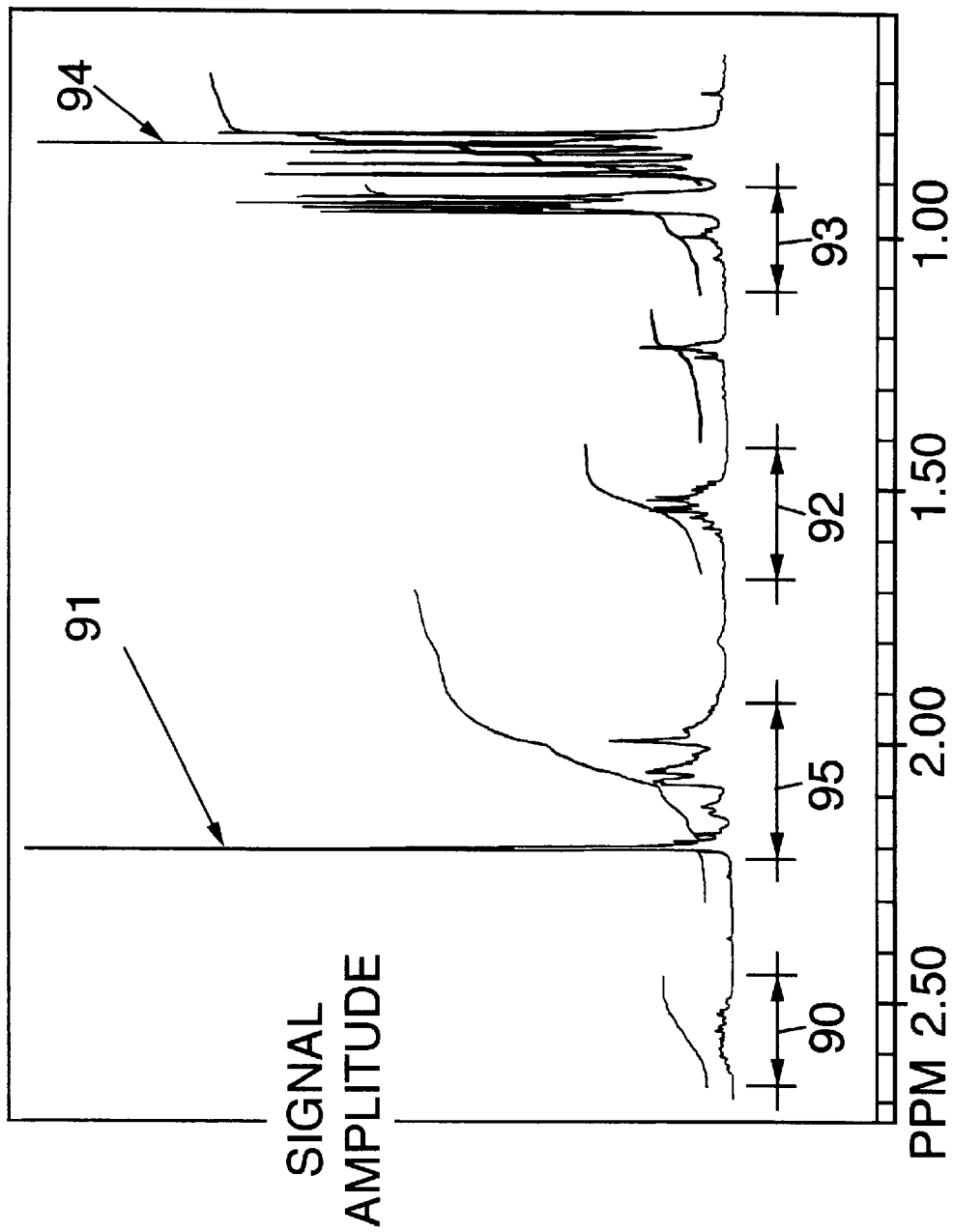
FIG. 9-A

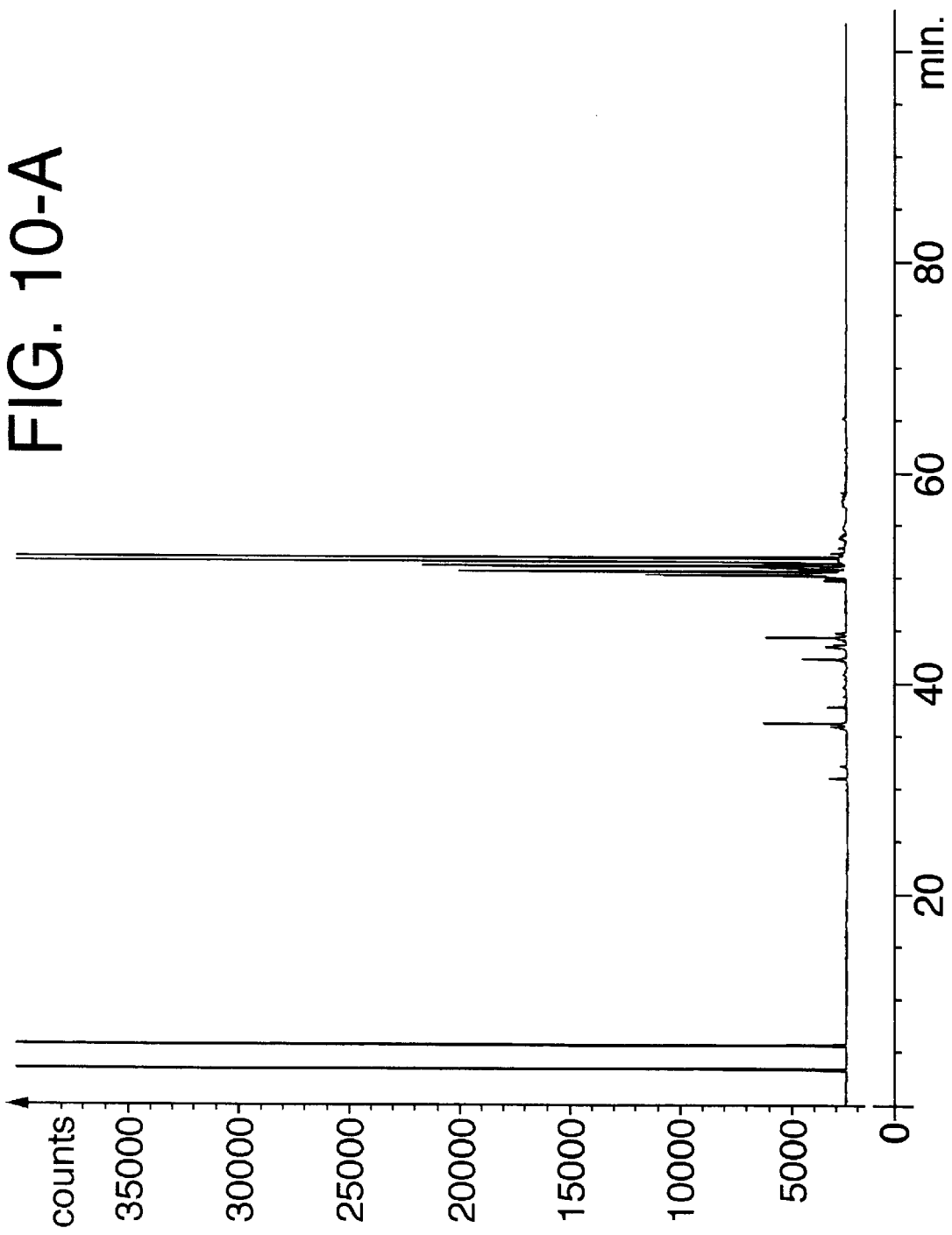
FIG. 10-A

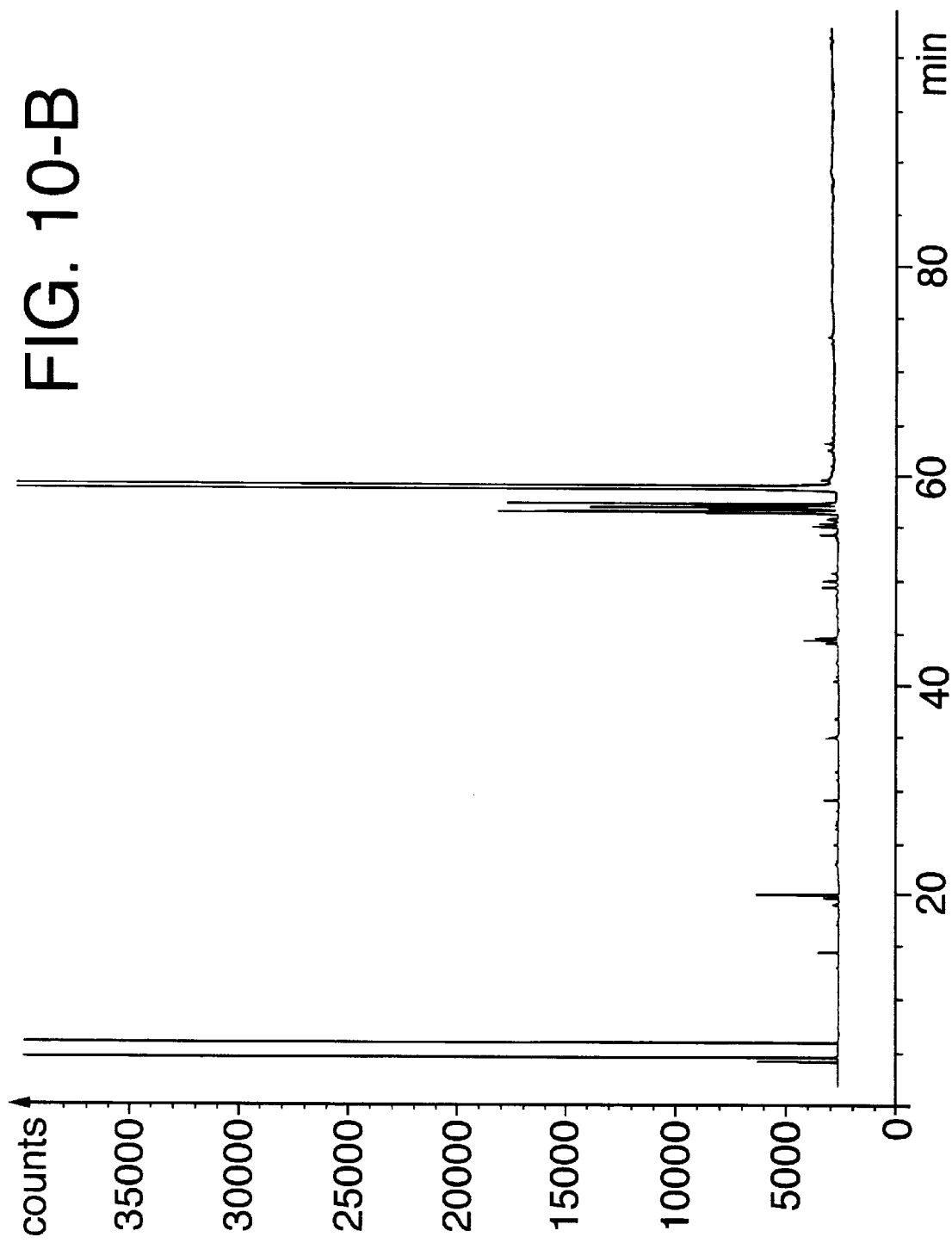

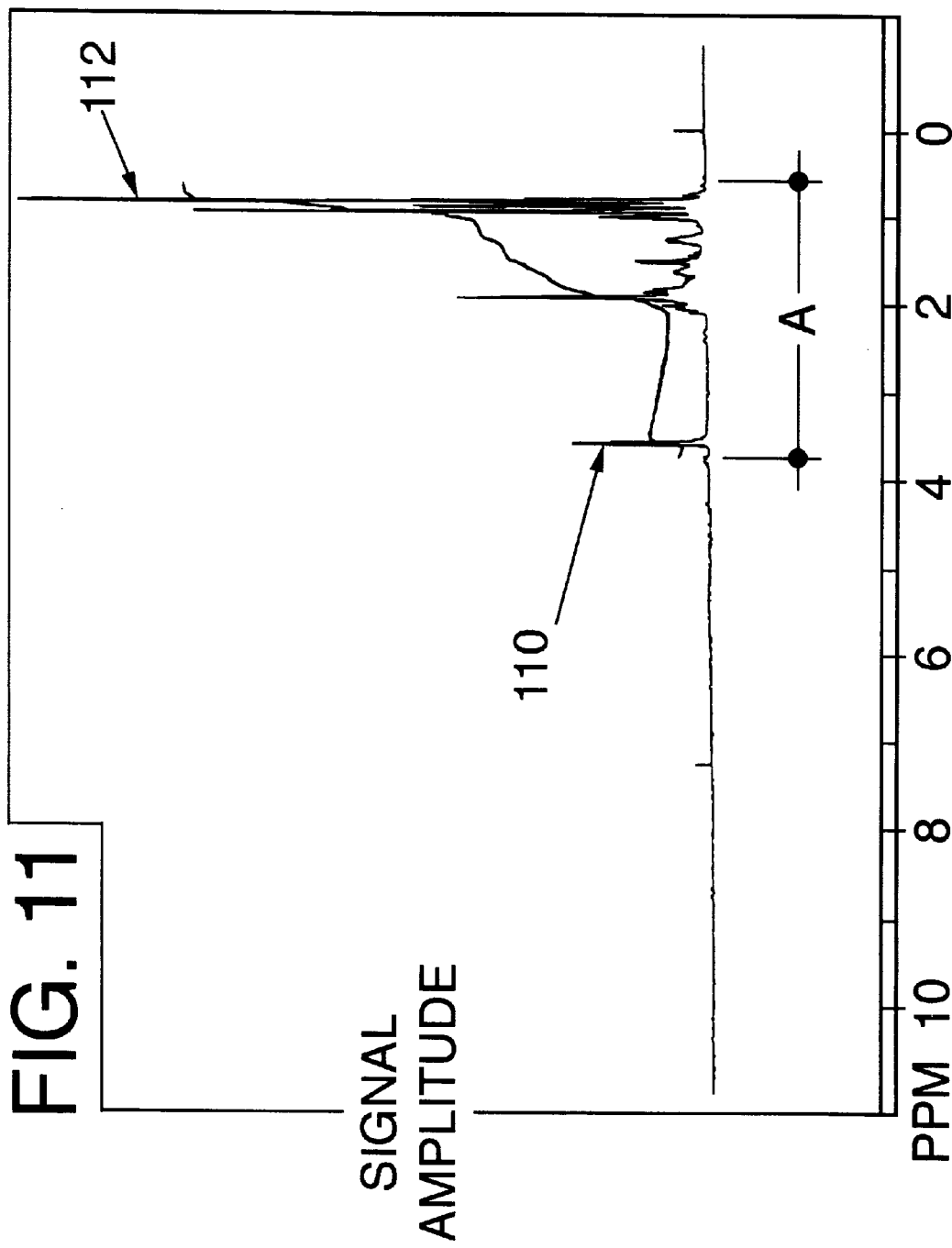

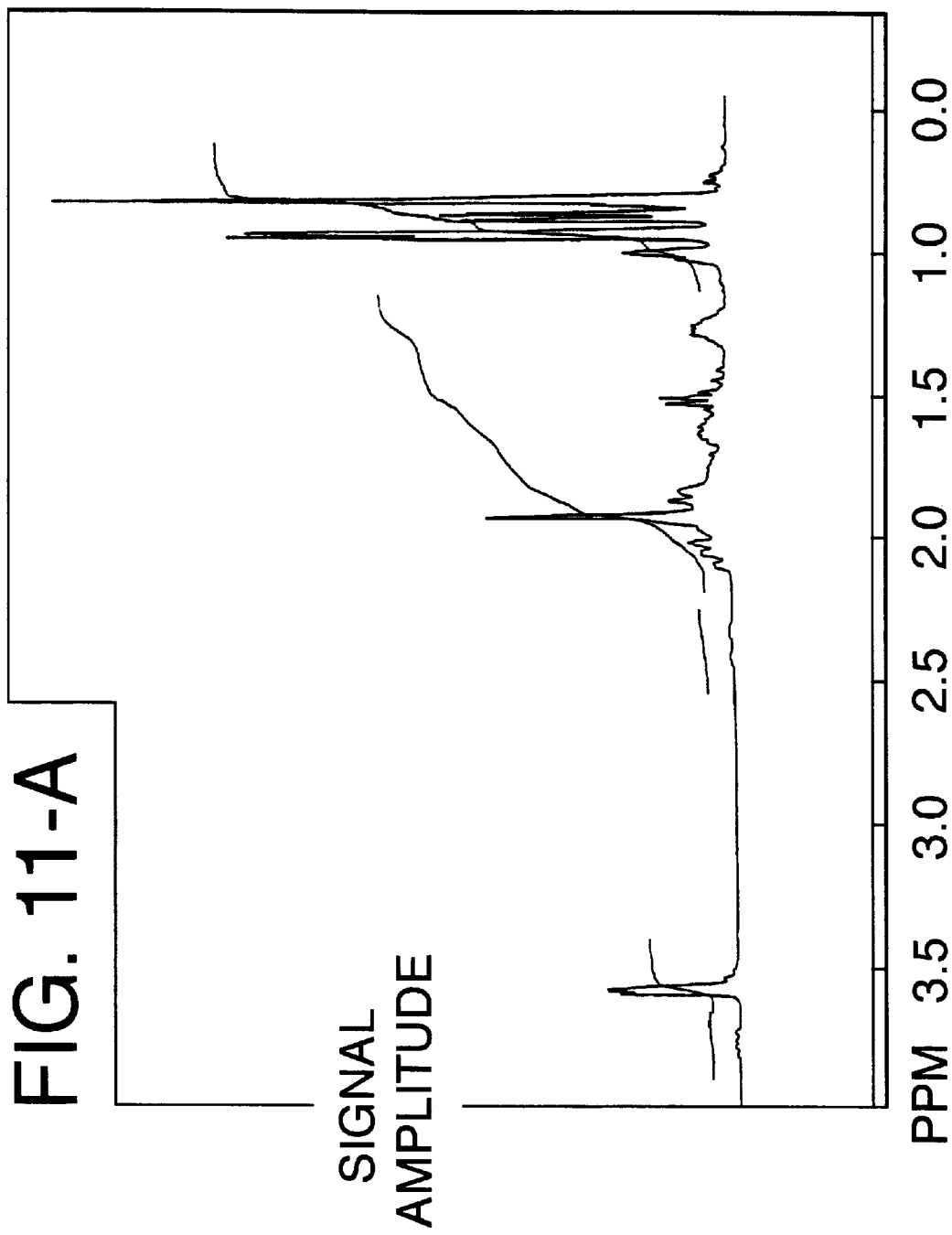
FIG. 11-A

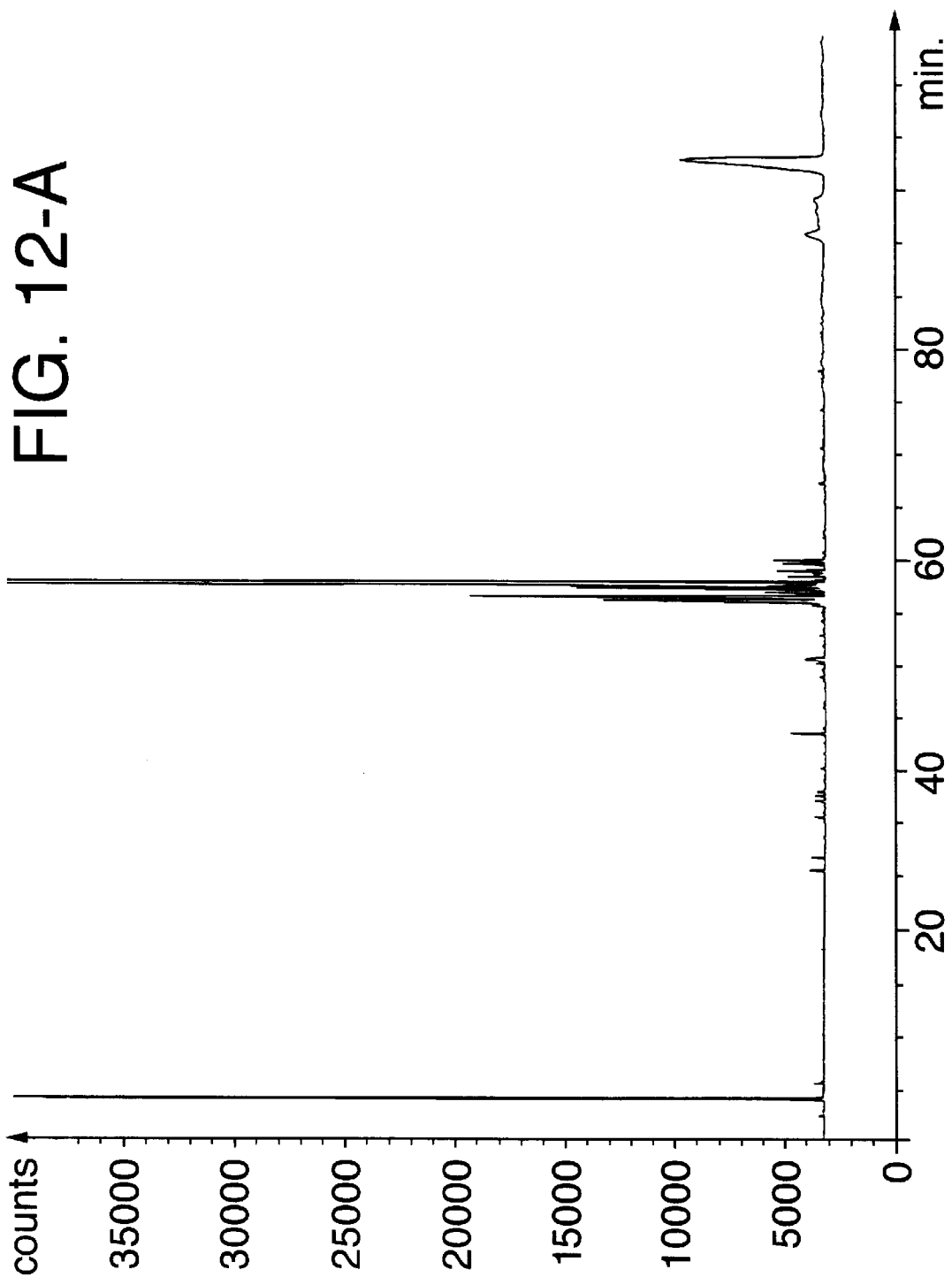

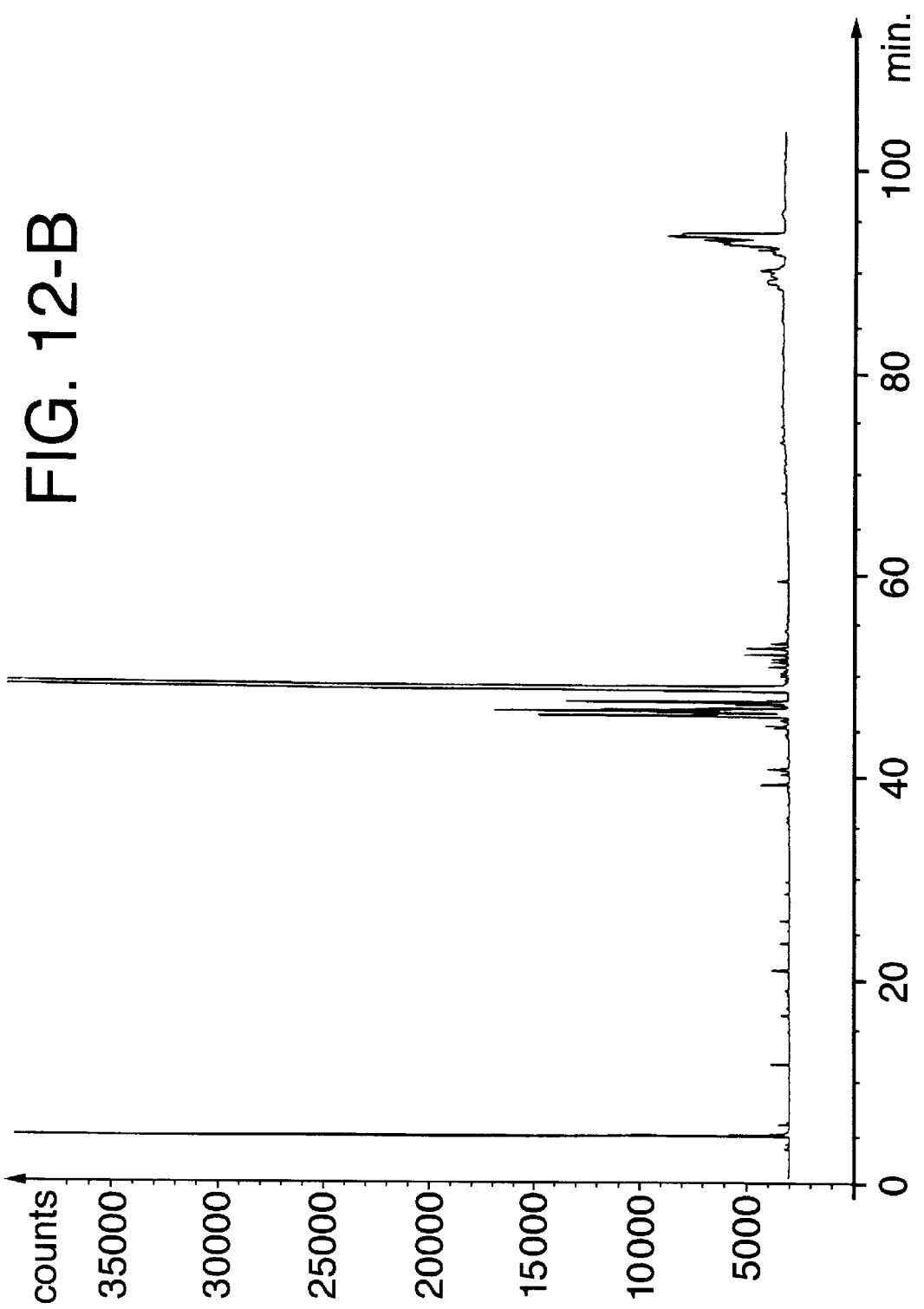

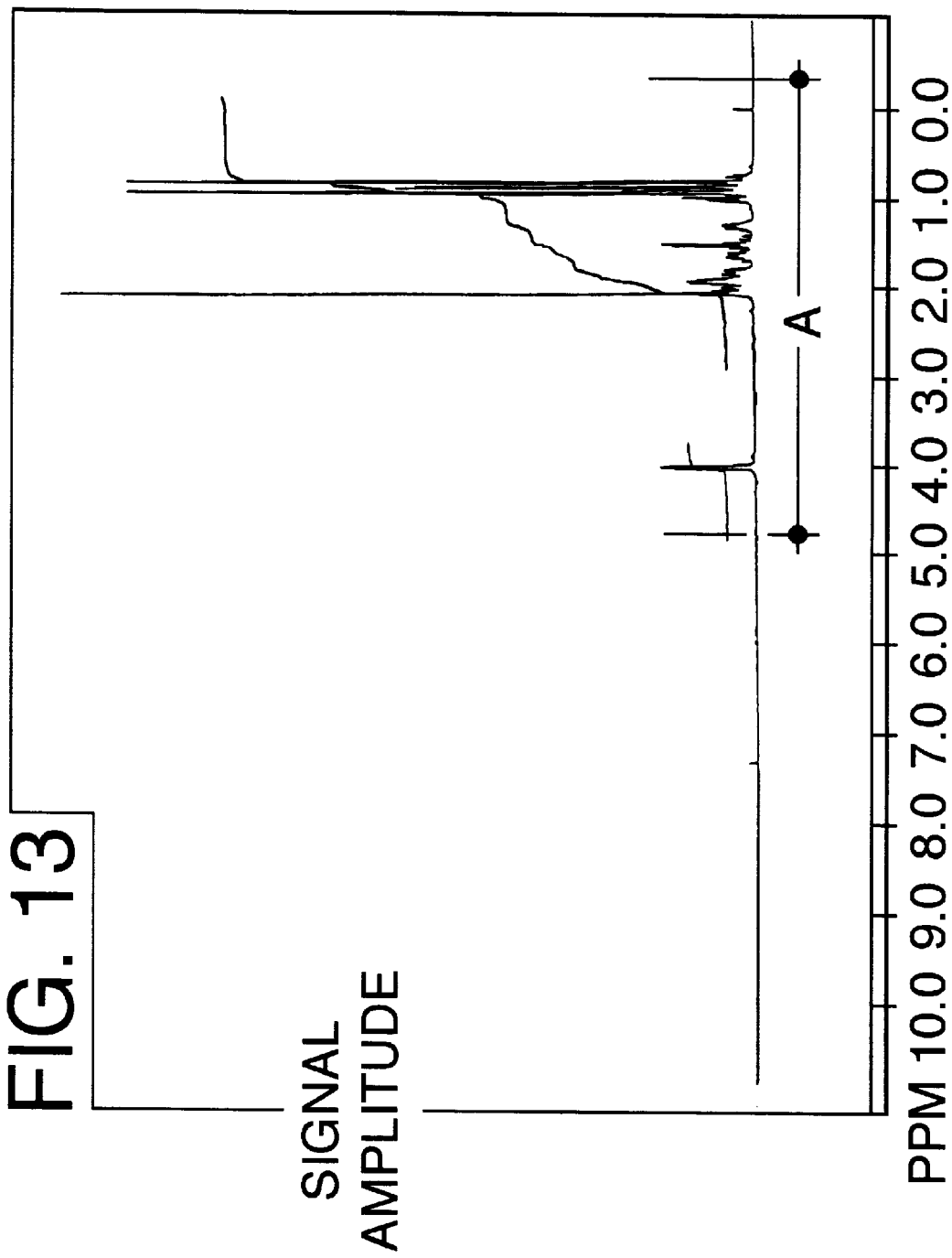

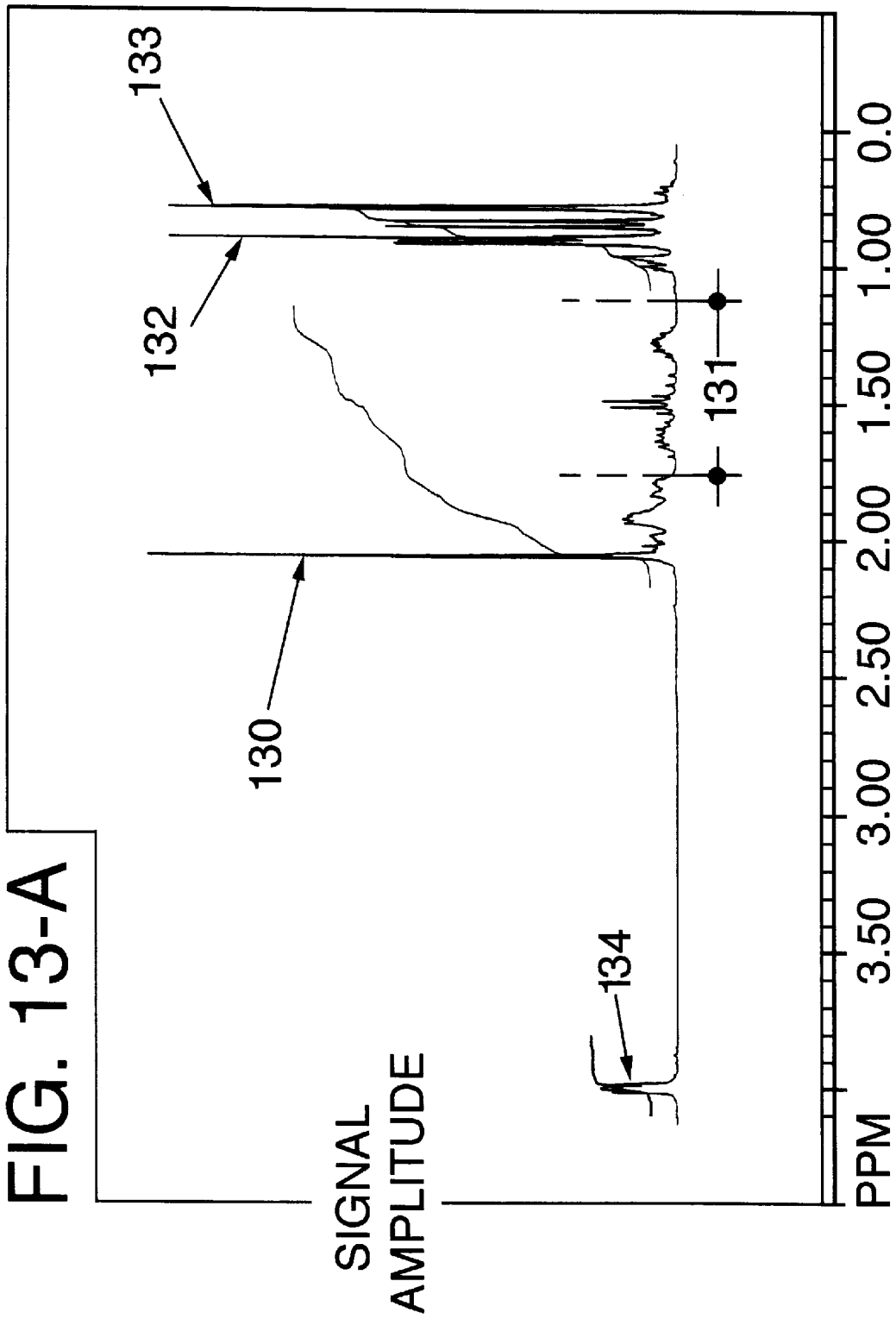
FIG. 13-A

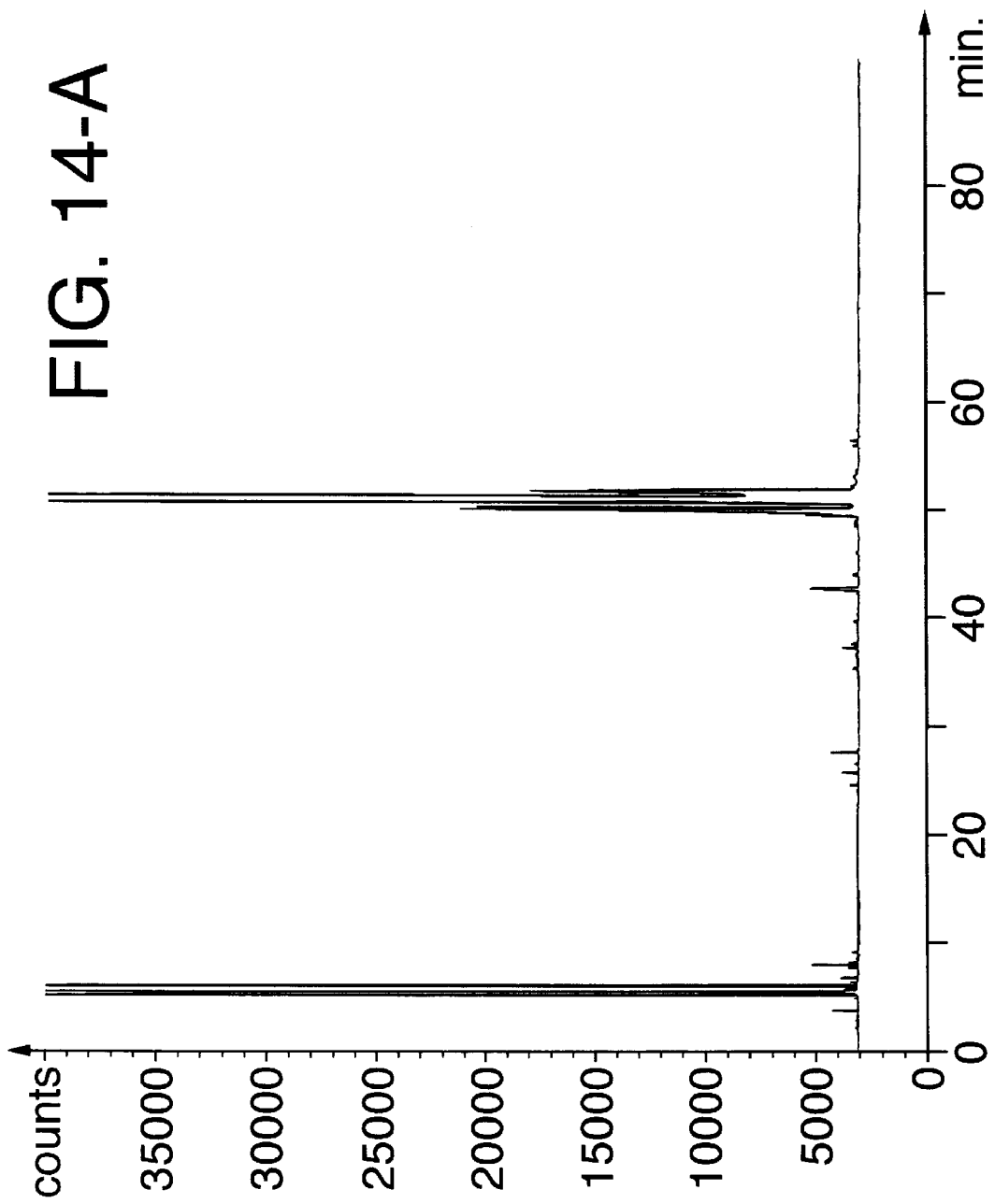
FIG. 14-A

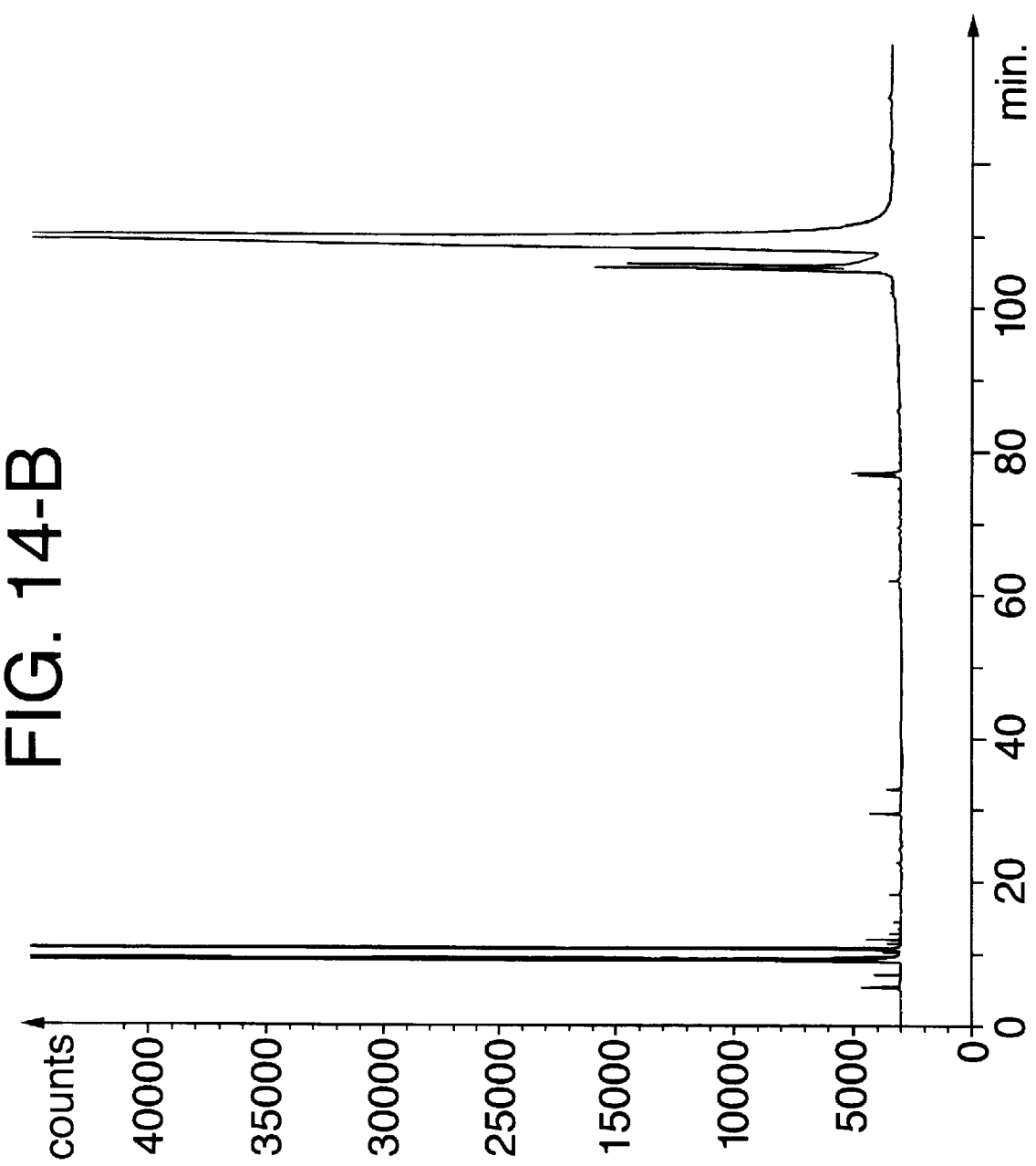

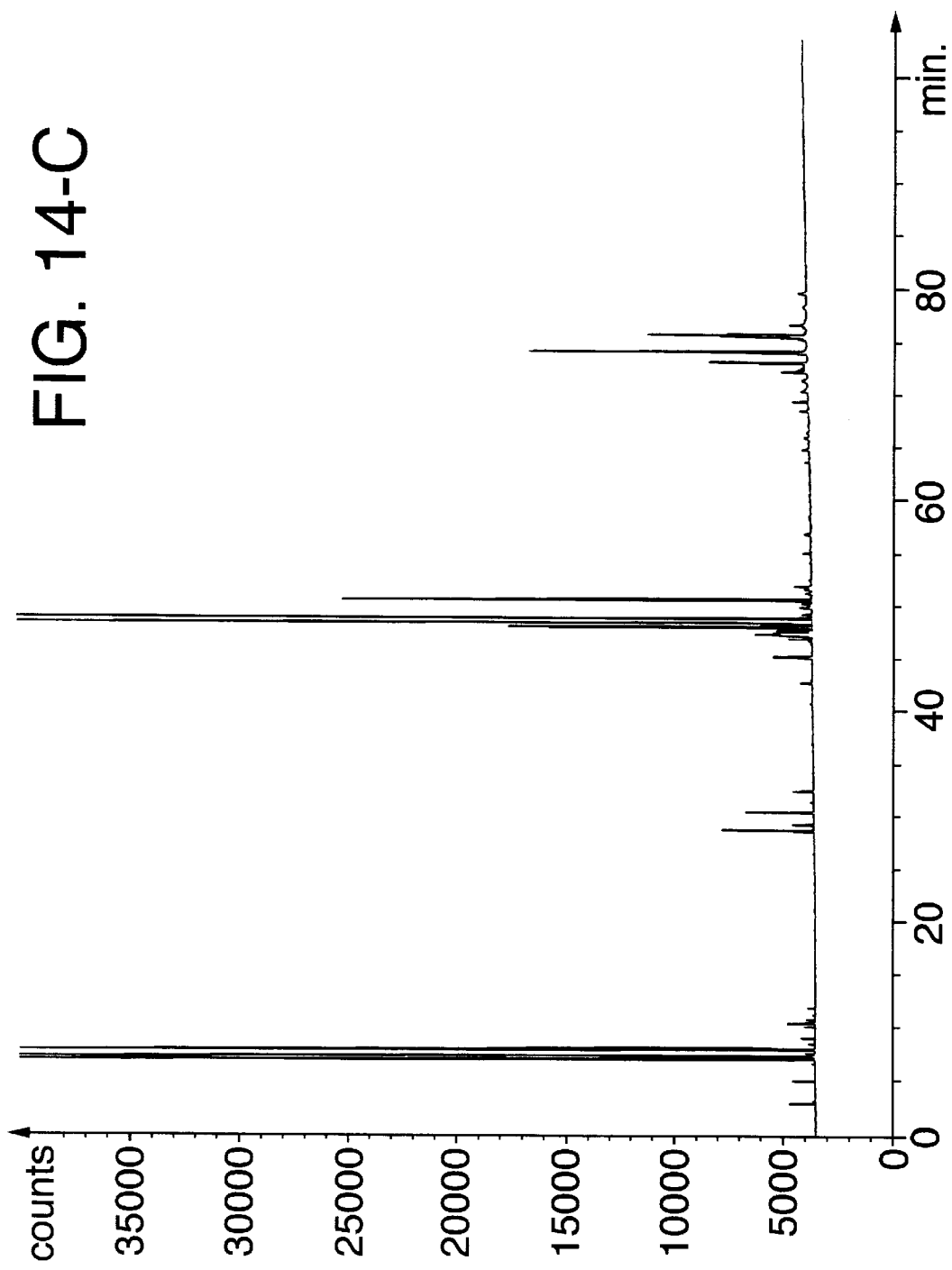
FIG. 14-C

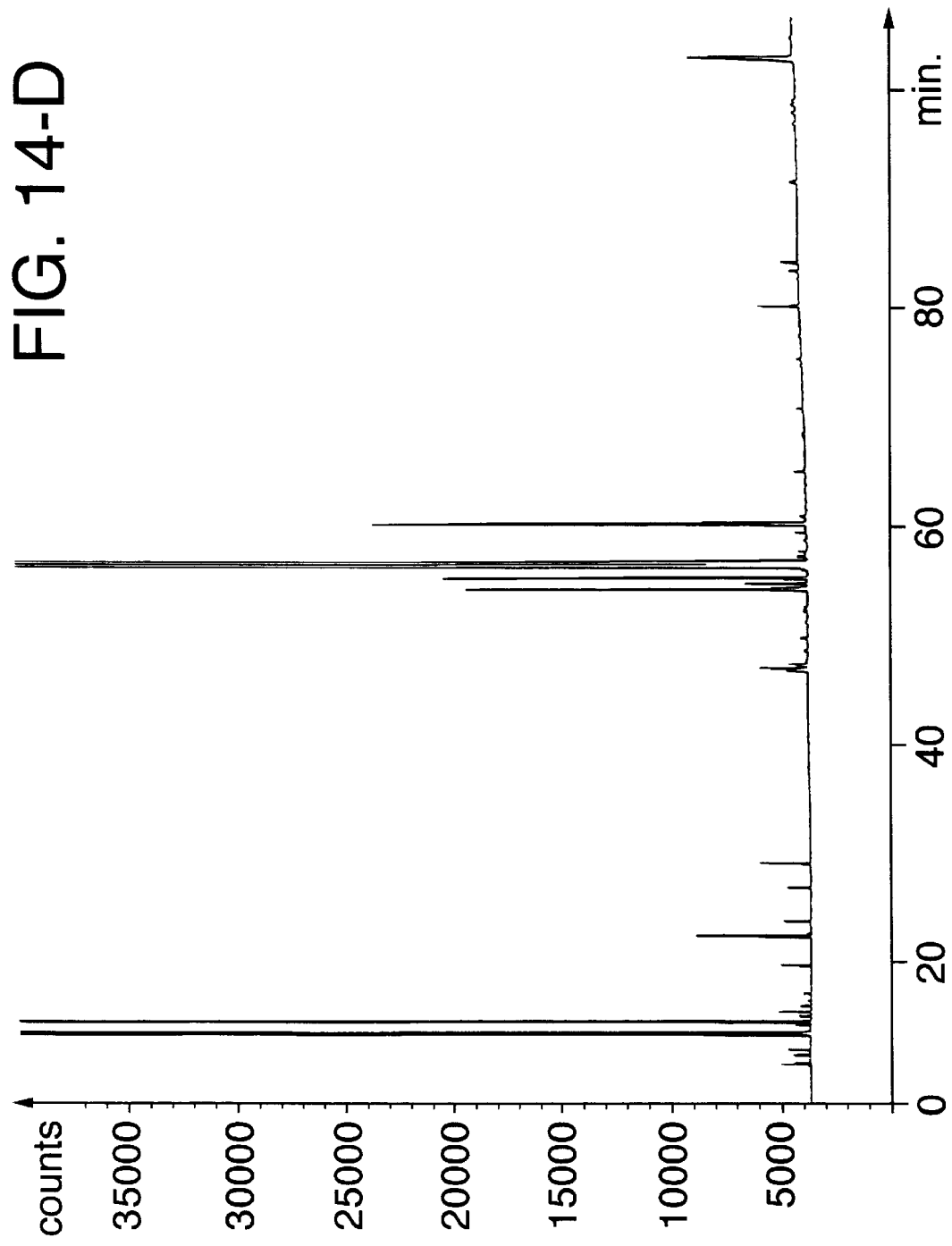

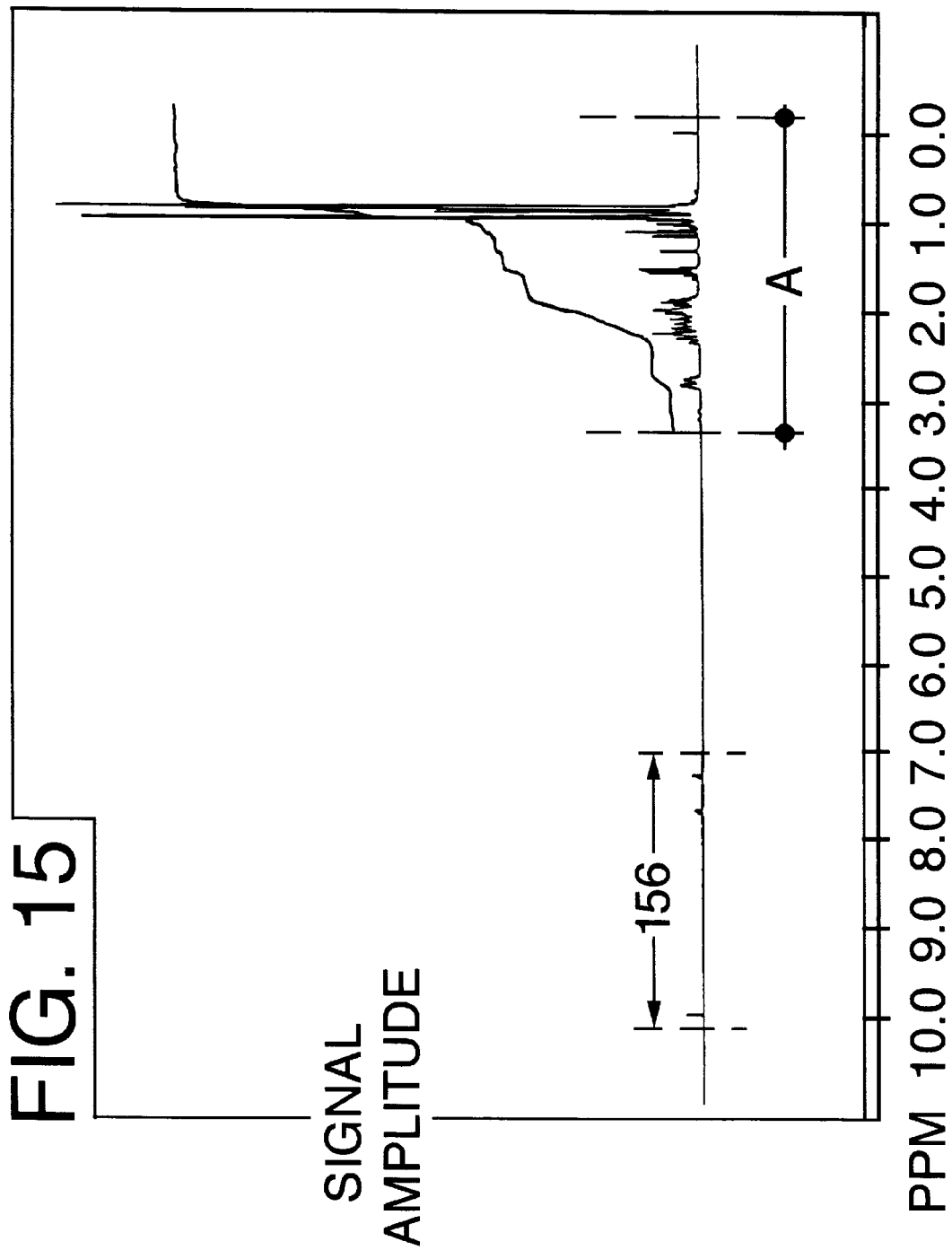

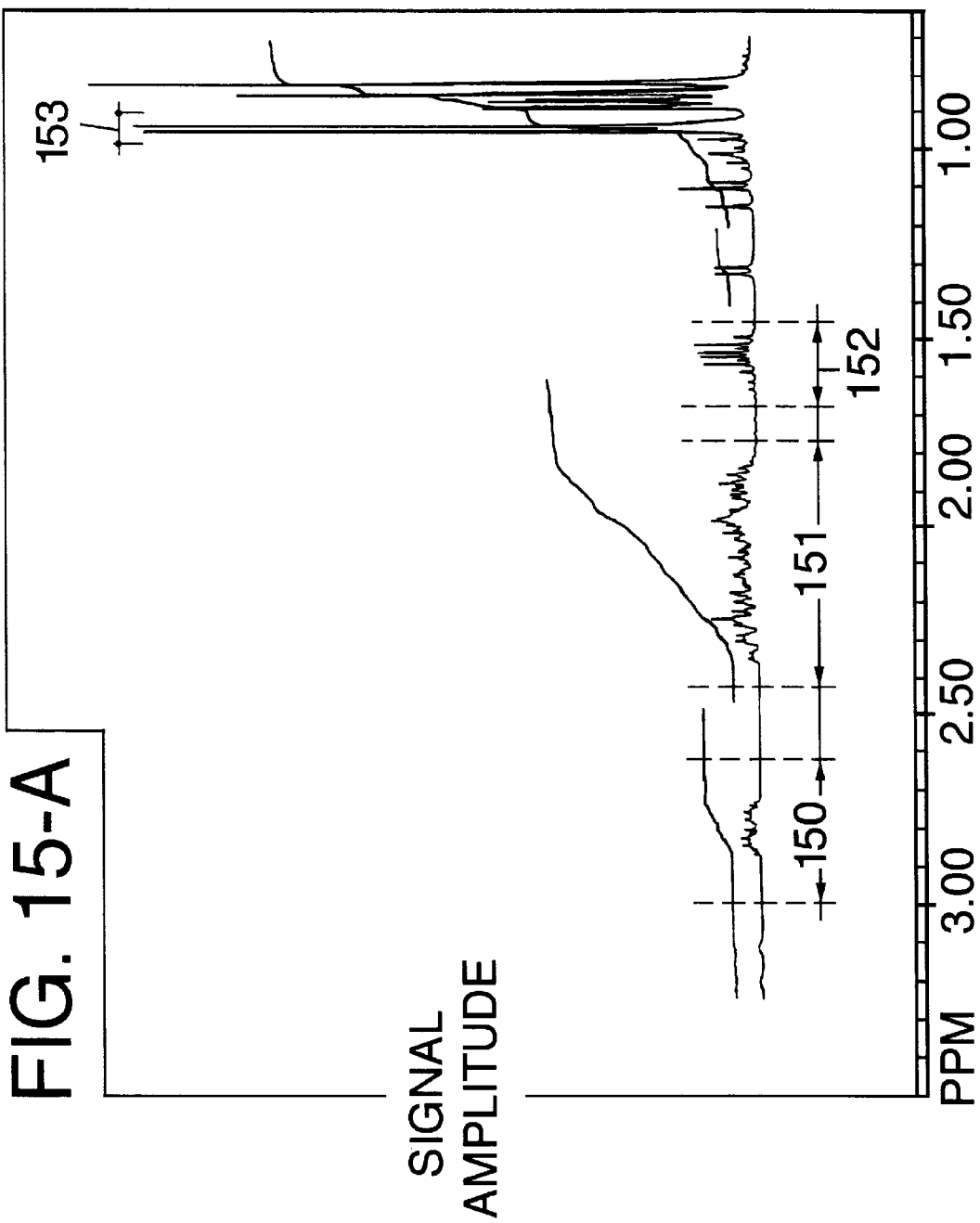

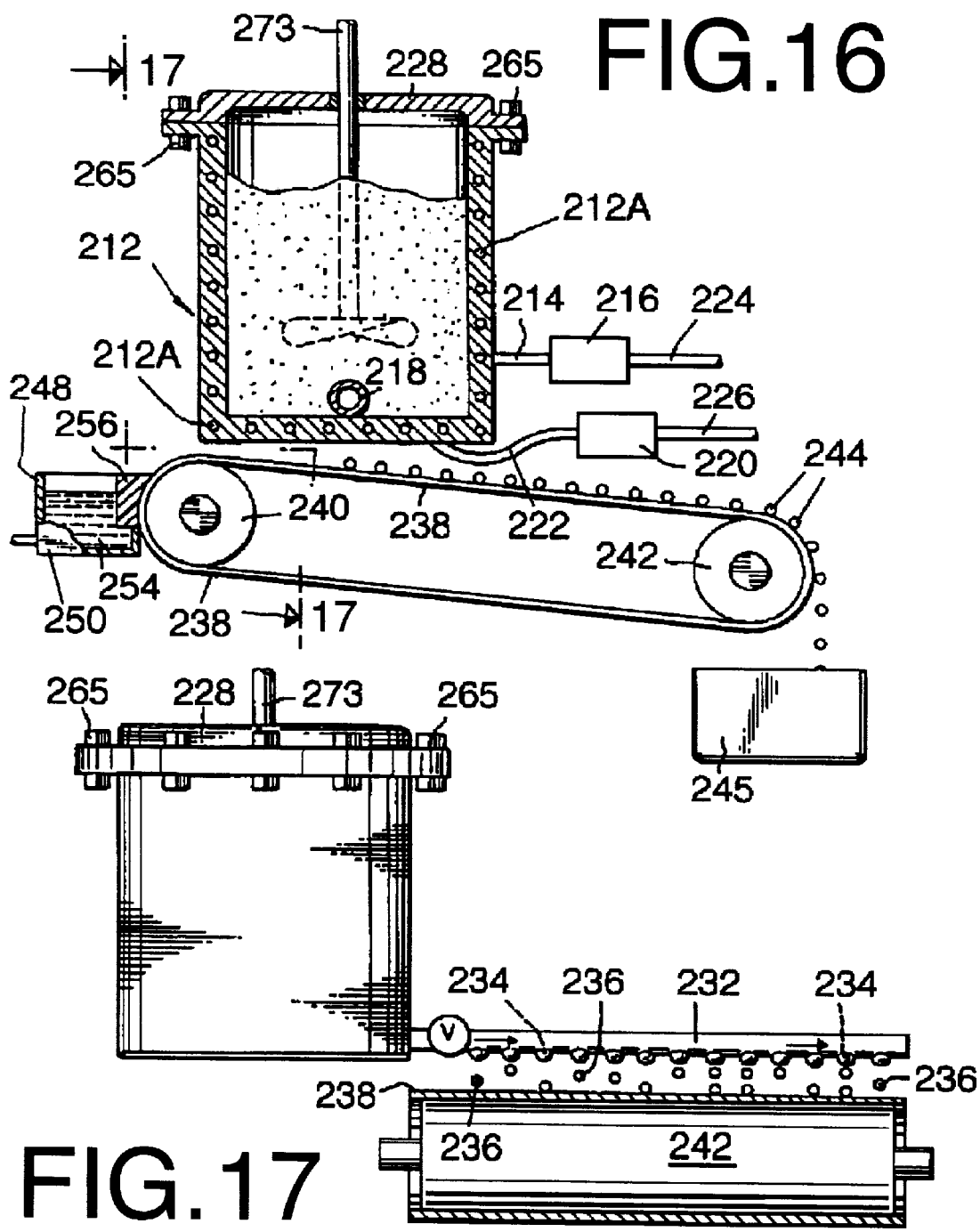

CARBON CONTAINING FUNCTIONAL GROUP SUBSTITUTED 4,5,6,7-TETRAHYDRO-POLYALKYLATED-4-INDANES, ISOMERS THEREOF, PROCESSES FOR PREPARING SAME AND USES THEREOF

BACKGROUND OF THE INVENTION

Our invention relates to pentamethyl indane derivatives, all derived from the hydrocarbon having the structure:

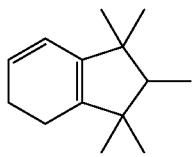

by means of first reacting such hydrocarbon with a mixture of carbon monoxide and hydrogen using an "oxo reaction catalyst" in order to form a carboxaldehyde having the structure:

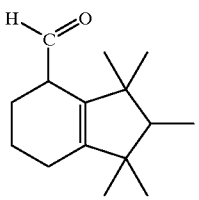

or stereoisomers thereof. Such carboxaldehydes may then be used as is for their perfumery properties or may be reacted further, for example, by means of reduction, Grignard synthesis or the like. The resultant carboxaldehydes and resultant derivatives thereof have intense and substantive and aesthetically pleasing fragrance nuances and are thus useful in the formulation of fragrance compositions.

Velvety, diffusive, sweet, rich, warm, sensual, intense musky, floral, ambery, spicy, woody, balsamic, earthy, rooty and vetiver-like aromas with sensual, animalic, powdery, creamy, costus and musky topnotes and sweet, musky, spicy and floral undertones are particularly desirable in augmenting or enhancing the aroma of perfume compositions, colognes and perfumed articles (e.g., solid or liquid anionic, cationic, nonionic or zwitterionic detergents, fabric softener compositions, fabric softener articles, hair preparations, cosmetic powders and perfumed polymers).

Compounds having the oxygen-substituted pentamethyl indane structure and pentamethyl indane hydrocarbons are known for use in perfumery. Thus, U.S. Pat. No. 3,806,472 issued on Apr. 23, 1974 discloses the use in prefumery of the compound having the structure:

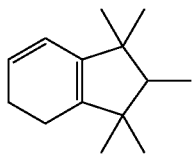

U.S. Pat. No. 3,636,165 issued on Jan. 18, 1972 discloses the perfumery utilities of the compounds having the structures:

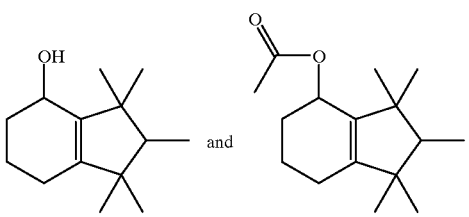

U.S. Pat. No. 3,773,836 issued on Nov. 20, 1973 discloses the perfumery use of the compound having the structure:

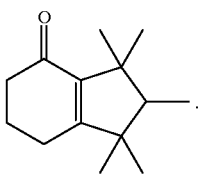

U.S. Pat. No. 4,902,840 issued on Feb. 26, 1990 discloses the perfumery use of the compound having the structure:

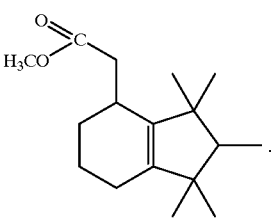

The prior art does not, however, disclose the organoleptic utilities of compounds defined according to the structure:

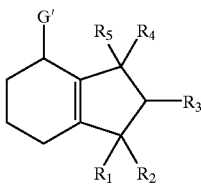

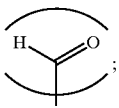

wherein G' is one of the moieties:

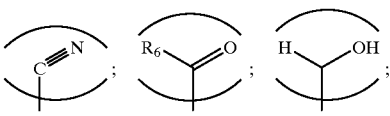

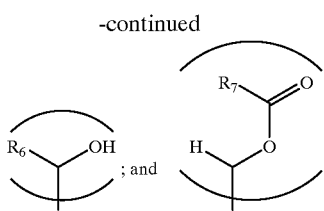

wherein $R_6$ and $R_7$ are the same or different $C_1$–$C_3$ lower alkyl and $R_1$, $R_2$, $R_4$ and $R_5$ are the same or different methyl or ethyl; and $R_3$ is hydrogen or methyl with the provisos:

(i) when $R_3$ is hydrogen, one of $R_1$, $R_2$, $R_3$ and $R_4$ is ethyl and the other of $R_1$, $R_2$, $R_3$ and $R_4$ is methyl; and (ii) when $R_3$ is methyl, then $R_1$, $R_2$, $R_3$ and $R_4$ are each methyl.

THE INVENTION

Our invention is directed to carbon containing, functional group substituted 4,5,6,7-tetrahydro-polyalkylated-4-indanes, isomers thereof and processes for preparing same, which substituted indanes are defined according to the structure:

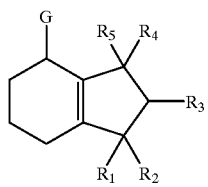

wherein G is one of the moieties:

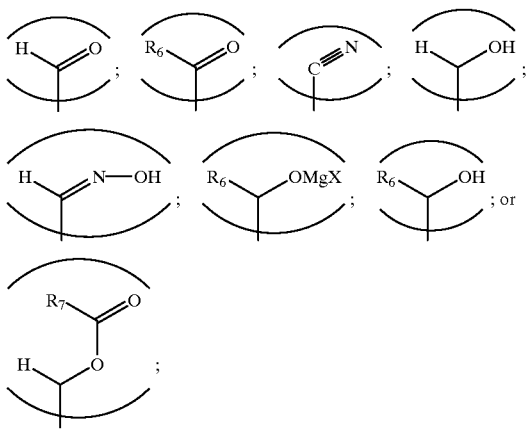

and wherein and $R_1$, $R_2$, $R_4$ and $R_5$ are the same or different methyl or ethyl; and $R_3$ is hydrogen or methyl with the provisos that:

(i) when $R_3$ is hydrogen, one of $R_1$, $R_2$, $R_4$ and $R_5$ is ethyl and the other is methyl; and (ii) when $R_3$ is methyl, then one of $R_1$, $R_2$, $R_4$ and $R_5$ is methyl; wherein $R_6$ and $R_7$ are the same or different $C_1$–$C_3$ lower alkyl; and wherein X is chloro, bromo or iodo.

Our invention is also directed to the use of 4,5,6,7-tetrahydro-polyalkylated-4-indane carbinols, carbinyl esters, carboxaldehydes, ketones and cyanides as fragrance ingredients for use in imparting, augmenting or enhancing the aroma of perfume compositions, colognes, perfumed articles and perfumed polymers. Such 4,5,6,7-tetrahydro-polyalkylated-4-indane carbinols, carbinyl esters, carboxaldehydes, ketones and cyanides are defined according to the generic structure:

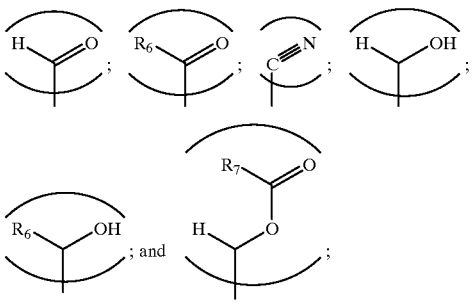

wherein G' is one of the moieties:

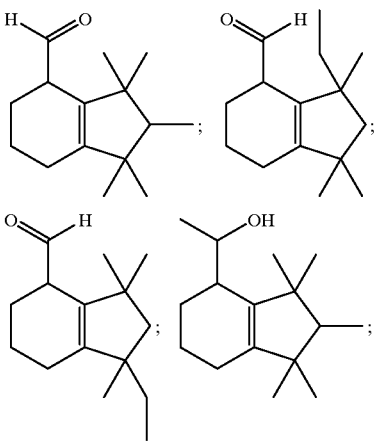

and wherein and $R_1$, $R_2$, $R_3$, $R_4$, $R_5$, $R_6$ and $R_7$ are defined, supra.

The 4,5,6,7-tetrahydro-polyalkylated-4-indane carbinols, carbinyl esters, carboxaldehydes, ketones and cyanides have velvety, diffuse, sweet, rich, warm, sensual, intense musky, floral, ambery, spicy, woody, balsamic, earthy, rooty and vetiver-like aromas with sensual, animalic, powdery, creamy, costus and musky topnotes and sweet, musky, spicy and floral undertones and impart, augment or enhance such properties to perfume compositions, colognes, perfumed articles and perfumed polymers.

Specific examples of the 4,5,6,7-tetrahydro-polyalkylated-4-indane carbinols, carbinyl esters, carboxaldehydes, ketones and cyanides of our invention have the following structures:

-continued

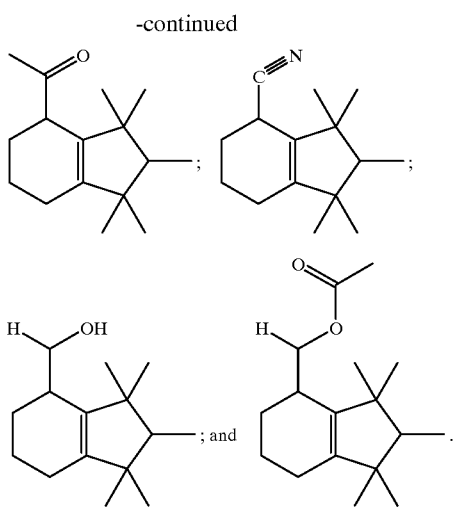
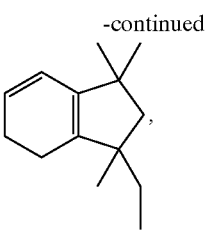
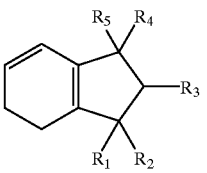

The products of our invention may exist as "cis" or "trans" stereoisomers or "cis" or "trans" racemic mixtures, for example, the materials having the structures:

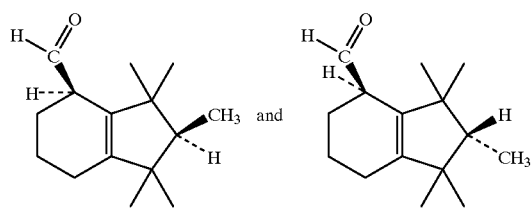

or the compounds having the structures:

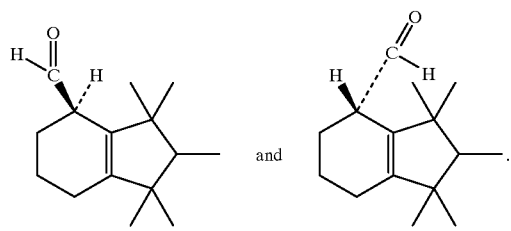

In producing the 4,5,6,7-tetrahydro-polyalkylated-4-indane carbinols, carbinyl esters, carboxaldehydes, ketones and cyanides of our invention, the starting materials are the hydrocarbons defined according to one or a mixture of the following structures:

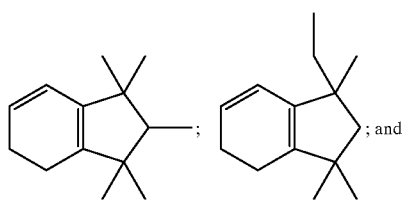

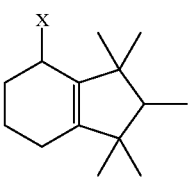

generically shown as the material having the structure:

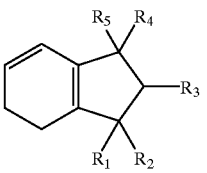

wherein $R_1$, $R_2$, $R_4$ and $R_5$ are the same or different methyl or ethyl and $R_3$ is hydrogen or methyl with the provisos:

(i) when $R_3$ is hydrogen, one of $R_1$, $R_2$, $R_4$ and $R_5$ is ethyl and the other is methyl; and (ii) when $R_3$ is methyl, one of $R_1$, $R_2$, $R_4$ and $R_5$ are each methyl.

The aforementioned hydrocarbons may be prepared by means of dehydrohalogenation or dehydration of such compounds having the generic structure:

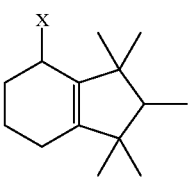

wherein X is chloro, bromo or hydroxy under conditions well known to those having ordinary skill in the art, or more specifically, dehydrohalogenation of, for example, the compound having the structure:

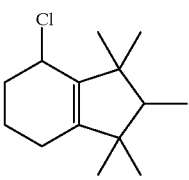

according to the reactions:

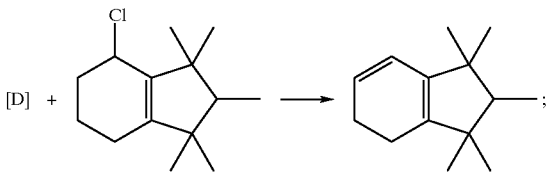

-continued

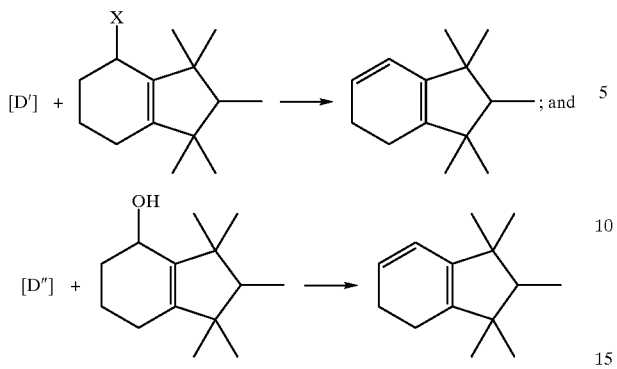

wherein D is a dehydrohalogenating agent; D' is a dehydrohalogenating agent or a dehydrating agent; and D" is a dehydrating agent.

The generic dehydrating reaction is shown thusly:

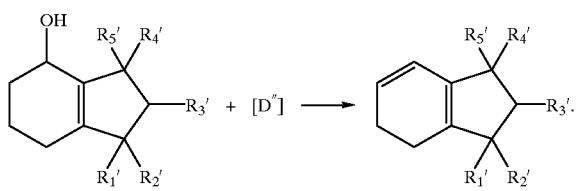

The cyclohexenol reactant is prepared by reduction of the corresponding ketone according to the reaction:

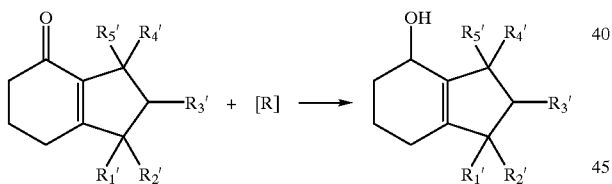

under conditions well known to those having ordinary skill in the art.

Thus, for example, a compound having the structure:

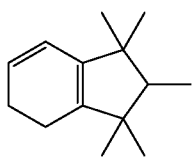

is shown to be synthesized in U.S. Pat. No. 3,806,472 issued on Apr. 23, 1974, the specification for which is incorporated by reference herein.

The compounds having the structures:

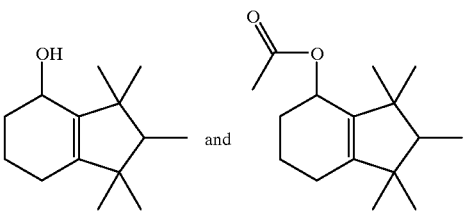

are shown to be produced in U.S. Pat. No. 3,636,165, the specification for which is incorporated by reference herein.

The compound having the structure:

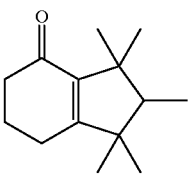

is shown to be produced according to U.S. Pat. No. 3,773,836 issued on Nov. 20, 1973, the specification for which is incorporated by reference herein.

The compound having the structure:

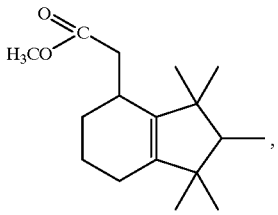

an isomer or adjacent methyl homologue of a member of the group of 4,5,6,7-tetrahydro-polyalkylated-4-indane carbinols, carbinyl esters, carboxaldehydes, ketones and cyanides of our invention is shown to be produced according to U.S. Pat. No. 4,902,840 issued on Feb. 26, 1990, the specification for which is incorporated by reference herein.

The hydrocarbons having the structure:

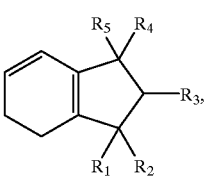

according to the processes of our invention, are then reacted with a mixture of carbon monoxide and hydrogen according to the reaction:

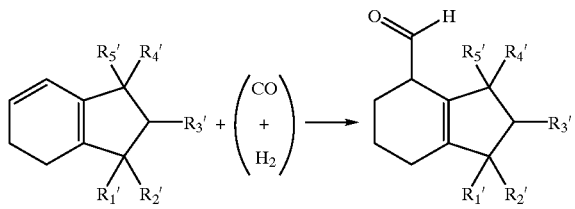

under "oxo" reaction conditions using an "oxo" reaction catalyst.

Depending upon the oxo reaction catalyst, either racemic mixtures can be formed or mixtures having a preponderance of a particular stereoisomer, are formed, for example, one of the materials having the structure:

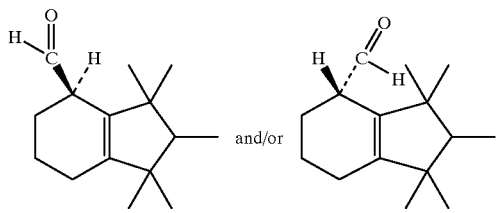

or racemic mixtures or stereoisomers of compounds having the structure:

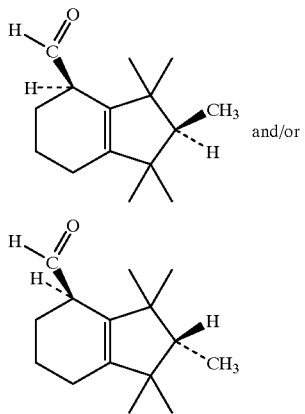

having, for example, an enantiomeric excess percent of greater than 50%, [EE%>50%].

When using an oxo reaction catalyst that will give rise to a mixture having a positive or negative optical rotation, that is a mixture of stereoisomers having an enantiomeric excess percent of greater than 50%, [EE%>50%], such oxo reaction catalysts as are set forth in Published European Application No. EP0 877,029 A2 published on Nov. 11, 1998 may be used (the specification for which is incorporated by reference herein), having for example, the structure:

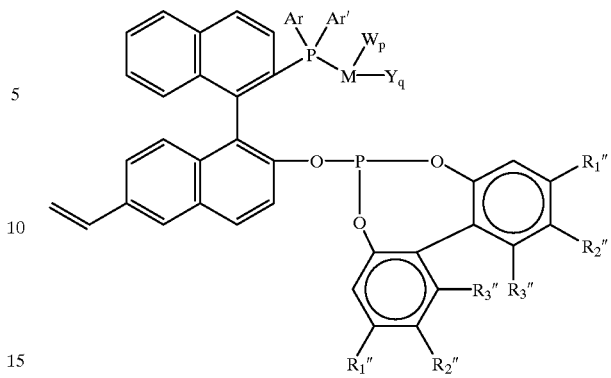

wherein Ar and Ar' represent aerial groups and wherein $R_1''$, $R_2''$ and $R_3''$ represent hydrogen or lower alkyl and wherein M represents a metal selected from the group consisting of rhodium, irridium, palladium or platinum; wherein W can be a halogen atom, acetoxy or allyl; wherein Y is a hydrogen, a halogen atom or $BF_4$ and wherein p and q are each 0 to 2; and k is an integer of from 2 up to 100. Other useful catalysts are those taught U.S. Pat. No. 5,922,918 issued on Jul. 13, 1999 entitled "METHOD FOR MAKING AN OPTICALLY ACTIVE DIPHOSPHINE LIGAND," the specification for which is incorporated by reference herein. Other useful catalysts are those set forth in Overman, Editor "ORGANIC SYNTHESES," Volume 71 (Jun. 29, 1992) at pages 1–11, the specification for which is incorporated by reference herein, showing the application of the BINAP-Ruthenium complex, for example, the complex, [(R)-2,2'-Bis (diphenylphosphino)-1,1'-binaphthyl]ruthenium(II).

Another useful oxo reaction catalyst which is also a rhodium-phosphorus complex has the structure:

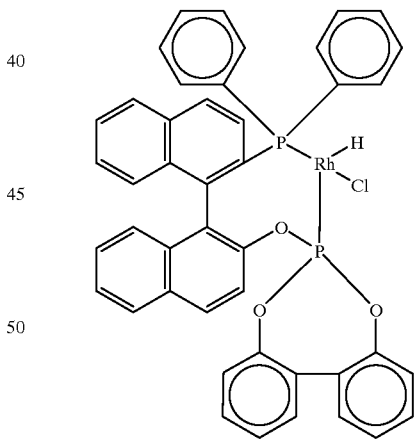

The aforementioned oxo reaction is preferably carried out under a pressure of between about 300 up to about 1,500 psig, at a temperature of between about 110 up to about 180° C., using a mixture of carbon monoxide and hydrogen having a mole ratio of carbon monoxide:hydrogen of from about 1:2 up to about 2:1, preferably 1:1. The time of reaction may vary from about 2 hours up to about 10 hours.

At the end of the reaction, the reaction mass is fractionally distilled to yield the resultant carboxaldehyde product. The resulting carboxaldehyde product may be used as is or may be further reacted, for example, using a Grignard reagent followed by hydrolysis in order to form a secondary alcohol according to the reaction sequence:

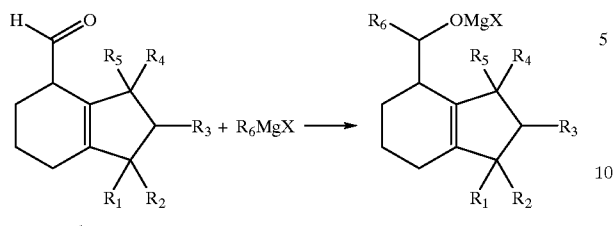

and

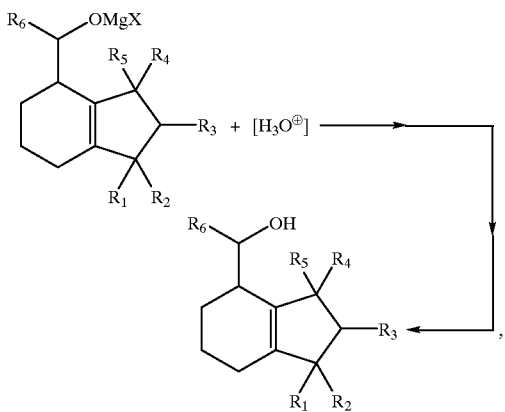

for example, the reaction:

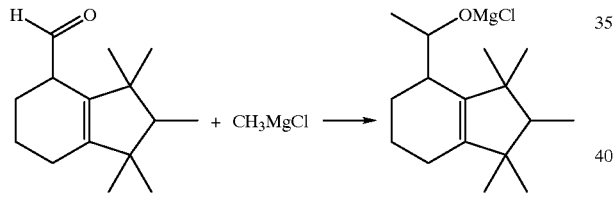

followed by the reaction:

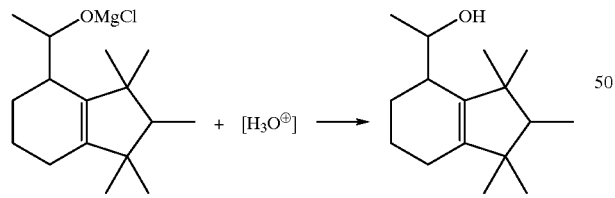

wherein $R_6$ is $C_1$–$C_3$ lower alkyl and X is chloro, bromo or iodo.

The conditions of reaction are well know to those having ordinary skill in the art and are exemplified herein, infra.

The resulting secondary alcohols defined according to the structure:

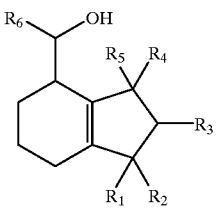

for example, the compound having the structure:

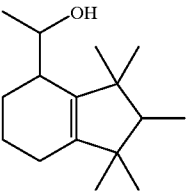

may be used "as is" or may be further reacted in order to form ethers or esters. Thus, for example, the resulting secondary alcohol can be reacted with a compound defined according to the generic structure:

wherein $R_7$ is $C_1$–$C_3$ lower alkyl and Y is oxyacyl, chloro or bromo.

In hydrolyzing the Grignard salt having the structure:

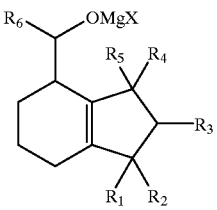

for example, the specific compound having the structure:

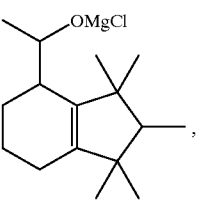

any weak acid may be utilized, for example, dilute hydrochloric acid, aqueous ammonium chloride or acetic acid. The resulting secondary alcohol having the structure:

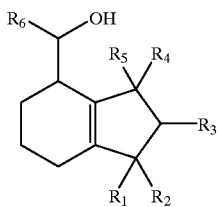

or, more specifically, the alcohol having the structure:

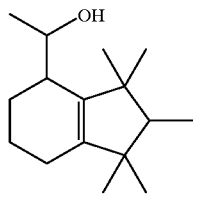

or stereoisomers thereof may be further oxidized to form ketones having the generic structure:

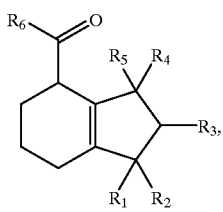

more specifically for example, the compound having the structure:

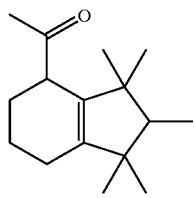

according to the reaction:

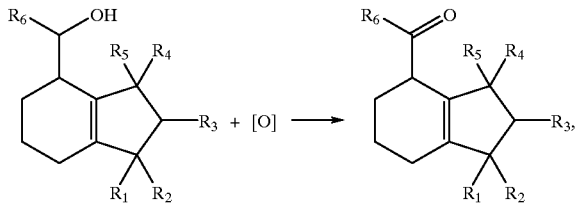

more specifically, the reaction:

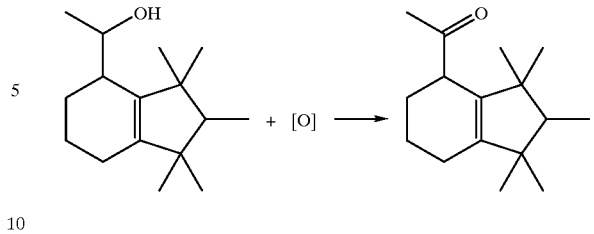

wherein [O] an oxidizing agent well known to those having ordinary skill in the art, for example, sodium dichromate, potassium permanganate or a mixture of sodium dichromate and sulfuric acid. The conditions of reaction are well known to those having ordinary skill in the art and exemplified herein in Example VIII, infra.

In the alternative, the resultant aldehydes defined according to the structure:

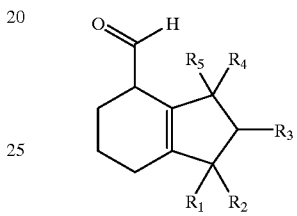

may be converted into corresponding nitriles having the generic structure:

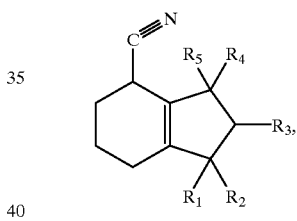

for example, the compound having the structure:

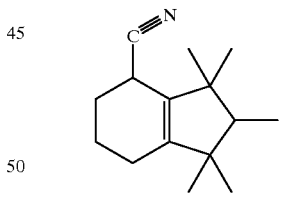

by first forming the hydroxyl imine having the generic structure:

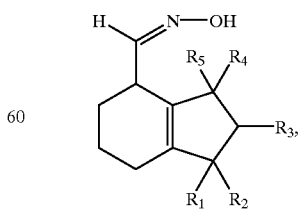

more specifically, for example, the compound having the structure:

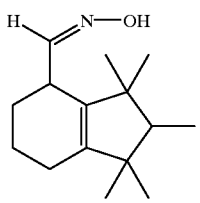

according to the generic reaction sequence:

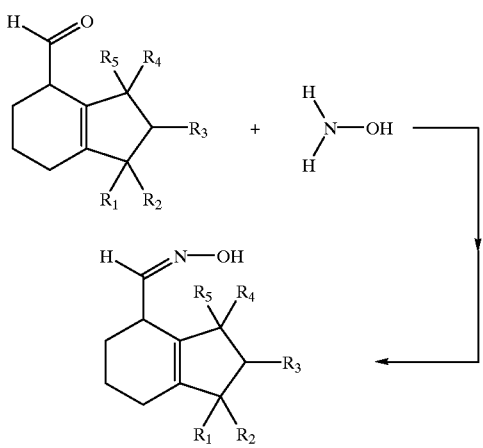

; and

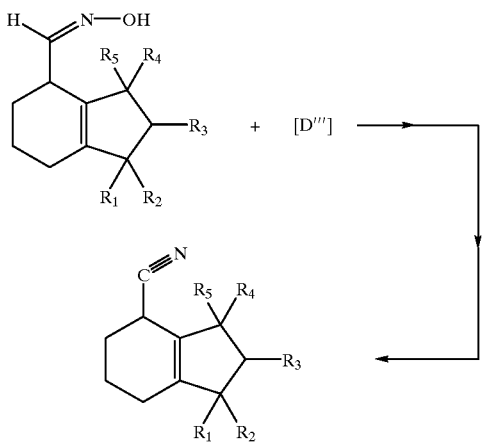

wherein [D'''] is a dehydrating agent, for example, a mixture of ferrous gluconate and acetic anhydride, as exemplified in Example XI, infra. The reaction with hydroxyl imine is carried out at a temperature of between about 50 up to about 70° C. at atmospheric pressure. The dehydration reaction is carried out under reflux conditions, e.g., 130–150 C. at atmospheric pressure for a time period of between about 1 up to about 5 hours. At the end of the reaction, the resulting nitrile is fractionally distilled.

In the alternative, the resulting carboxaldehyde defined according to the structure:

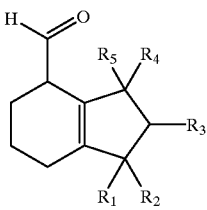

may be reduced to form the primary alcohol having the generic structure:

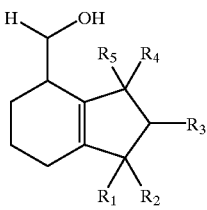

using a reducing agent such as sodium chlorohydride, more specifically, for example, the primary alcohol having the structure:

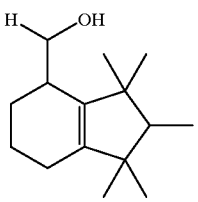

according to the generic reaction:

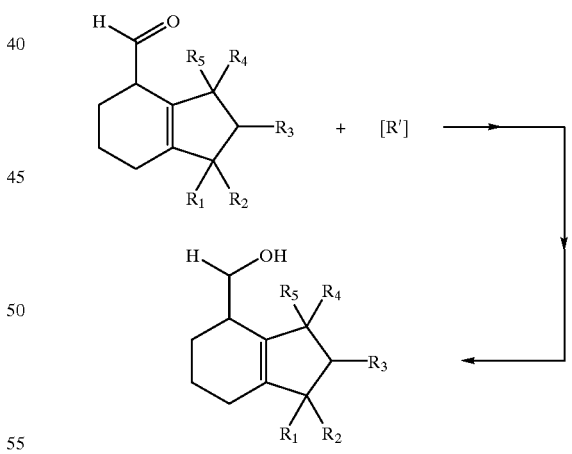

more specifically, for example, the reaction:

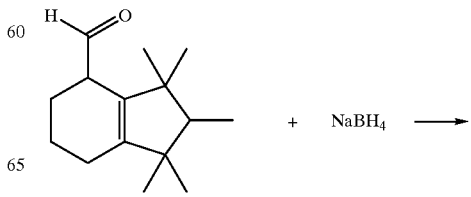

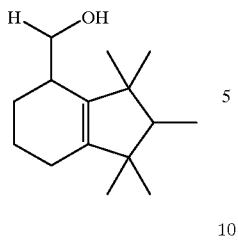

The reduction reaction is carried out under conditions well known to those having ordinary skill in the art using reducing agents well known to those having ordinary skill in the art, for example, sodium borohydride. The reduction reaction is preferably carried out in the presence of a solvent such as isopropyl alcohol under reflux conditions. At the end of the reaction, the reaction mass is neutralized and then fractionally distilled to yield the resulting primary alcohol which may be used as is for its organoleptic properties; or the primary alcohol may be further reacted, for example, to form esters according to the generic reaction:

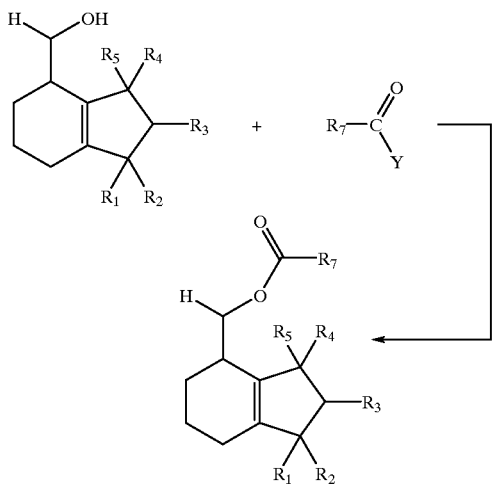

wherein $R_7$ is $C_1$–$C_3$ lower alkyl and wherein Y represents oxyacyl, chloro or bromo; more specifically, for example, according to the reaction:

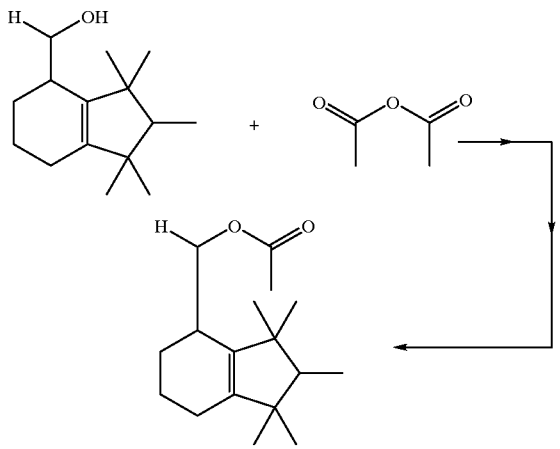

Such esterification reactions in order to form esters defined according to the generic structure:

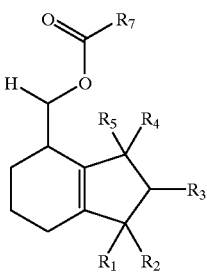

or, more specifically, for example, the compound having the structure

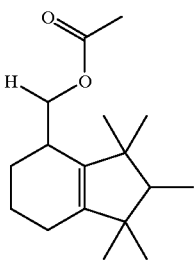

are carried out under conditions well known to those having ordinary skill in the art; for example, as exemplified in Example X, infra, using an acetic anhydride reagent under reflux conditions (approximately 110° C.) for a period of time of between about 0.5 hours up to about 3 hours. At the end of the reaction, the reaction mass is neutralized with, for example, aqueous sodium carbonate, and the resulting product is dried and fractionally distilled. The resulting ester defined according to the structure:

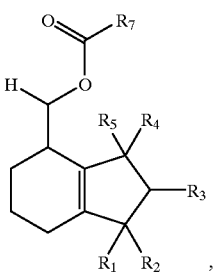

more specifically, for example, defined according to the structure:

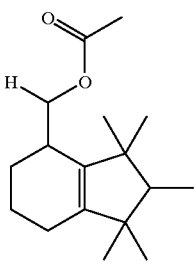

may then be used as is for its organoleptic properties or further reacted by means of transesterification whereby the ester moiety is replaced with a different ester moiety totally or in part (for example, whereby a mixture of acetate and butyrate esters is formed). The transesterification conditions are well known to those having ordinary skill in the art.

If the initial oxo reaction is carried out whereby a mixture of stereoisomers or a stereoisomer having an enantiomeric excess of greater than 50%, [EE%>50%], for example having an enantiomeric excess percent of 90%, [EE%= 90%], then the resulting reaction products as set forth, supra, will have the same enantiomeric excess and will have the same specific optical rotation.

The trans:cis mixture of compounds having the structures:

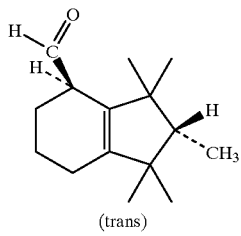

(trans)

and

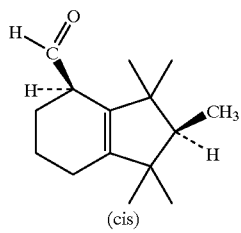

(cis)

in a 9:1 ratio, has a velvety, diffusive, sweet, rich, warm, intense musk, spicy, woody, balsamic, earthy, rooty and vetiver-like aroma with animalic, costus topnotes and sweet, musky, spicy, floral undertones.

At least one of the 4,5,6,7-tetrahydro-polyalkylated-4-indane carbinols, carbinyl esters, carboxaldehydes, ketones and cyanides of our invention and one or more auxiliary perfume ingredients, including for example, alcohols (other than the alcohols of our invention), aldehydes (other than the aldehydes of our invention), ketones (other than the ketones of our invention), terpenic hydrocarbons, esters (other than the esters of our invention), lactones, ethers, nitriles (other than the nitrites of our invention), natural essential oils and synthetic oils may be admixed so that the combined odors of the individual components produce a pleasant and desired fragrance, particularly and preferably in the pine fragrance area. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling, fresh smelling materials.

In perfume compositions, it is the individual components which contribute to their particular olfactory characteristics, however, the overall sensory effect of the perfume composition will be at least the sum total of the effects of each of the ingredients. Thus, at least one of the 4,5,6,7-tetrahydro-polyalkylated-4-indane carbinols, carbinyl esters, carboxaldehydes, ketones and cyanides of our invention modify or enhance the aroma characteristics of a perfume composition, for example, by utilizing or moderating the olfactory reaction contributed by another ingredient in the composition.

The amount one or more of the 4,5,6,7-tetrahydro-polyalkylated-4-indane carbinols, carbinyl esters, carboxaldehydes, ketones and cyanides of our invention which will be effective in the perfume composition as well as in the perfumed articles and colognes depends on many factors, including the other ingredients, their amounts and the effects which are desired. It has been found that perfume compositions that contain as little as 0.01% of at least one of the 4,5,6,7-tetrahydro-polyalkylated-4-indane carbinols, carbinyl esters, carboxaldehydes, ketones and cyanides of our invention or even less (e.g., 0.005%) can be used to impart, augment or enhance velvety, diffusive, sweet, rich, warm, sensual, intense musky, floral, ambery, spicy, woody, balsamic, earthy, rooty and vetiver-like aromas with sensual, animalic, powdery, creamy, costus and musky topnotes and sweet, musky, spicy, floral undertones in and to soaps, cosmetics, solid or liquid anionic, cationic, nonionic or zwitterionic detergents, fabric softener compositions, fabric softener articles, hair preparations and perfumed polymers. The amount employed can range up to 70% of the fragrance components and will depend on considerations of cost, nature of the end product, the effect desired on the finished product and the particular fragrance sought.

One or more of the 4,5,6,7-tetrahydro-polyalkylated-4-indane carbinols, carbinyl esters, carboxaldehydes, ketones and cyanides of our invention are useful (taken alone or together with other ingredients in the perfume composition) as (an) olfactory component(s) in detergents and soaps, space odorants and deodorants, perfumes, colognes, toilet water, bath preparations such as creams, deodorants, hand lotions and sun screens; powders such as talcs, dusting powders, face powders and the like. When used as (an) olfactory component(s) as little as 1% of at least one of the 4,5,6,7-tetrahydro-polyalkylated-4-indane carbinols, carbinyl esters, carboxaldehydes, ketones and cyanides of our invention will suffice to impart intense and substantive velvety, diffusive, sweet, rich, warm, sensual, intense musky, floral, ambery, spicy, woody, balsamic, earthy, rooty and vetiver-like aromas with sensual, animalic, powdery, creamy, costus and musky topnotes and sweet, musky, spicy, floral undertones particularly to musk and pine formulations. Generally no more than 20% of at least one of the 4,5,6,7-tetrahydro-polyalkylated-4-indane carbinols, carbinyl esters, carboxaldehydes, ketones and/or cyanides of our invention based on the ultimate end product is required in the perfume composition.

Accordingly, in perfume compositions and colognes from about 0.01% up to about 70% of the perfume composition may be at least one of the 4,5,6,7-tetrahydro-polyalkylated-4-indane carbinols, carbinyl esters, carboxaldehydes, ketones and cyanides of our invention.

In perfumed articles, the quantity of at least one of the 4,5,6,7-tetrahydro-polyalkylated-4-indane carbinols, carbinyl esters, carboxaldehydes, ketones and cyanides of our invention may vary from about 0.005% up to about 25% by weight of the perfumed article; and from about 8% in the case of solid or liquid anionic, cationic, nonionic or zwitterionic detergents, for example.

In addition, the perfume composition or fragrance composition of our invention can contain a vehicle or carrier for at least one of the 4,5,6,7-tetrahydro-polyalkylated-4-indane carbinols, carbinyl esters, carboxaldehydes, ketones and cyanides of our invention. The vehicle can be a liquid such as a nontoxic alcohol such as ethyl alcohol or a nontoxic glycol such as propylene glycol or the like. The carrier can also be an absorbent solid such as a gum (e.g., gum arabic, xanthan gum or guar gum or mixtures of same) or components for encapsulating the composition (such as gelatin as by means of coacervation or such as a urea-formaldehyde prepolymer when a polymeric wall is intended to be formed around a liquid perfume composition center).

BRIEF DESCRIPTION OF THE DRAWINGS

FIG. 1A is a GC capillary column survey for the reaction product of Example II containing the compounds having the structures:

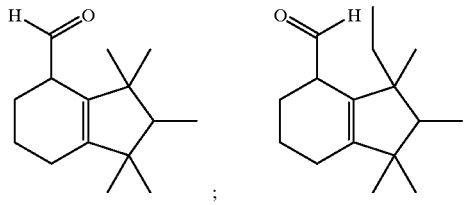

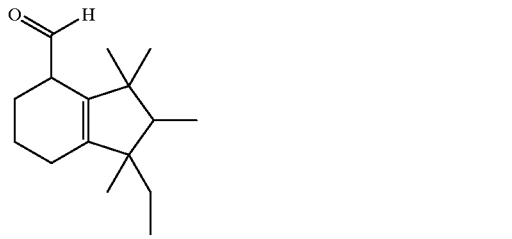

including the 9:1 trans:cis mixture of the compound having the structure:

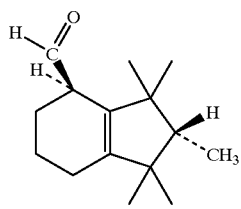

and the compound having the structure:

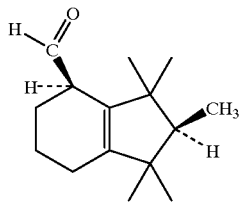

(conditions: 50 meter×0.32 mm CARBOWAX® 20M/bonded fused silica column programmed from 75° C. up to 250° C. at 2° C. per minute).

FIG. 1B is a GC capillary column survey for the reaction product of Example II containing the compounds having the structures:

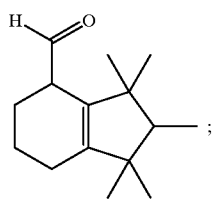

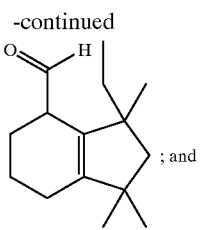

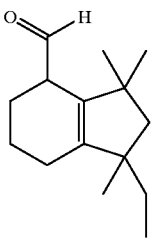

including the 9:1 trans:cis mixture of the compound having the structure:

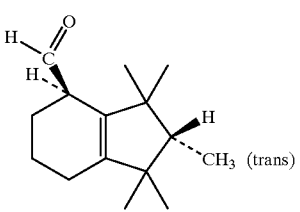

and the compound having the structure:

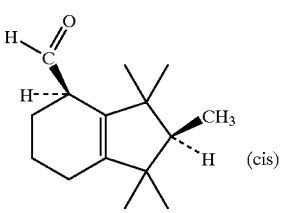

(conditions: 50 meter×0.32 mm CARBOWAX® 20M/bonded fused silica column programmed from 75° C. up to 250° C. at 2° C. per minute).

FIG. 2 is the NMR spectrum for distillation fraction No. 22 of the distillation of the reaction product of Example II containing the mixture of trans:cis (9:1) compounds having the structures:

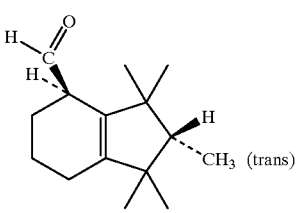

and the compound having the structure:

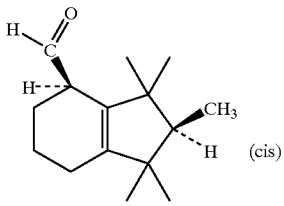

(cis)

FIG. 2A is an enlargement of section "A" of the NMR spectrum of FIG. 2.

FIG. 2B is an enlargement of the section "B" of the NMR spectrum of FIG. 2.

FIG. 2C is an enlargement of the section "C" of the NMR spectrum of FIG. 2.

Figure 3:
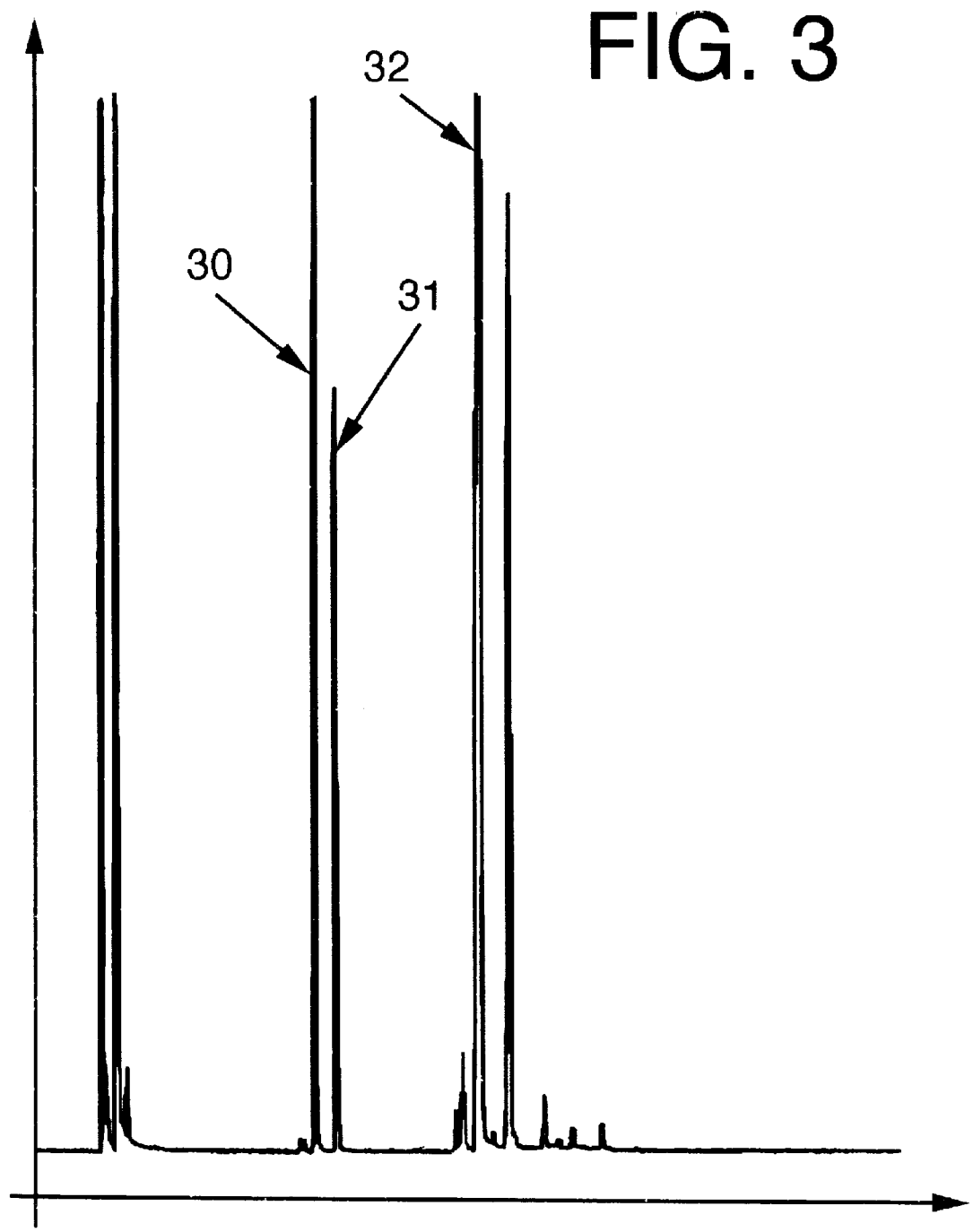

FIG. 3 is a GC capillary column profile for the reaction product of Example III containing the compounds having the structures:

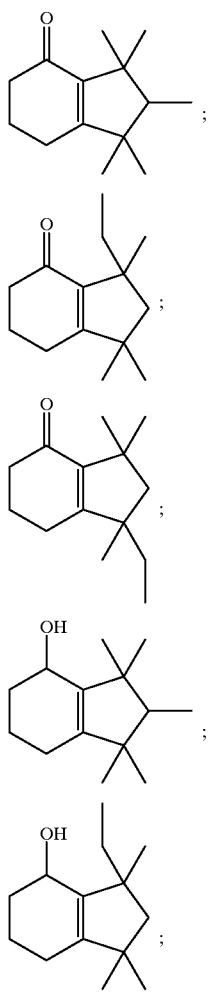

-continued

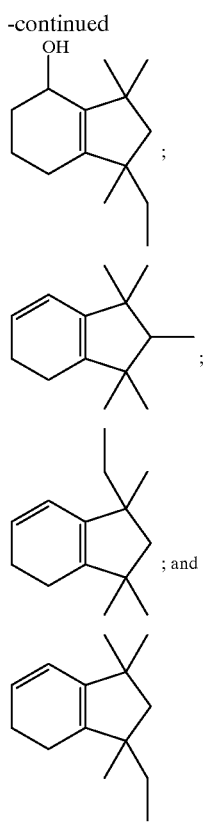

(conditions: 50×0.32 mm OV-1/bonded fused silica column programmed from 75° C. up to 250° C. at 2° C. per minute).

Figure 4:
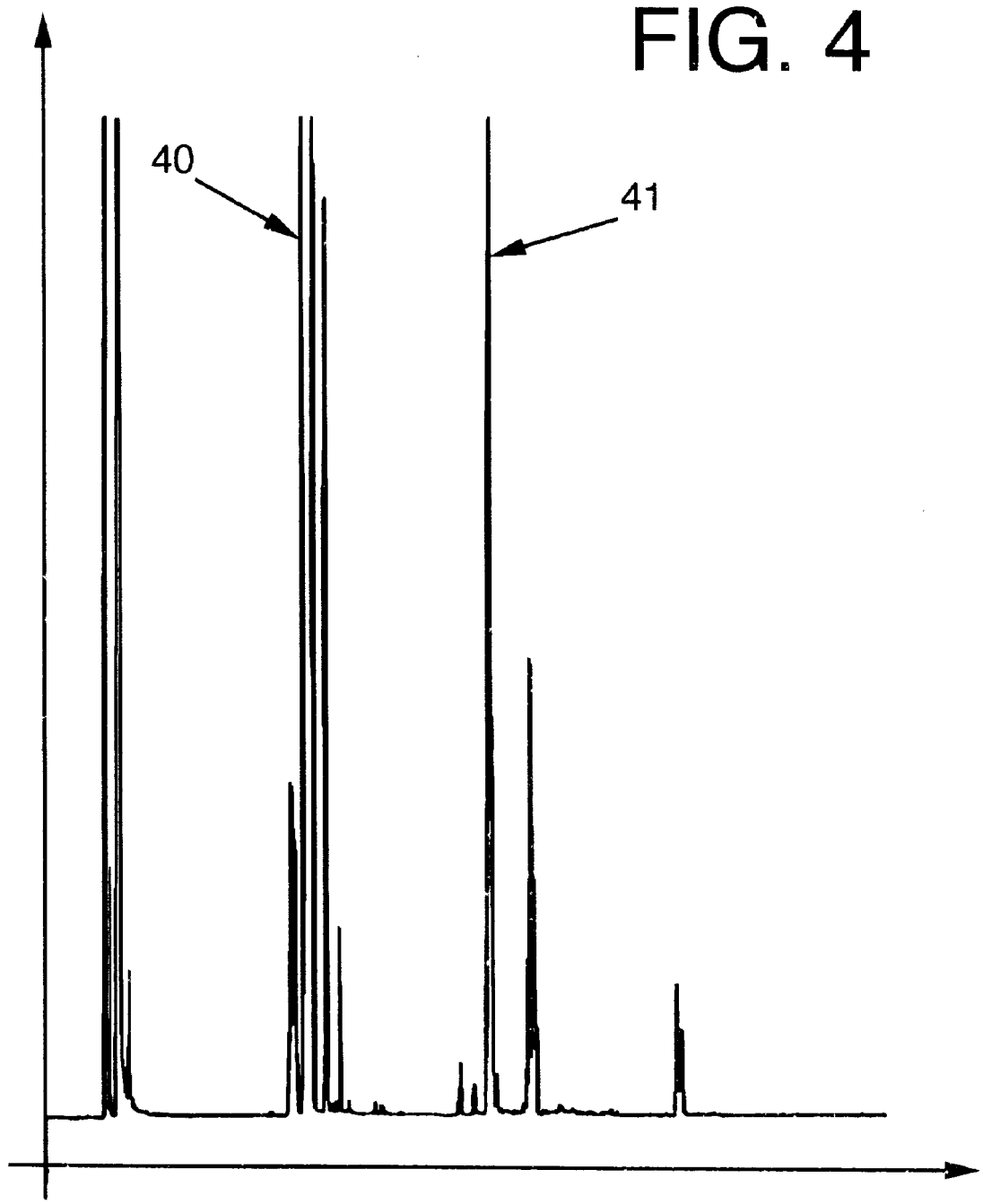

FIG. 4 is a GC capillary profile the reaction product of Example V containing the compounds having the structures:

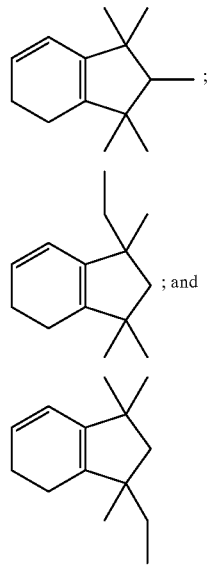

(conditions: 50 meter×0.32 mm OV-1/bonded fused silica column programmed from 75° C. up to 250° C. at 2° C. per minute).

FIG. 5A is a GC capillary column survey for the reaction product of Example VI containing the compounds having the structures:

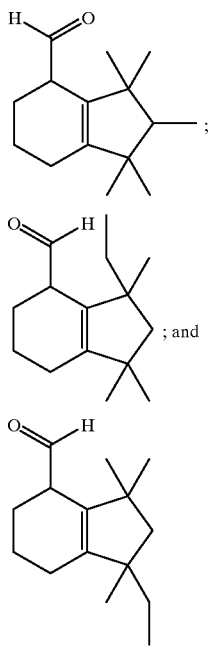

(conditions: 50 meter×0.32 mm methyl silicone/fused silica column programmed from 75° C. up to 250° C. at 2° C. per minute).

FIG. 5B is a GC capillary column survey for the reaction product of Example VI containing the compounds having the structures:

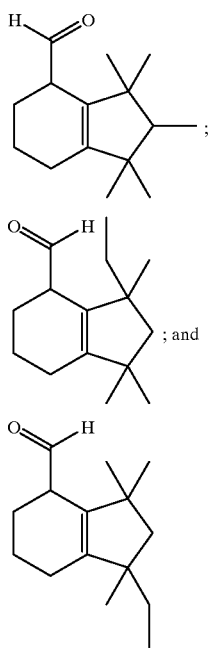

(conditions: 50 meter×0.32 mm CARBOWAX® 20M/ bonded fused silica column programmed from 75° C. up to 250° C. at 2° C. per minute).

FIG. 6A is a GC capillary column survey for the reaction product of Example VII containing the compound having the structure:

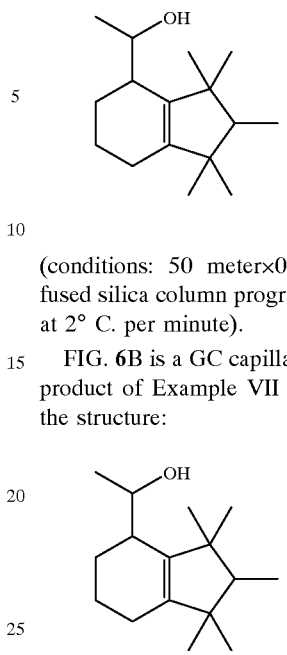

(conditions: 50 meter×0.32 mm methyl silicone/bonded fused silica column programmed from 75° C. up to 250° C. at 2° C. per minute).

FIG. 6B is a GC capillary column survey for the reaction product of Example VII containing the compound having the structure:

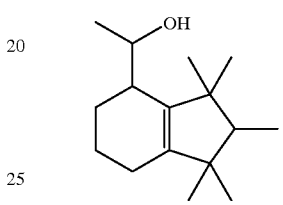

(conditions: 50 meter×0.32 mm CARBOWAX® 20M/ bonded fused silica column programmed from 75° C. up to 250° C. at 2° C. per minute).

FIG. 7 is the NMR spectrum for the compound having the structure:

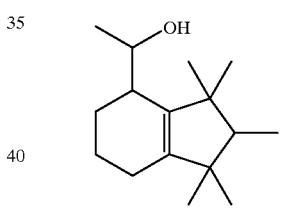

prepared according to Example VII.

FIG. 7A is an enlargement of section "A" of the NMR spectrum of FIG. 7.

FIG. 8A is a GC capillary column survey for the reaction product of Example VIII containing the compound having the structure:

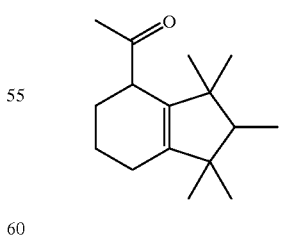

(conditions: 50 meter×0.32 mm methyl silicone/bonded fused silica column programmed from 75° C. up to 250° C. at 2° C. per minute).

FIG. 8B is a GC capillary column survey for the reaction product of Example VIII containing the structure:

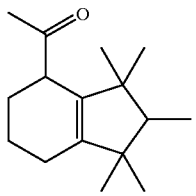

(conditions: 50 meter×0.32 mm CARBOWAX® 20M/bonded fused silica column programmed from 75° C. up to 250° C. at 2° C. per minute).

Figure 9:
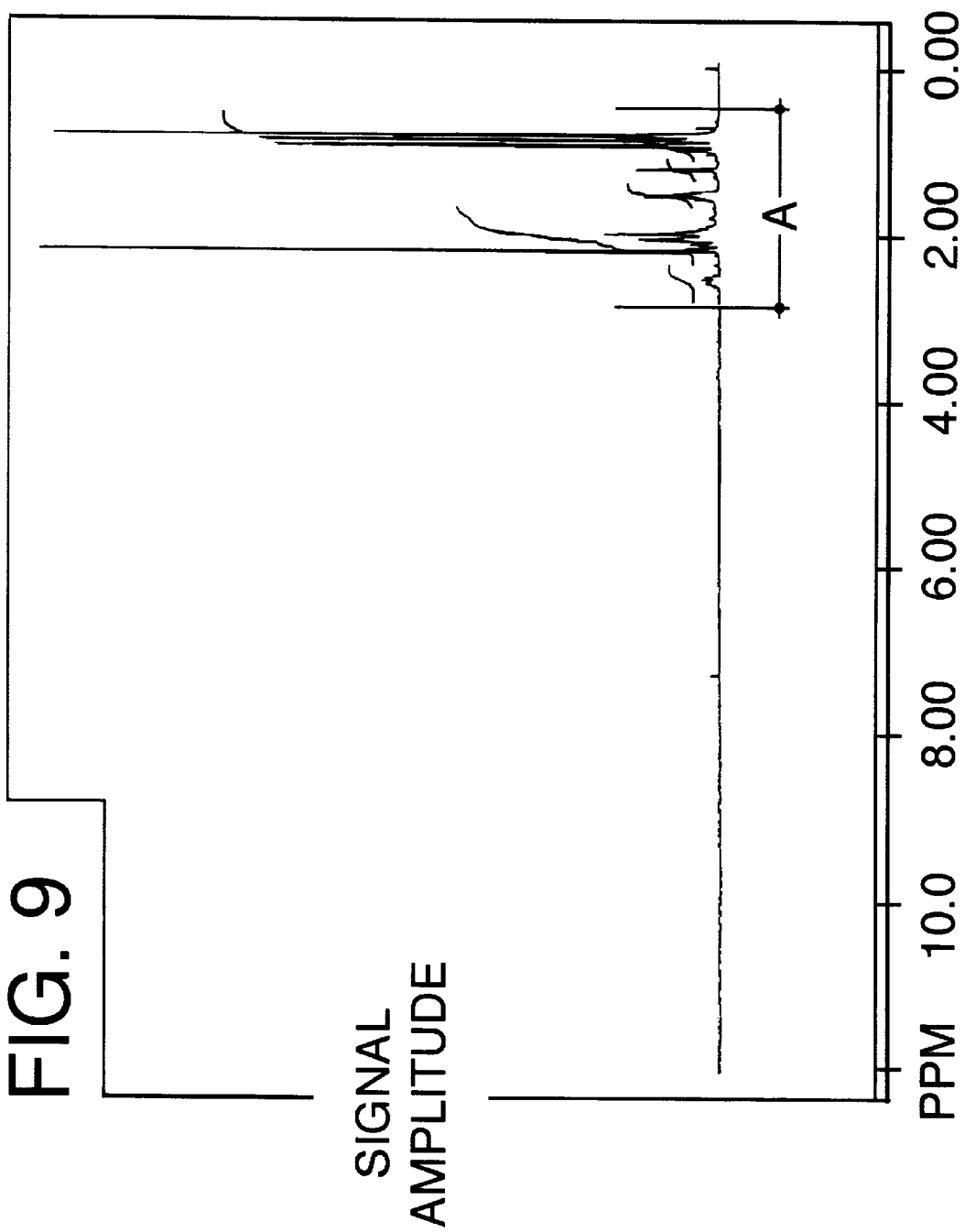

FIG. 9 is the NMR spectrum for the compound having the structure:

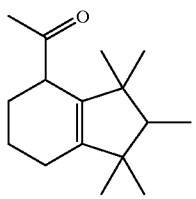

prepared According to Example VIII.

FIG. 9A is an enlargement of the section "A" of the NMR spectrum of FIG. 9.

FIG. 10A is a GC capillary column survey for the reaction product of Example IX containing the compound having the structure:

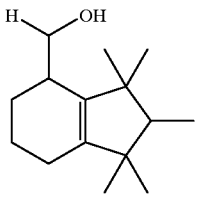

(conditions: 50 meter×0.32 mm methyl silicone/bonded fused silica column programmed from 75° C. up to 250° C. at 2° C. per minute).

FIG. 10B is a GC capillary column survey for the reaction product of Example IX containing the compound having the structure:

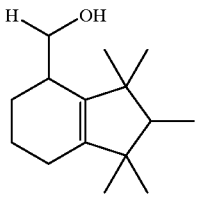

(conditions: 50 meter×0.32 mm CARBOWAX® 20M/bonded fused silica column programmed from 75° C. up to 250° C. at 2° C. per minute).

FIG. 11 is the NMR spectrum for the compound having the structure:

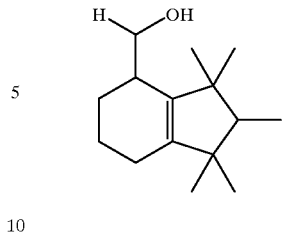

prepared according to Example IX.

FIG. 11A is an enlargement of the section "A" of the NMR spectrum of FIG. 11.

FIG 12A is a GC capillary column survey for the reaction product of Example X containing the compound having the structure:

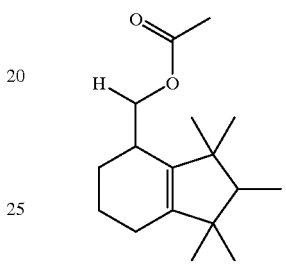

(conditions: 50 meter×0.32 mm methyl silicone/bonded fused silica column programmed from 75° C. up to 250° C. at 2° C. per minute).

FIG. 12B is a GC capillary column survey for the reaction product of Example X containing the compound having the structure:

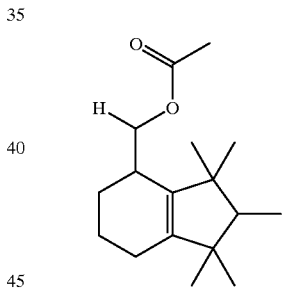

(conditions: 50 meter×0.32 mm CARBOWAX® 20M/bonded fused silica column programmed from 75° C. up to 250° C. at 2° C. per minute).

FIG. 13 is an NMR spectrum for the compound having the structure:

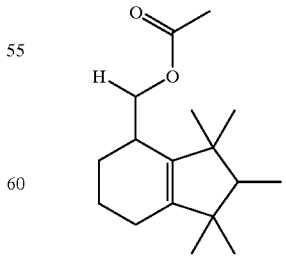

prepared according to Example X.

FIG. 13A is an enlargement of section "A" of the NMR spectrum of FIG. 13.

FIG. 14A is a GC capillary column survey for the reaction product of Example XI containing the compound having the structure:

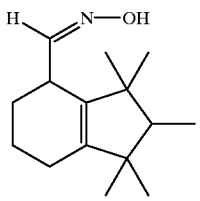

(conditions: 50 meter×0.32 mm methyl silicone/bonded fused silica column programmed from 75° C. up to 250° C. at 2° C. per minute).

FIG. 14B is a GC capillary column survey for the reaction product of Example XI containing the compound having the structure:

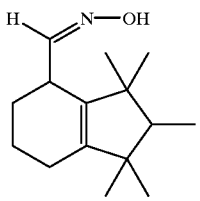

(conditions: 50 meter×0.32 mm CARBOWAX® 20M/ bonded fused silica column programmed from 75° C. up to 250° C. at 2° C. per minute).

FIG. 14C is a is a GC capillary column survey for the reaction product of Example XI containing the compound having the structure:

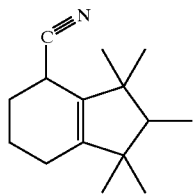

(conditions: 50 meter×0.32 mm methyl silicone/bonded fused silica column programmed from 75° C. up to 250° C. at 2° C. per minute).

FIG. 14D is a GC capillary column survey for the reaction product of Example XI containing the compound having the structure:

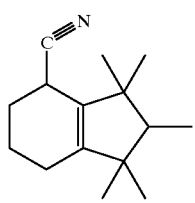

(conditions: 50 meter×0.32 mm CARBOWAX® 20M/ bonded fused silica column programmed from 75° C. up to 250° C. at 2° C. per minute).

FIG. 15 is the NMR spectrum for the compounds having the structures:

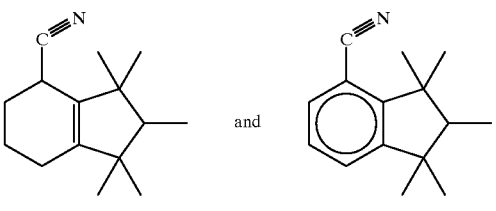

prepared according to Example XI.

FIG. 15A is an enlargement of section "A" of the NMR spectrum of FIG. 15.

FIG. 16 is a partial side elevation and partial sectional view of an apparatus for forming polymer pellets scented with one of the perfume compositions or perfumery materials of our invention containing at least one of the 4,5,6,7-tetrahydro-polyalkylated-4-indane carbinols, carbinyl esters, carboxaldehydes, ketones and cyanides of our invention.

FIG. 17 is a section taken on line 17—17 of FIG. 16.

DETAILED DESCRIPTION OF THE DRAWINGS

Referring to FIG. 1A, the GC capillary column survey for Example II, the peak indicated by reference numeral 10 is the peak for the mixture of cis and trans isomers having the structures:

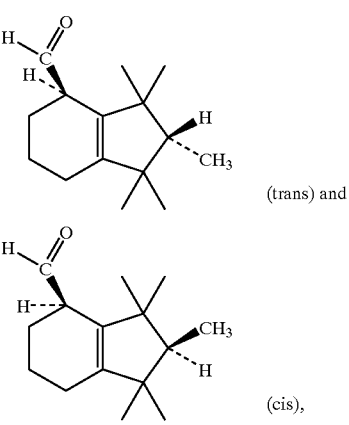

the ratio of trans:cis isomers being 9:1.

Referring to FIG. 3, the GC capillary column profile for the reaction product of Example III, the peaks indicated by reference numerals 30 and 31 are for the hydrocarbons defined according to the structures:

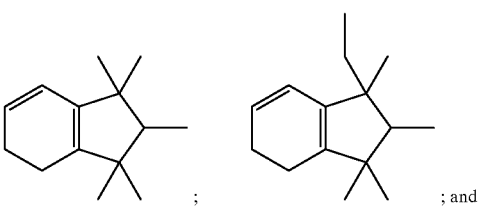

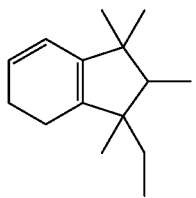

The peak indicated by reference numeral 32 is the peak for the mixture of compounds having the structures:

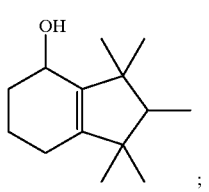 ; 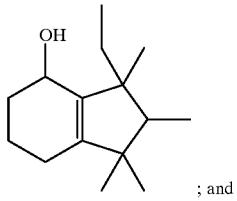 ; and

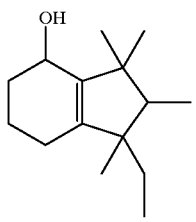 .

Referring to FIG. 4, the GC capillary column profile for the reaction product of Example V, the peak indicated by reference numeral 40 is for the mixture of compounds having the structures:

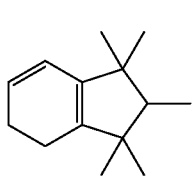 ; 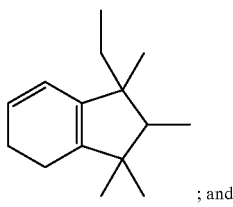 ; and

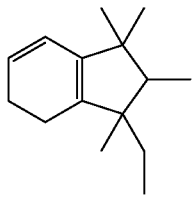 .

The peak indicated by reference numeral 41 is the peak for the mixture of compounds having the structures:

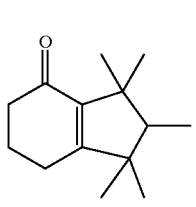 ; 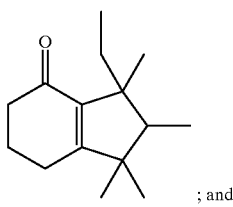 ; and

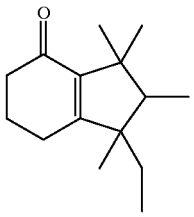

FIG. 7A is the NMR spectrum for the compound having the structure:

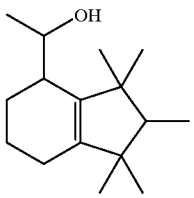 , the peaks indicated by reference numeral 70 are the peaks for the moiety having the structure:

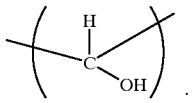 .

The peaks indicated by reference numerals 71 and 72 are for the moiety having the structure:

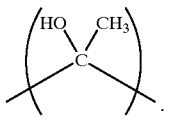 .

The peaks indicated by reference numeral 73 are for methyl groups. The peak indicated by reference numeral 74 is for methylene moieties.

Referring to FIG. 9A, part of the NMR spectrum for the reaction product of Example VIII for the compound having the structure:

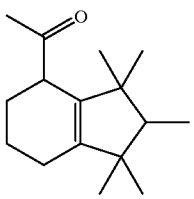 , the peak indicated by reference numeral 90 is the peak for the moiety having the structure:

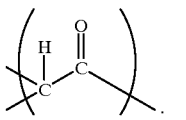 .

The peak indicated by reference numeral 91 is for the moiety having the structure:

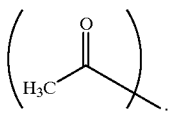

The peaks indicated by reference numeral 95 are for the moiety having the structure:

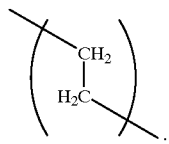

The peaks indicated by reference numeral 92 are for methylene moiety. The peaks indicated by reference numeral 93 are for the methylmethylene moiety having the structure:

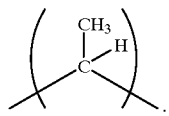

The peaks indicated by reference numeral 94 are for the gem dimethyl moiety having the structure:

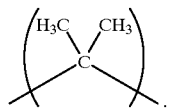

The peak indicated by reference numeral 95 is for the moiety having the structure:

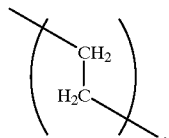

FIG. 11 is the NMR spectrum for the compound having the structure:

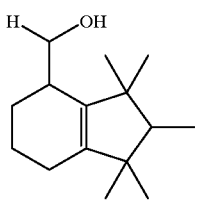

The peak indicated by reference numeral 110 is for the moiety having the structure:

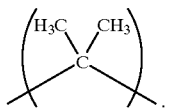

The peak indicated by reference numeral 112 is for the moiety having the structure:

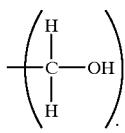

Referring to the portion of the NMR spectrum of FIG. 13A, the NMR spectrum for which is for the compound having the structure:

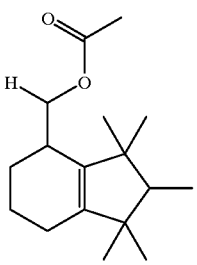

prepared according to Example X, and the peak indicated by reference numeral 134 is for the moiety having the structure:

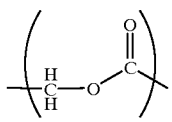

The peak indicated by reference numeral 130 is for the moiety having the structure:

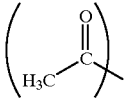

The peaks indicated by reference numeral 131 are for the moiety having the structure:

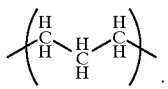

The peak indicated by reference numeral 132 are for the "gem" dimethyl moieties defined according to the structure:

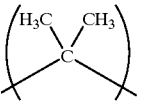

The peak indicated by reference numeral 133 is for the moiety having the structure:

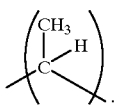

Referring to the NMR spectrum of FIG. 15 for the compounds having the structures:

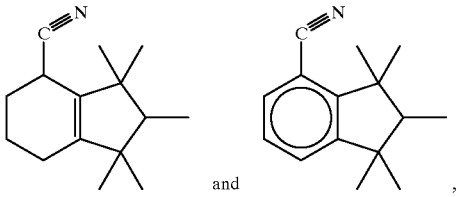

the peaks indicated by reference numeral 156 are for the compound having the structure:

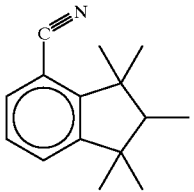

Referring to the portion of the NMR spectrum of FIG. 15, FIG. 15A, the NMR spectrum for which are for the compounds having the structures:

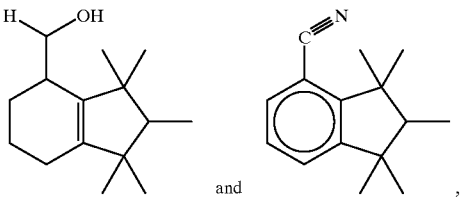

the peak indicated by reference numeral 150 is for the moiety having the structure:

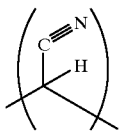

The peaks indicated by reference numeral 151 are for the moiety having the structure:

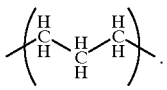

The peaks indicated by reference numeral 152 are for the moiety having the structure:

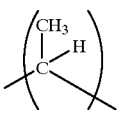

The peaks indicated by reference numeral 153 are for the "gem" dimethyl moieties having the structure:

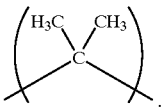

Referring to FIGS. 16 and 17, the apparatus used in producing polymeric fragrances containing at least one of the 4,5,6,7-tetrahydro-polyalkylated-4-indane carbinols, carbinyl esters, carboxaldehydes, ketones and cyanides of our invention comprises a device for forming scented polyolefin (for example) pellets which comprises a vat or container 212 into which a mixture of polyolefins such as polyethylene or a aromatic substance or scented material containing or consisting of at least one of the 4,5,6,7-tetrahydro-polyalkylated-4-indane carbinols, carbinyl esters, carboxaldehydes, ketones and cyanides of our invention is placed. The container is closed by an airtight lid 228 and clamped to the container by bolts 265. A stirrer 273 traverses the lid or cover 228 in an airtight manner and is rotated in a suitable manner. A surrounding cylinder 212 having heating coils which are supplied with electric current through cable 224 from a rheostat or control 216 is operated to maintain the temperature inside the container 212 such that polyethylene r other thermoplastic polymer in the container will be maintained in the molten or liquid state. It has been found advantageous to employ a colorless, odorless polymer (e.g., polyethylene) with a viscosity ranging between 180 and 220 Saybolt seconds and having a melting point in the range of 220–280° F. The heater 212A is operated to maintain the upper portion of the container 212 within a temperature range of from 250–250° F. The bottom portion of the container 212 is heated by means of heating coils 212A heated through a control 220 connected thereto through a connecting wire 226 to maintain the lower portion of the container 212 within a temperature range of from 250–350° F.

Thus, polymer (e.g., polyolefin) added to the container 212 is heated from 10–12 hours whereafter a scent or aroma imparting material which contains or consists of at least one of the 4,5,6,7-tetrahydro-polyalkylated-4-indane carbinols, carbinyl esters, carboxaldehydes, ketones and cyanides of our invention is quickly added to the melt. The material must be compatible with the polyolefin and forms a homogeneous liquid melt therewith. The scented material containing or consisting of at least one of the 4,5,6,7-tetrahydro-polyalkylated4-indane carbinols, carbinyl esters, carboxaldehydes, ketones and cyanides of our invention is of a type for the particular aroma desired and formulated specifically for the scenting purpose for which the polyolefin will be employed. The heat resisting coils and aromatic materials in some instances in solid or powdered form, may be employed or added to the polyolefin in the container 212. Generally, about 10–30% by weight of the scenting material is added to the polyolefin.

After the scent imparting material containing or consisting of at least one of the 4,5,6,7-tetrahydro-polyalkylated-4-indane carbinols, carbinyl esters, carboxaldehydes, ketones and cyanides of our invention is added to the container 212, the mixture is stirred for a few minutes, for example, 5–15 minutes, and maintained within the temperature ranges indicated previously by the heating coils 212A. The controls 216 and 220 are connected through cables 224 and 226 to a suitable supply of electric current for supplying the power for heating purposes. The controls 216 and 220 are connected to the heating coils 212A respectively, through wires 214 and 222.

Thereafter, the valve "V" is opened permitting the mass to flow outwardly through conduit 232 (shown in cross section by reference numeral 218) having a multiplicity of orifices 234 adjacent to the lower side thereof. The outer end of the conduit 232 is closed so that the liquid polymer (e.g., polyolefin or polyurethane, which is thermoplastic) and aroma imparting mixture (containing at least one of the 4,5,6,7-tetrahydro-polyalkylated-4-indane carbinols, carbinyl esters, carboxaldehydes, ketones and cyanides of our invention) will continuously drop through the orifices 234 downwardly from the conduit 232. During this time, the temperature of the polymer (e.g., polyolefin or thermoplastic polyurethane) and aroma mixture containing at least one of the 4,5,6,7-tetrahydro-polyalkylated-4-indane carbinols, carbinyl esters, carboxaldehydes, ketones and cyanides of our invention in the container 212 is accurately controlled so that a temperature in the range of from about 210–275° F. will exist in the conduit 232. The regulation of the temperature through the control 216 and the control 220 is essential in order to insure temperature balance to provide for the continuous dropping or dripping of molten polymer (e.g., polyolefin or thermoplastic polyurethane) and scenting material containing or consisting of at least one of the 4,5,6,7-tetrahydro-polyalkylated-4-indane carbinols, carbinyl esters, carboxaldehydes, ketones and cyanides of our invention through the orifices 234 at a rate which will insure the formation of droplets 236 which will fall downwardly onto a moving conveyor belt 238 trained to run between conveyor wheels 240 and 242 beneath the conduit 232.

When the droplets 236 fall onto the conveyor 238, they form pellets 244 which harden almost instantaneously and fall off the end of the conveyor 238 into a container 245 which is advantageously filled with water or some other suitable cooling liquid in order to insure the rapid cooling of each of the pellets. The pellets 244 are then collected from the container 245 and utilized in a process as illustrated, infra.

A feature of this aspect of the process of our invention is the provision for moistening the conveyor belt 238 to insure rapid formation of the solid polymer (e.g., polyolefin or thermoplastic polyurethane) scented pellets 244 without sticking to the belt. The belt 238 is advantageously of a material which will not normally stick to a melted plastic, but the moistening means 248 insures a sufficiently cold temperature of the belt surface for the adequate formation of the pellets 244. The moistening means comprises a container 250 which is continuously fed with water 254 to maintain a level for moistening a sponge element 256 which bears against the exterior surface of the belt 238.

The following Examples I–XI serve to illustrate the processes for preparing the compounds of our invention and the compounds useful for their organoleptic properties. Examples following Example XI (Examples XII, et seq.) illustrate organoleptic utilities of the 4,5,6,7-tetrahydro-polyalkylated-4-indane carbinols, carbinyl esters, carboxaldehydes, ketones and cyanides of our invention.

All parts and percentages given herein are by weight unless otherwise specified.

The invention is not to be limited to the examples, but is only limited by the scope of the claims appended hereto.

EXAMPLES I AND II

Preparation of 1,1,2,3,3-Pentamethyl-4-Formyl-4,5,6,7-Tetrahydroindane

Reactions:

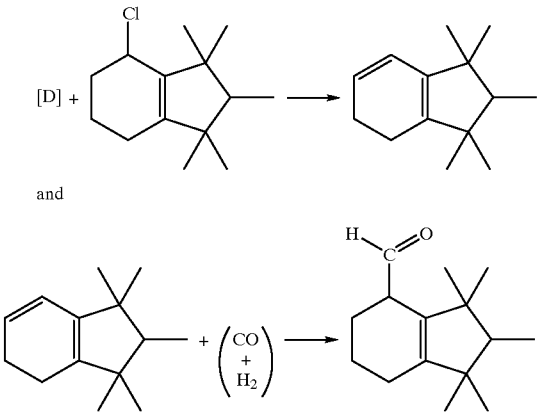

2,400 Grains of the mixture containing 45% by weight of the compound having the structure:

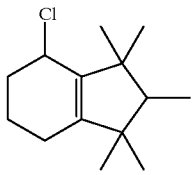

prepared according to the disclosure of U.S. Pat. No. 4,902,840 issued on Feb. 20, 1990, the specification for which is incorporated herein by reference; 20% 1,1,2,3,3-pentamethylindane and 35% hexahydro-1,1,2,3,3-pentamethylindane is heated to 150° C. Hydrogen chloride gas evolves and is passed through a caustic soda scrubber. This solution is then washed with a 5% aqueous sodium hydroxide solution, dried over anhydrous magnesium sulfate and used without further purification in the next step, the carrying out of an oxo-reaction.

1,822 Grams of the resulting compound having the structure:

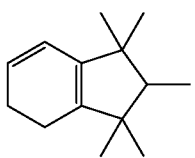

is admixed with 187 grams of a "oxo" reaction catalyst prepared as follows:

1.0 grams of $RhCl_3 \cdot H_2O$ is admixed with 30 grams of triphenyl phosphine having the structure:

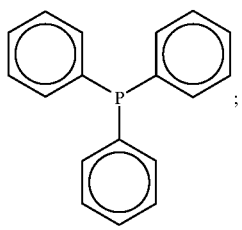

200 grams methanol; and 2.0 grams sodium bicarbonate.

The resulting mixture is heated at reflux for a period of 2.5 hours. The resulting mixture is placed in a 3 liter autoclave. The autoclave is closed and pressurized to 500 psig with a 50:50 weight:weight mixture of carbon monoxide and hydrogen. The temperature of the contents of the autoclave is heated to 120–125° C. The autoclave is continued to be pressurized with the carbon monoxide hydrogen mixture for a period of 2.5 hours while maintaining the temperature at 120–125° C. At the end of the 2.5 hour period, the autoclave is cooled and opened.

The resulting product is fractionally distilled yielding the following fractions:

| Fraction No. | Vapor Temperature | Liquid Temperature | Vacuum mm/Hg | Reflux Ratio |
|---|---|---|---|---|
| 1 | 23/109 | 23/128 | 18/19.4 | 1:1 |
| 2 | 110 | 130 | 19.4 | 1:1 |
| 3 | 110 | 131 | — | 4:1 |
| 4 | 111 | 133 | 19.4 | 1:1 |
| 5 | 110 | 134 | 17.8 | 2:1 |
| 6 | 110 | 134 | 16.0 | 2:1 |
| 7 | 109 | 135 | 15.1 | 2:1 |
| 8 | 109 | 136 | 14.9 | 2:1 |
| 9 | 110 | 137 | 14.8 | 2:1 |
| 10 | 113 | 138 | 15.0 | 4:1 |
| 11 | 114 | 140 | 14.5 | 4:1 |
| 12 | 116 | 143 | 15.0 | 4:1 |
| 13 | 117 | 145 | 14.8 | 4:1 |
| 14 | 122 | 145 | 14.2 | 4:1 |
| 13 | 117 | 145 | 14.8 | 4:1 |
| 14 | 122 | 145 | 14.2 | 4:1 |
| 15 | 138 | 145 | 14.0 | 4:1 |
| 16 | 140 | 146 | 13.9 | 4:1 |
| 17 | 123 | 135 | 5.4 | 4:1 |
| 18 | 124 | 136 | 5.8 | 1:1 |
| 19 | 119 | 133 | 4.9 | 1:1 |
| 20 | 118 | 133 | 4.8 | 1:1 |
| 21 | 117 | 133 | 4.9 | 1:1 |
| 22 | 117 | 133 | 4.8 | 1:1 |
| 23 | 117 | 133 | 4.7 | 1:1 |
| 24 | 121 | 140 | 5.07 | 1:1 |
| 25 | 121 | 142 | 5.10 | 1:1 |
| 26 | 124 | 169 | 5.65 | 1:1 |

Fraction 22 of the foregoing distillation is a mixture of isomers having the isomers having the structures:

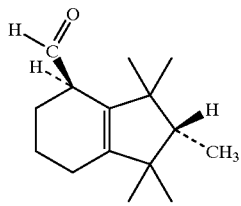

-continued and

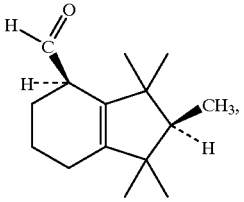

a mixture cis and trans isomers with the ratio of trans isomer (compound having the structure:

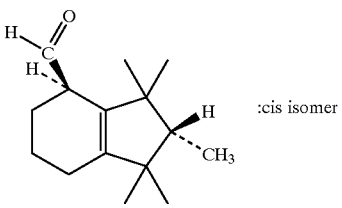    :cis isomer having the structure:

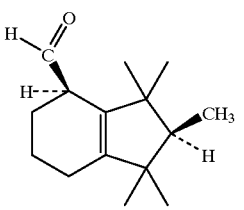

being 9:1. This is confirmed by NMR, IR and mass spectral analyses. Fractions 17–23 are bulked (having a distillation temperature of 117–123° C. at a vacuum of 4.7–5.4 mm/Hg.

The resulting bulked fractions 17–23 have a velvety, diffusive, sweet, rich, warm, intense musk, spicy, woody, balsamic, earthy, rooty and vetiver-like aroma with animalic, costus topnotes and sweet, musky, spicy, floral undertones.

EXAMPLE III

Production of 1,1,2,3,3-Pentamethyl-4-Hydroxy-4,5, 6-Tetrahydroindane

Reaction:

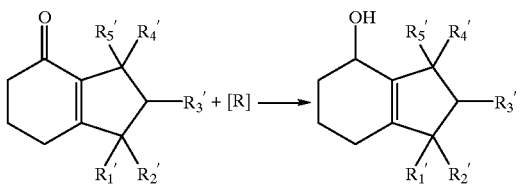

wherein R represents a "reducing agent"; and wherein $R_1'$, $R_2'$, $R_4'$ and $R_5'$ are the same or different methyl or ethyl; and $R_3'$ is hydrogen or methyl with the provisos that:

(i) when $R_3'$ is hydrogen, one of $R_1'$, $R_2'$, $R_4'$ and $R_5'$ is ethyl and the other is methyl; and (ii) when $R_3'$ is methyl, $R_1'$, $R_2'$, $R_4'$ and $R_5'$ is methyl. Approximately 90% of the mixture being one wherein $R_1'$, $R_2'$, $R_3$, $R_4'$ and $R_5'$ are methyl.

Into a 5 liter reaction vessel equipped with stiffer, thermometer, reflux condenser and heating mantle are placed 1,000 ml toluene with 1,000 grams of the compound having the structure:

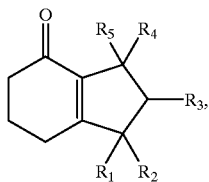

a mixture wherein 90% of the mixture contains the compound having the structure:

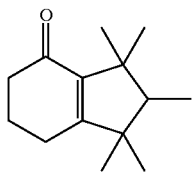

and 10% of the mixture contains compounds having the structure:

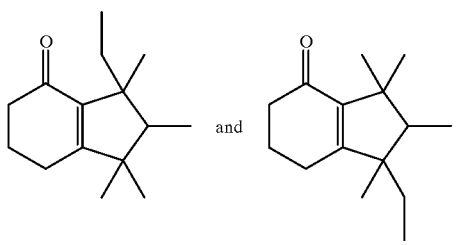

Over a period of 3 hours, 981 grams of a 70% solution of VITRIDE® in toluene is added to the mixture, maintaining the pot temperature at a temperature in the range of 64–71° C.

The resulting mixture is then refluxed at a temperature of 101° C. for a period of 3 hours with the toluene solvent being removed via a Bidwell apparatus.

The resulting product containing a mixture containing 90% of the compound having the structure:

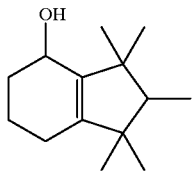

and 10% of the compounds having the structures:

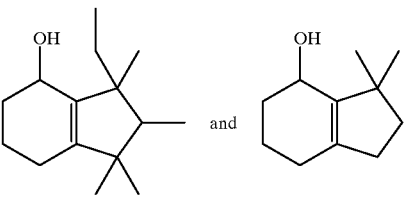

is then utilized in Example IV.

EXAMPLE IV

Preparation of 1,1,2,3,3-Pentamethyl-4,5-Dihydroindane

Reaction:

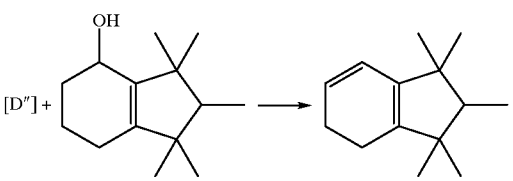

(wherein D″ is a dehydrating agent).

Into a 3 liter reaction vessel equipped with stirrer, thermometer, reflux condenser and Deen-Stark trap are placed a mixture of 1,000 grams of the compound having the structure:

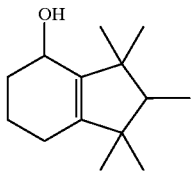

prepared according to Example III in admixture with the compounds having the structures:

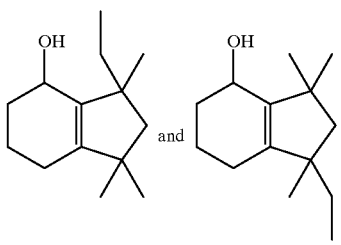

and 30 grams of paratoluene sulfonic acid and 100 ml toluene.

The resulting mixture is heated to 98° C. for a period of 4 hours with stirring.

An additional 30 grams of paratoluene sulfonic acid and 150 ml acetic acid is then added to the reaction mass and the reaction mass is continued to be stirred for a period of 4 hours while maintaining the temperature thereof at 98–99° C.

The resulting reaction mass is then placed in a separatory fennel and admixed with 1.5 liters of water. The aqueous phase is separated from the organic phase and the aqueous phase is washed successively with three 500 ml portions of saturated aqueous sodium chloride solution. The resulting product is then dried and fractionally distilled at a temperature in the range of 98–100° C. at 17.5–18.2 mm/Hg pressure.

The resulting product is a mixture containing 90% of the isomer having the structure:

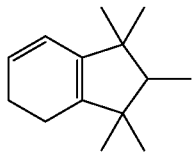

and 10% of the mixture of isomers having the structures:

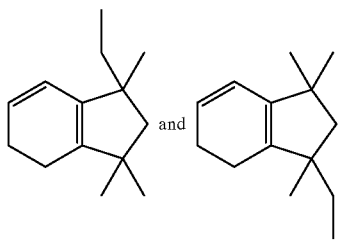

EXAMPLE V

Preparation of 1,1,2,3,3-Pentamethyl-4,5-Dihydroindane

Reaction:

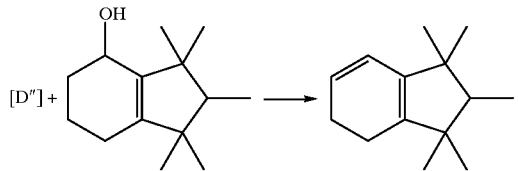

(wherein D" is a dehydrating agent).

1,000 Grams of the compounds having the structures:

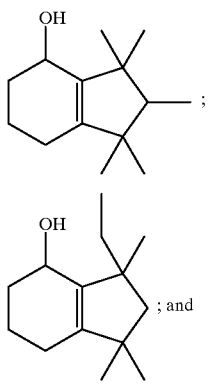

-continued

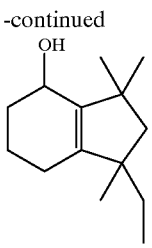

prepared according to Example II are admixed with 1,000 ml isopropyl alcohol and 30 grams of paratoluene sulfonic acid, and the resulting mixture is place in a 5 liter reaction vessel equipped with stirrer, thermometer, reflux condenser, heating mantle and Deen-Stark trap.

The resulting mixture is heated to 104° C. and maintained at 104° C. for a period of 4 hours with stirring.

At the end of the 4 hour period, the reaction mass is cooled and placed in a 12 liter sepratory funnel and admixed with 600 ml of a saturated sodium chloride solution. The aqueous phase is separated from the organic phase, and the organic phase is washed successively with three 400 ml 10% aqueous sodium carbonate solution portions. The resulting material is then dried over anhydrous magnesium sulfate and fractionally distilled yeilding the following fractions:

| Fraction No. | Vapor Temperature | Liquid Temperature | Vacuum mm/Hg | Reflux Ratio |
|---|---|---|---|---|
| 1 | 27/28 | 60/63 | 16.4/16.6 | 9:1/1:1 |
| 2 | 31 | 73 | 16.8 | 1:1/1:3 |
| 3 | 30/32 | 69/102 | 17.4/18.0 | 1:1/1:4 |
| 4 | 50 | 107 | 18.0 | 1:4 |
| 5 | 64/99 | 107/107 | 18.0/18.0 | 1:1/1:1 |
| 6 | 100 | 111 | 18.2 | 1:1/1:9 |
| 7 | 100 | 111 | 17.8 | 1:9 |
| 8 | 100 | 114 | 17.8 | 1:9 |
| 9 | 100 | 119 | 17.8 | 1:1 |
| 10 | 100 | 124 | 17.6 | 1:1 |
| 11 | 100 | 138 | 17.5 | 1:1 |
| 12 | 98/79 | 146 | 17.4 | 1:1 |
| 13 | 96/102 | 147/151 | 16.8/16.6 | 1:1/1:1 |
| 14 | 120 | 152 | 17.0 | 1:1 |
| 15 | 128 | 153 | 16.8 | 1:1 |

Distillation is carried out on a 24 inch Goodloe packed vacuum-jacketed, silver distillation column.

The resulting product is a mixture containing 90% by weight of the compound having the structure:

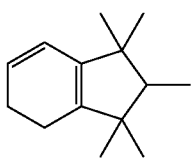

and 10% by weight of the mixture of compounds having the structures:

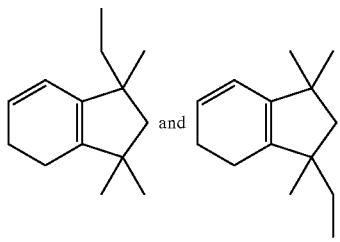

as confirmed by NMR, IR and mass spectral analysis.

EXAMPLE VI

Preparation of 1,1,2,3,3-Pentamethyl-4-Formyl-4,5,6,7-Tetrahydroindane

Reaction:

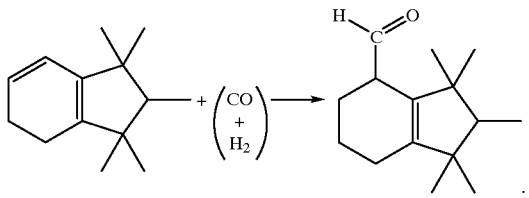

Into a 2 liter autoclave is place 1,240 grams of the mixture of compounds having the structures:

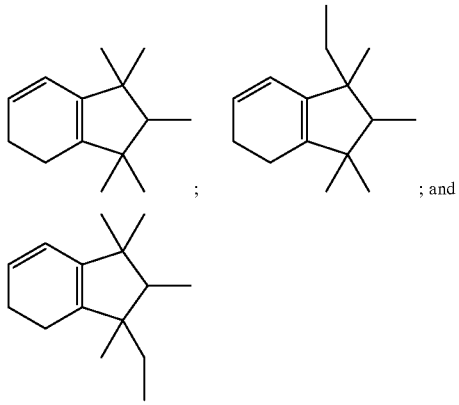

prepared according to Example V; 12.5 grams of isopropyl alcohol and 124 grams of the oxo reaction catalyst prepared as set forth in Example I/II, supra.

The autoclave is closed and pressurized to 450 psig with a 50:50 carbon monoxide: hydrogen mixture, and the temperature of the mixture is raised to 120–125° C. While under a pressure of 450 psig and at a temperature of 120–125° C., the autoclave is shaken for a period of 5.5 hours.

At the end of the 5.5 hour period, the autoclave is cooled and opened, and the product is fractionally distilled yielding the following fractions:

| Fraction No. | Vapor Temperature | Liquid Temperature | Vacuum mm/Hg | Reflux Ratio |
| --- | --- | --- | --- | --- |
| 1 | 29/36 | 75/110 | 206/20 | 100 |
| 2 | 71 | 119 | 3.1 | 4:1 |
| 3 | 69 | 113 | 2.67 | 4:1 |
| 4 | 71 | 118 | 2.9 | 4:1 |
| 5 | 71 | 117 | 2.9 | 4:1 |
| 6 | 71 | 118 | 2.89 | 4:1 |
| 7 | 75 | 111 | 2.8 | 4:1 |
| 8 | 77 | 125 | 2.8 | 4:1 |
| 9 | 87 | 127 | 2.8 | 4:1 |
| 10 | 97 | 127 | 2.8 | 4:1 |
| 11 | 104 | 127 | 3.0 | 4:1 |
| 12 | 109 | 127 | 3.2 | 4:1 |
| 13 | 112 | 127 | 3.2 | 4:1 |
| 14 | 111 | 130 | 3.3 | 4:1 |
| 15 | 111 | 130 | 3.2 | 1:4 |
| 16 | 112 | 130 | 3.2 | 1:4 |
| 17 | 106 | 128 | 2.1 | 1:4 |
| 18 | 99 | 125 | 1.7 | 1:4 |
| 19 | 72 | 138 | 1.82 | 1:4 |
| 20 | 34 | 190 | 2.1 | 1:4 |

Fractions 12–20 are bulked. NMR, IR, mass spectral and GLC analyses yield the information that the resulting product is a mixture of compounds 90% by weight of the compound having the structure:

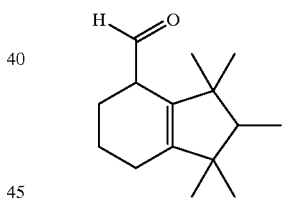

and 10% by weight of the compounds having the structures:

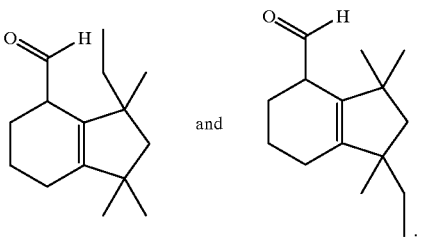

The resulting mixture has a velvety, diffusive, sweet, rich, warm, intense musk, spicy, woody, balsamic, earthy, rooty and vetiver-like aroma with animalic, costus topnotes and sweet, musky, spicy, floral undertones.

EXAMPLE VII

Preparation of 4,5,6,7-Tetrahydro-α,1,1,2,3,3-Hexamethyl-4-Indanemethanol

Reactions:

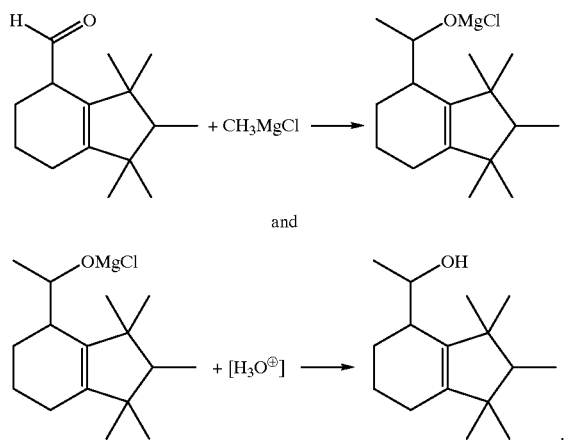

Into a 2 liter flask equipped with stirrer, thermometer, reflux condenser, heating mantle and cooling coils is placed 800 ml of a 3 molar solution of methyl magnesium chloride it tetrahydrofuran (2.4 moles).

While maintaining the reaction temperature at 15–20° C. over a period of 1.5 hours, 484 grams (2.2 moles) of the compound having the structure:

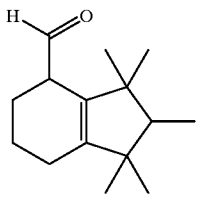

prepared according to Example VI is added to the mixture with stirring. The mixture is continued to be stirred at a temperature of 20° C. for a period of 30 minutes.

180 Grams of acetic acid in 500 ml of water at 0° C. is then added to the reaction mass with stirring over a period of 1.5 hours. The resulting reaction mass is then washed with an equal volume of 4% aqueous sodium carbonate solution.

The resulting organic phase is then dried over anhydrous magnesium sulfate and fractionally distilled yielding the following fractions:

| Fraction No. | Vapor Temperature | Liquid Temperature | Vacuum mm/Hg | Reflux Ratio |
|---|---|---|---|---|
| 1 | 23/33 | 23/115 | 220/70 | 100 |
| 2 | 112 | 137 | 1.7 | 4:1 |
| 3 | 117 | 144 | 1.7 | 4:1 |
| 4 | 112 | 145 | 1.5 | 1:1 |
| 5 | 118 | 144 | 1.4 | 1:1 |
| 6 | 117 | 144 | 1.3 | 1.1 |
| 7 | 118 | 146 | 1.6 | 1:1 |
| 8 | 117 | 144 | 1.6 | 1:1 |
| 9 | 118 | 146 | 1.5 | 1:1 |
| 10 | 116 | 148 | 1.4 | 1:1 |
| 11 | 118 | 185 | 1.2 | 1:1 |

Fractions 3–10 are bulked.

The resulting product has the structure:

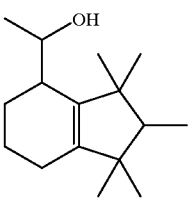

as confirmed by NMR, IR and mass spectral analyses.

The intermediate therefor has the structure:

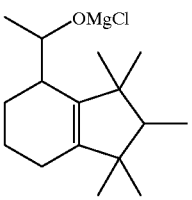

and can be isolated as a "isolated intermediate."

EXAMPLE VIII

Preparation of 4,5,6,7-Tetrahydro-α,1,1,2,3,3-Hexamethyl-4-Indaneketone

Reaction:

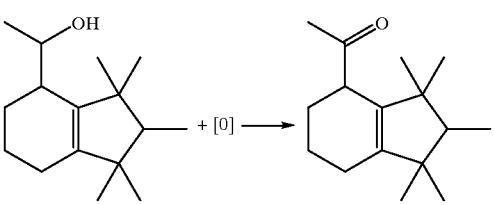

(wherein [O] is an oxidizing agent, in this case, sodium dichromate).

Into a 2 liter reaction vessel equipped with stirrer, thermometer, reflux condenser and heating mantle is placed a solution of 137 grams of sodium dichromate (0.46 moles) in 330 grams of water.

Over a period of 30 minutes, 360 grams of the bulked distillation fractions 3–10 of the reaction product of Example VII, which is the compound having the structure:

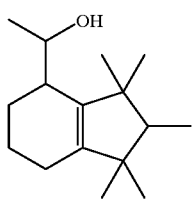

is added to the reaction mass. The resulting reaction is then heated to 50° C. with stirring and maintained at 50° C. Over a period of one hour, 90 grams of concentrated sulfuric acid (0.92 moles) is added to the reaction mass. The reaction mass is maintained at 50° C. for a period of 3 hours.

At the end of the 3 hour period, the reaction mass is admixed with 375 grams of concentrated hydrochloric acid while maintaining the temperature thereof at 50° C. The reaction mass is then stirred at 50° C. for an additional one hour period.

The reaction mass is then admixed with 150 ml water. The organic phase is separated from the aqueous phase, and the organic phase is washed with an equal volume of saturated sodium bicarbonate. The resulting organic phase is then dried over anhydrous magnesium sulfate and fractionally distilled yielding the following fractions:

| Fraction No. | Vapor Temperature | Liquid Temperature | Vacuum mm/Hg | Reflux Ratio |
|---|---|---|---|---|
| 1 | 33/41 | 23/125 | 205/70 | 100 |
| 2 | 122 | 153 | 4.1 | 9:1 |
| 3 | 128 | 152 | 5.1 | 9:1 |
| 4 | 131 | 154 | 5.1 | 9:1 |
| 5 | 130 | 154 | 4.9 | 9:1 |
| 6 | 131 | 154 | 4.7 | 9:1 |
| 7 | 130 | 154 | 4.3 | 9:1 |
| 8 | 131 | 157 | 4.4 | 4:1 |
| 9 | 131 | 160 | 4.2 | 4:1 |
| 10 | 132 | 177 | 4.1 | 4:1 |
| 11 | 128 | 184 | 4.2 | 4:1 |
| 12 | 119 | 218 | 2.6 | 4:1 |
| 13 | 69 | 220 | 2.3 | 4:1 |

Fractions 4–11 are bulked. Bulked fractions 4–11 are confused by NMR, IR and mass spectral analysis to be the compound having the structure:

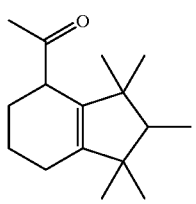

EXAMPLE IX

Preparation of 1,1,2,3,3-Pentamethyl-4-Hydroxymethyl-4,5,6,7-Tetrahydroindane

Reaction:

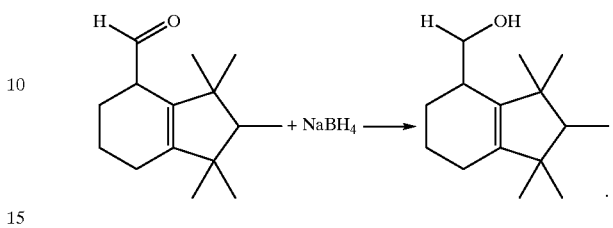

Into a 2 liter reaction vessel equipped with stirrer, thermometer, reflux condenser, heating mantle and addition fennel are placed 800 ml of isopropyl alcohol and 27 grams of sodium borohydride (0.7 moles). The resulting mixture is heated to 60° C., and over a period of 1.5 hours, 455 grains (2.07 moles) of the compound having the structure:

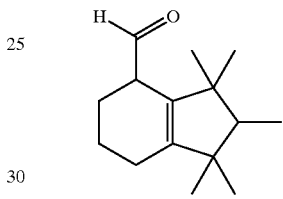

prepared-according to Example VI is added to the reaction mass while maintaining the reaction mass temperature at 78–80° C.

The reaction mass is maintained at 78–80° C. with stirring for a period of 2 hours. At the end of the 2 hour period, the reaction mass is admixed with an equal volume of 5% aqueous hydrochloric acid. The reaction mass is then refluxed for a period of 1 hour. The resulting product is then washed with an equal volume of 5% aqueous sodium bicarbonate.

The organic phase is separated from the aqueous phase and the organic phase is dried over anhydrous magnesium sulfate. The resulting product is then fractionally distilled yielding the following fractions:

| Fraction No. | Vapor Temperature | Liquid Temperature | Vacuum mm/Hg | Reflux Ratio |
|---|---|---|---|---|
| 1 | 23/37 | 22/115 | 240/10 | 100 |
| 2 | 108 | 131 | 1.6 | 9:1 |
| 3 | 111 | 135 | 1.6 | 9:1 |
| 4 | 116 | 137 | 1.7 | 1:1 |
| 5 | 123 | 143 | 1.8 | 1:1 |
| 6 | 117 | 139 | 0.9 | 1:1 |
| 7 | 106 | 138 | 0.63 | 1:1 |
| 8 | 108 | 139 | 1.1 | 1:1 |
| 9 | 111 | 143 | 1.4 | 1:1 |
| 10 | 111 | 142 | 1.4 | 1:1 |
| 11 | 118 | 143 | 1.7 | 1:1 |
| 12 | 119 | 145 | 1.8 | 1:1 |
| 13 | 122 | 148 | 1.1 | 1:1 |
| 14 | 118 | 157 | 1.1 | 1:1 |

Fractions 6–11 are bulked. Fractions 6–11 are confirmed by NMR, IR and mass spectral analyses to have the structure:

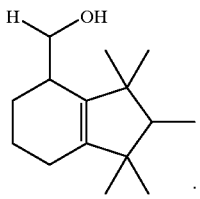

EXAMPLE X

Preparation of 1,1,2,3,3-Pentamethyl-4-Acetoxymethyl-4,5,6,7-Tetrahydroindane

Reaction:

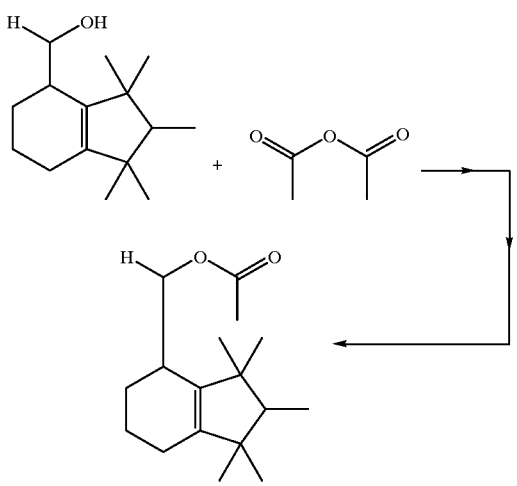

Into a 2 liter reaction vessel equipped with stirrer, thermometer, reflux condenser and heating mantle are placed a mixture of 160 grams of aceticanhydride and 260 grams of the distillation product of reaction product of Example IX, the compound having the structure:

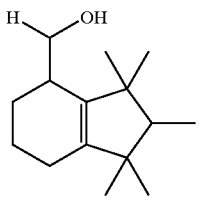

The resulting mixture is heated to 110° C. with stirring and maintained at 110° C. for a period of one hour. At the end of the one hour period, the reaction mass is cooled to 80° C. and admixed with an equal volume of water. The resulting reaction mass is then maintained at 80° C. for a period of one hour and then washed with an equal volume of 5% aqueous sodium carbonate solution.

The aqueous phase is separated from the organic phase and the organic phase is dried over anhydrous magnesium sulfate. The resulting organic phase is fractionally distilled following fractions:

| Fraction No. | Vapor Temperature | Liquid Temperature | Vacuum mm/Hg | Reflux Ratio |
|---|---|---|---|---|
| 1 | 23/32 | 23/110 | 150/40 | 100 |
| 2 | 133 | 144 | 0.7 | 4:1 |
| 3 | 137 | 149 | 0.7 | 4:1 |
| 4 | 128 | 149 | 0.7 | 4:1 |
| 5 | 126 | 147 | 0.7 | 4:1 |
| 6 | 126 | 148 | 0.7 | 4:1 |
| 7 | 125 | 150 | 0.7 | 4:1 |
| 8 | 124 | 153 | 0.7 | 4:1 |
| 9 | 123 | 152 | 0.7 | 4:1 |
| 10 | 122 | 164 | 0.7 | 4:1 |
| 11 | 111 | 195 | 0.7 | 4:1 |

Fractions 4–10 are bulked. Bulked distillation fractions 4–10 are confirmed by NMR, IR, mass spectral and GLC analyses to be the compound having the structure:

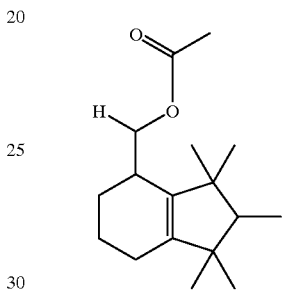

EXAMPLE XI

Preparation of 1,1,2,3,3-Pentamethyl-4-Cyano-4,5,6,7-Tetrahydroindane

Reactions:

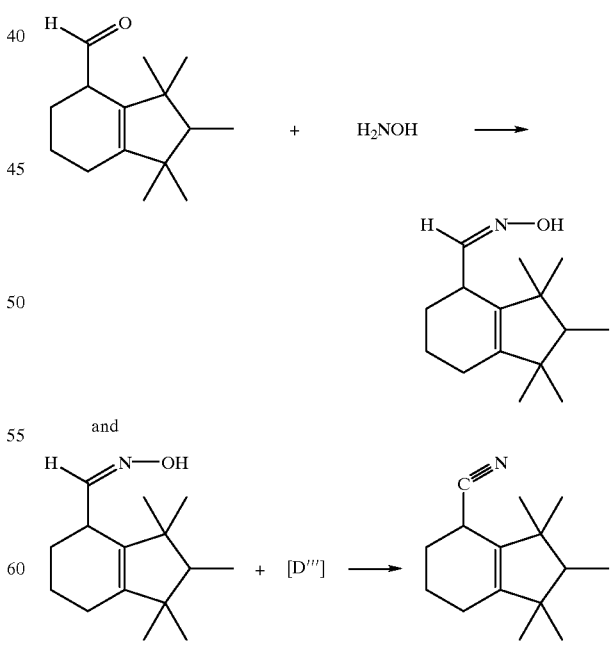

(wherein D''' is a dehydrating agent).

Into a 3 liter reaction vessel equipped with stirrer, thermometer, reflux condenser and heating mantle is placed a mixture of 200 grams of xylene and 404 grams of bulked distillation fractions 12–20 of Example VI containing the compound having the structure:

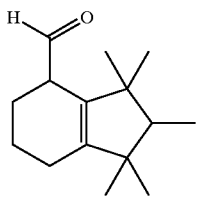

Over a period of 2 hours while maintaining the reaction mass temperature at 55–60° C., 148 grams of hydroxylamine (2.24 moles) is added to the reaction mass. In a separate 1 liter reaction vessel equipped with stirrer, thermometer and reflux condenser are placed 312 grams (3.06 moles) of aceticanhydride and 4 grams of ferrous gluconate. The aceticanhydride-ferrous gluconate mixture is refluxed for a period of 2 hours at 133° C. The ferrous gluconate-aceticanhydride mixture is then added over a period of 2 hours to the hydroxylamine/1,1,2,3,3-pentamethyl-4-formyl-4,5,6,7-tetrahydroindane solution with stirring.

The resulting mixture is heated to reflux and refluxed for a period of 2 hours at atmospheric pressure at a temperature of 142° C. The resulting mixture is then stirred at a temperature of 120° C. for a period of 6 hours. The resulting mixture is then admixed with an equal volume of saturated sodium carbonate.

The organic phase is separated from the aqueous phase and the organic phase is then fractionally distilled yielding the following fractions:

| Fraction No. | Vapor Temperature | Liquid Temperature | Vacuum mm/Hg | Reflux Ratio |
|---|---|---|---|---|
| 1 | 23/43 | 23/135 | 206/10 | 100 |
| 2 | 108 | 142 | 1.2 | 4:1 |
| 3 | 116 | 143 | 1.7 | 4:1 |
| 4 | 104 | 144 | 1.0 | 3:1 |
| 5 | 103 | 144 | 0.8 | 3:1 |
| 6 | 112 | 146 | 1.4 | 3:1 |
| 7 | 115 | 147 | 1.6 | 3:1 |
| 8 | 101 | 147 | 0.720 | 3:1 |
| 9 | 106 | 152 | 1.00 | 3:1 |
| 10 | 108 | 160 | 1.05 | 3:1 |
| 11 | 108 | 170 | 1.02 | 3:1 |
| 12 | 102 | 220 | 1.23 | 3:1 |

Fractions 8–11 are bulked. Bulked distillation fractions 8–11 are confirmed by NMR IR, mass spectral and GLC analyses to contain the compound having the structure:

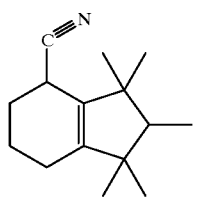

with the impurity having the structure:

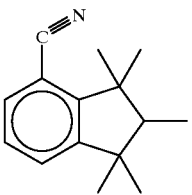

The resulting product has a musky, woody-amber, powdery, vetiver aroma.

The intermediate for the reaction, when isolated, is confirmed to have the structure:

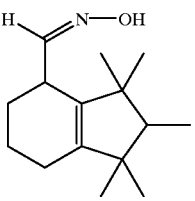

EXAMPLE XII

The 4,5,6,7-tetrahydro-polyalkylated-4-indane carbinols, carbinyl esters, carboxaldehydes, ketones and cyanides of our invention produced according to Examples I–XI have very long lasting, substantive and intense velvety, difflusive, sweet, rich, warm, intense musk, spicy, woody, balsamic, earthy, rooty and vetiver-like aromas with animalic, costus topnotes and sweet, musky, spicy, floral undertones which may be utilized to a great extent inexpensive functional product. The following pine fragrance demonstrates the use of these materials in perfume compositions:

| Ingredients | Parts by Weight |
|---|---|
| Isobornyl acetate | 100 |
| Camphor | 10 |
| Terpineol | 10 |
| Fir balsam absolute (50% in diethyl phthalate | 20 |
| Coumarin | 4 |
| Linalool | 30 |
| Anethol | 30 |
| Fenchyl alcohol | 2 |
| Lemon terpenes washed | 10 |
| d-Borneol | 50 |
| Galbanum oil | 50 |
| Turpentine Russian | 5 |
| Eucalyptol | 50 |
| Ethyl maltol (1% in diethyl phthalate) | 40 |
| The compound having the structure: | 15 |

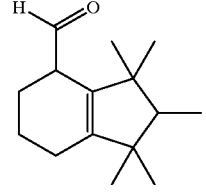

Bulked distillation fractions 12–20 of Example VI.

The compound having the structure:

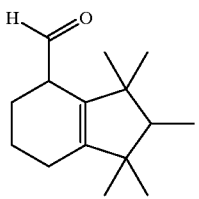

prepared according to Example VI adds to this pine fragrance animalic and costus topnotes with velvety, diffusive, sweet, rich, warm, intense musk, spicy, woody, balsamic, earthy, rooty and vetiver-like undertones. Accordingly, the perfume composition of this Example XII can be described as: "piney with velvety, diffusive, sweet, rich, warm, intense musk, spicy, woody, balsamic, earthy, rooty and vetiver-like undertones and animalic and costus topnotes."

EXAMPLE XII(B)

Musk Fragrance

The following musk fragrance demonstrates the use of 4,5,6,7-tetrahydro-α,1,1,2,3,3-hexamethyl-4-indaneketone, a ketone of our invention in perfume compositions:

| Ingredients | Parts by Weight |
|---|---|
| The compound having the structure: 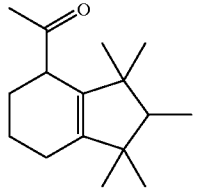 prepared according to Example VIII, bulked distillation fractions 4-11. | 32 |
| The compound having the structure: 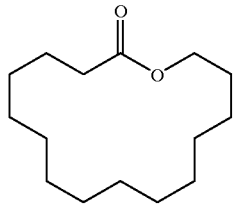 | 64 |
| The compound having the structure: 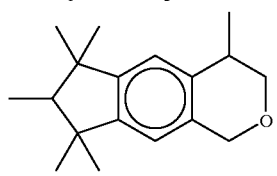 | 32 |
| The compound having the structure 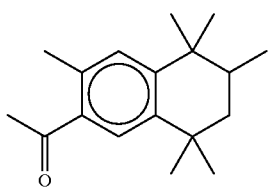 | 16 |
| The compound having the structure 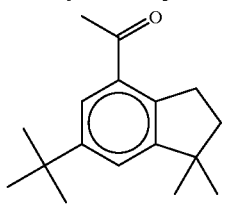 | 16 |
| The compound having the structure: 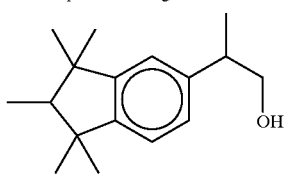 | 20 |
| The compound having the structure: 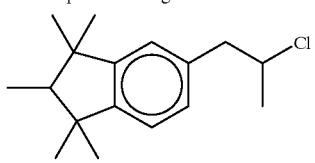 | 20 |
| The compound having the structure: 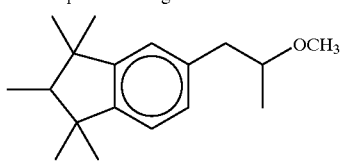 | 20 |

The 4,5,6,7-tetrahydro-α,1,1,2,3,3-hexamethyl-4-indaneketone prepared according to Example VIII, supra, imparts to the musk perfume formulation, vetiver, floral, ambery, warm, sensual and powdery undertones with warm, sensual, creamy and powdery topnotes. Accordingly, the fragrance of this Example XII(B) has an aroma that can be described as:

"musky with vetiver, floral, ambery, warm, sensual and powdery undertones and warm, sensual, creamy and powdery topnotes."

EXAMPLE XIII

Cosmetic Powder Preparation

A cosmetic powder is prepared by mixing in a ball mill 100 grams of talcum powder with 0.25 grams of one of the substances set forth in Table I below containing at least one of the 4,5,6,7-tetrahydro-polyalkylated-4-indane carboxal dehydes or ketones of our invention. Each of the cosmetic powders has an excellent aroma as described in Table I below:

food grade ethanol solutions. Distinctive aromas as set forth in Table I of Example XIII, supra, are imparted to the

TABLE I

| Perfumery Substance | Perfumery Nuances |
| --- | --- |
| The compound having the structure:<br />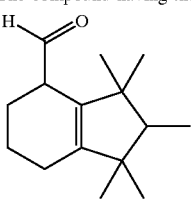<br />prepared according to Example VI, bulked distillation fractions 12–20. | A velvety, diffusive, sweet, rich, warm, intense musk, spicy, woody, balsamic, earthy, rooty and vetiver-like aroma with animalic, costus topnotes and sweet, musky, spicy, floral undertones. |
| The perfume composition of Example XII(A). | A piney aroma with animalic and costus topnotes and velvety, diffusive, sweet, rich, warm, intense musk, spicy, woody, balsamic, earthy, rooty and vetiver-like undertones. |
| The compound having the structure:<br />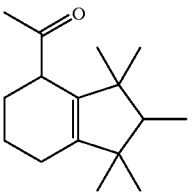<br />prepared according to Example VIII, bulked distillation fractions 4-11. | A musky, vetiver, floral, ambery, warm, sensual and powdery aroma with warm, sensual, creamy, powdery and musky topnotes. |
| The perfume composition of Example XII(B). | A musky aroma with vetiver, floral, ambery, warm, sensual and powdery undertones and warm, sensual, creamy and powdery topnotes. |

EXAMPLE XIV

Perfumed Liquid Detergent

Concentrated liquid detergents (lysine salt of n-dodecylbenzene sulfonic acid as more specifically described in U.S. Pat. No. 3,948,818 issued on Apr. 6, 1976, the specification for which is incorporated by reference herein) with aromas as set forth in Table I of Example XIII, supra, are prepared containing 0.10%, 0.15%, 0.20%, 0.25%, 0.30% and 0.35% of each of the substances of Table I of Example XIII. They are prepared by adding and homogeneously admixing the appropriate quantity of one of the substances of Table I of Example XIII in the liquid detergent. The detergents all possess excellent aromas as set forth in Table I of Example XIII.

EXAMPLE XV

Preparation of a Cologne and Handkerchief Perfume

The substances set forth in Table I of Example XIII are incorporated separately into colognes at concentrations of 2.0%, 2.5%, 3.0%, 3.5%, 4.0%, 4.5% and 5.0% in 75%, 80%, 85% and 90% aqueous food grade ethanol solutions and into handkerchief perfumes at concentrations of 15%, 20%, 25% and 30% in 80%, 85%, 90% and 95% aqueous colognes and to the handkerchief perfume compositions at all levels indicated.

EXAMPLE XVI

Preparation of Soap Composition

100 Grams of soap chips (IVORY®, produced by the Proctor & Gamble Company of Cincinnati, Ohio) are admixed with 1 gram of each of the substances of Table I of Example XII, supra, until homogeneous compositions are obtained. The homogeneous compositions are each separated then heated under 3 atmospheres pressure at 180° C. for a period of 3 hours and the resulting liquid samples are placed in soap molds. The resulting soap cakes, on cooling, manifest excellent long lasting aromas as set forth in Table I of Example XIII.

EXAMPLE XVII

Preparation of Solid Detergent Compositions

Detergents are prepared from the following ingredients according to Example II of Canadian Letters Pat. No. 1,007,948, the specification for which is incorporated by reference herein:

| Ingredients | Parts by Weight |
|---|---|
| NEODOL ® 45-11 (a $C_{14}$–$C_{15}$ alcohol ethoxylated with 11 moles of ethlene oxide) | 12 |
| Sodium carbonate | 55 |
| Sodium citrate | 20 |
| Sodium sulfate, water brighteners | q.s. |

This detergent is a phosphate-free detergent. A total of 100 grams of said detergent is admixed separately with 0.10, 0.15, 0.20 and 0.25 grams of each of the substances of Table I of Example XIII. Each of the detergent samples has excellent aromas as set forth in Table I of Example XIII.

EXAMPLE XVIII

Dryer-Added Fabric Softener Article

Utilizing the procedure of Example II at column 15 of U.S. Pat. No. 3,623,396, the specification for which is incorporated by reference herein, a non-woven cloth substrate useful as a dryer-added fabric softening article of manufacture is prepared wherein the substrate, the substrate coating and the outer coating and the performing material are as follows:

1. a water "dissolvable" paper ("Dissolve Paper");
2. Adogen 448 (m.p. about 140° F.) as the substrate coating; and
3. an outer coating having the following formulation:
   57%—$C_{20}$–$C_{22}$ HAPS;
   22%—isopropyl alcohol;
   20%—antistatic agent; and
   1%—of one of the substances of Table I of Example XIII, supra.

Fabric softening compositions containing one of the substances of Table I of Example XIII consist essentially of a substrate having a weight of about 3 grams per 100 square inches of substrate coating having a weight of about 1.85 grams per 100 square inches; and a outer coating having a weight of about 1.4 grams per 100 square inches thereby providing a total aromatized substrate and an outer coating weight ratio of about 1:1 by weight of the substrate.

Pleasant aromas as set forth in Table I of Example XIII are imparted to the headspace in the dryer on operation thereof using the said dryer-added fabric softening non-woven fabric.

What is claimed is:

1. A compound defined according to the structure:

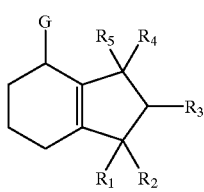

wherein $R_1$, $R_2$, $R_4$ and $R_5$ are the same or different methyl or ethyl and $R_3$ is hydrogen or methyl with the provisos that:
(i) when $R_3$ is hydrogen, one of $R_1$, $R_2$, $R_4$ and $R_5$ is ethyl and the other is methyl; and
(ii) when $R_3$ is methyl, then one of $R_1$, $R_2$, $R_4$ and $R_5$ is methyl; and wherein G is a moiety selected from the group consisting of:

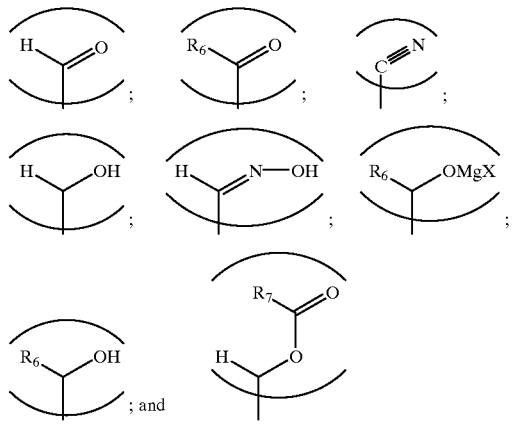

and wherein $R_6$ and $R_7$ are $C_1$–$C_3$ lower alkyl.

2. The compound having the structure:

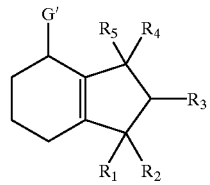

wherein $R_1$, $R_2$, $R_4$ and $R_5$ are the same or different methyl or ethyl and $R_3$ is hydrogen or methyl with the provisos that:
(i) when $R_3$ is hydrogen, one of $R_1$, $R_2$, $R_4$ and $R_5$ is ethyl and the other groups are methyl; and
(ii) when $R_3$ is methyl, then one of $R_1$, $R_2$, $R_4$ and $R_5$ is methyl; and wherein G' is a moiety selected from the group consisting of:

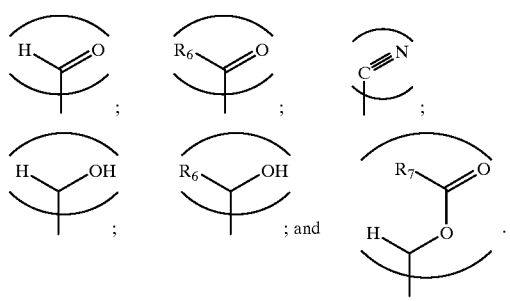

3. A compound of claim 2 which is a mixture of racemic isomers having the structures:

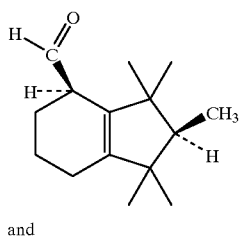

and

-continued

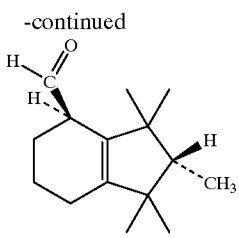

with the ratio of cis isomer having the structure:

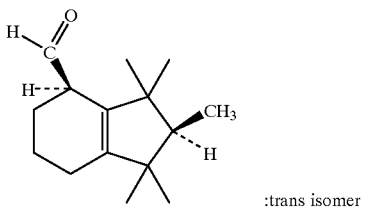

:trans isomer having the structure:

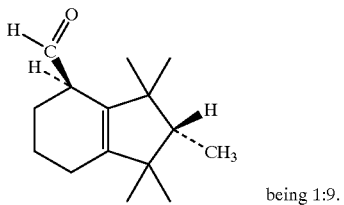

being 1:9.

4. A process for preparing a compound having the structure:

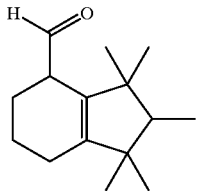

comprising the step of admixing a compound having the structure;

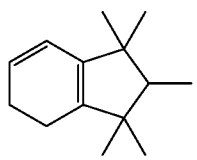

with a mixture of carbon monoxide and hydrogen in the presence of a "oxo" reaction catalyst.

5. A process for augmenting or enhancing the aroma of a consumable material selected from the group consisting of perfume compositions, perfumed articles and colognes comprising the step of intimately admixing with a perfumed article base, a perfume base or a cologne base an aroma imparting, augmenting or enhancing amount of at least one composition of matter defined according to claim 2.

6. The process of claim 5 wherein the consumable material is a perfume composition.

7. The process of claim 5 wherein the consumable material is a cologne.

8. The process of claim 5 wherein the consumable material is a perfumed article, and the perfumed article is an anionic, cationic, nonionic or zwitterionic detergent.

9. A perfumed composition comprising a perfume base and intimately admixed therewith an aroma imparting, augmenting or enhancing quantity of at least one composition of matter defined according to claim 2.

10. A perfumed article comprising a perfumed article base and intimately admixed therewith an aroma imparting, augmenting or enhancing quantity of at least one composition of matter defined according to claim 2.

11. A cologne comprising water, ethanol and an aroma-imparting amount of at least one composition of matter defined according to claim 2.

12. A perfume polymer comprising a microporous polymer and contained in the interstices thereof at least one composition of matter defined according to claim 2.

13. At least one stereoisomer defined according to the structure:

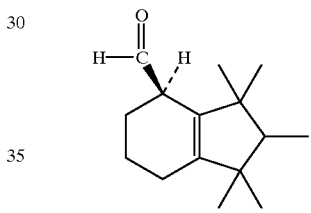

or

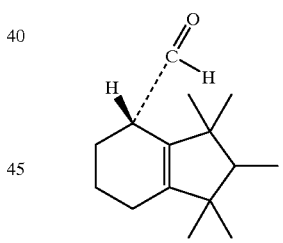

having an enantiomeric excess percent of greater than 50%, [EE%>50%].

14. At least one stereoisomer defined according to the structure:

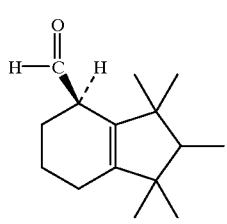

or

-continued

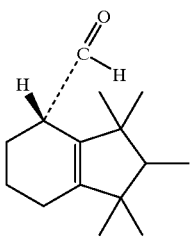

having an enantiomeric excess percent equal to 90%, [EE%= 90%].

15. A compound of claim 2 having the structure:

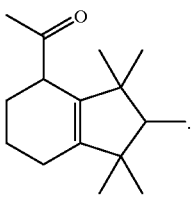

16. A process for augmenting or enhancing the aroma of a consumable material selected from the group consisting of perfume compositions, perfumed articles and colognes comprising the step of intimately admixing with a perfumed article base, a perfume base or a cologne base an aroma imparting, augmenting or enhancing amount and concentration of the compound defined according to claim 15.

17. A process for augmenting or enhancing the aroma of a consumable material selected from the group consisting of perfume compositions, perfumed articles and colognes comprising the step of intimately admixing with a perfumed article base, a perfume base or a cologne base an aroma imparting, augmenting or enhancing amount and concentration of the composition of matter defined according to claim 3.

18. A perfumed polymer comprising a microporous polymer and contained within the interstices thereof the compound defined according to claim 15.

19. A perfumed polymer comprising a microporous polymer and contained within the interstices thereof the composition of matter defined according to claim 3.

* * * * *